US012760358B2

(12) United States Patent
Steel et al.

(10) Patent No.: US 12,760,358 B2
(45) **Date of Patent: *Oct. 13, 2026**

(54) EXTERNAL FILES FOR DISTRIBUTION OF MOLECULAR DIAGNOSTIC TESTS AND DETERMINATION OF COMPATIBILITY BETWEEN TESTS

(71) Applicant: Augusta SpinCo Corporation, Milford, MA (US)

(72) Inventors: Adam Steel, Fallston, MD (US); Thomas Wojeck, Sparks, MD (US); Michael Young, Sparks, MD (US); Mark Larsen, Sparks, MD (US)

(73) Assignee: Augusta SpinCo Corporation, Milford, MA (US)

( * ) Notice: Subject to any disclaimer, the term of this patent is extended or adjusted under 35 U.S.C. 154(b) by 1560 days.

This patent is subject to a terminal disclaimer.

(21) Appl. No.: 17/084,442

(22) Filed: Oct. 29, 2020

(65) Prior Publication Data

US 2021/0147923 A1 May 20, 2021

Related U.S. Application Data

(63) Continuation of application No. 13/757,392, filed on Feb. 1, 2013, now Pat. No. 10,822,644.

(60) Provisional application No. 61/594,867, filed on Feb. 3, 2012.

(51) Int. Cl.

| | |
|---|---|
| ***C12Q 1/6844*** | (2018.01) |
| ***G01N 35/00*** | (2006.01) |
| ***G16B 30/00*** | (2019.01) |

(52) U.S. Cl.
CPC ....... *C12Q 1/6844* (2013.01); *G01N 35/0092* (2013.01); *G16B 30/00* (2019.02); *G01N 2035/0094* (2013.01)

(58) Field of Classification Search
CPC .................. C12Q 1/6844; G16B 30/00; G01N 35/0092; G01N 2035/0094
See application file for complete search history.

(56) References Cited

U.S. PATENT DOCUMENTS

| | | | |
|---|---|---|---|
| D189,404 | S | 12/1960 | Nicolle |
| 3,050,239 | A | 8/1962 | Williams |
| 3,444,742 | A | 5/1969 | Ellis et al. |
| 3,905,772 | A | 9/1975 | Hartnett et al. |

(Continued)

FOREIGN PATENT DOCUMENTS

| | | |
|---|---|---|
| AU | 1357102 | 3/2002 |
| AU | 3557502 | 7/2002 |

(Continued)

OTHER PUBLICATIONS

Davis et al., "Surface vibrational sum frequency and Raman studies of PAMAM G0, G1 and acylated Pamam G0 dendrimers". Anal Chimica Acta. Oct. 31, 2003;496(1-2): 117-131.

(Continued)

*Primary Examiner* — Charles Capozzi
*Assistant Examiner* — Alex Ramirez
(74) *Attorney, Agent, or Firm* — Knobbe, Martens, Olson & Bear, LLP

(57) ABSTRACT

Embodiments disclosed herein relate to methods and systems for performing an automated assay, and particularly to performing an assay on a plurality of samples on an automated instrument.

24 Claims, 5 Drawing Sheets

(56) References Cited

U.S. PATENT DOCUMENTS

| | | | |
|---|---|---|---|
| 3,985,649 | A | 10/1976 | Eddelman |
| 4,018,089 | A | 4/1977 | Dzula et al. |
| 4,018,652 | A | 4/1977 | Lanham et al. |
| 4,038,192 | A | 7/1977 | Serur |
| 4,055,395 | A | 10/1977 | Honkawa et al. |
| D249,706 | S | 9/1978 | Adamski |
| 4,139,005 | A | 2/1979 | Dickey |
| D252,157 | S | 6/1979 | Kronish et al. |
| D252,341 | S | 7/1979 | Thomas |
| D254,687 | S | 4/1980 | Fadler et al. |
| 4,212,744 | A | 7/1980 | Oota |
| D261,033 | S | 9/1981 | Armbruster |
| D261,173 | S | 10/1981 | Armbruster |
| 4,301,412 | A | 11/1981 | Hill et al. |
| 4,439,526 | A | 3/1984 | Columbus |
| 4,457,329 | A | 7/1984 | Werley et al. |
| 4,466,740 | A | 8/1984 | Kano et al. |
| 4,472,357 | A | 9/1984 | Levy et al. |
| 4,504,582 | A | 3/1985 | Swann |
| 4,522,786 | A | 6/1985 | Ebersole |
| D279,817 | S | 7/1985 | Chen et al. |
| D282,208 | S | 1/1986 | Lowry |
| 4,599,315 | A | 7/1986 | Terasaki et al. |
| 4,612,873 | A | 9/1986 | Eberle |
| 4,612,959 | A | 9/1986 | Costello |
| D288,478 | S | 2/1987 | Carlson et al. |
| 4,647,432 | A | 3/1987 | Wakatake |
| 4,654,127 | A | 3/1987 | Baker et al. |
| 4,673,657 | A | 6/1987 | Christian |
| 4,678,752 | A | 7/1987 | Thorne et al. |
| 4,683,195 | A | 7/1987 | Mullis et al. |
| 4,683,202 | A | 7/1987 | Mullis |
| 4,698,302 | A | 10/1987 | Whitehead et al. |
| D292,735 | S | 11/1987 | Lovborg |
| 4,720,374 | A | 1/1988 | Ramachandran |
| 4,724,207 | A | 2/1988 | Hou et al. |
| 4,795,698 | A | 1/1989 | Owen et al. |
| 4,798,693 | A | 1/1989 | Mase et al. |
| 4,800,022 | A | 1/1989 | Leonard |
| 4,827,944 | A | 5/1989 | Nugent |
| 4,841,786 | A | 6/1989 | Schulz |
| D302,294 | S | 7/1989 | Hillman |
| 4,855,110 | A | 8/1989 | Marker et al. |
| 4,871,779 | A | 10/1989 | Killat et al. |
| 4,889,818 | A | 12/1989 | Gelfand et al. |
| 4,895,650 | A | 1/1990 | Wang |
| 4,902,624 | A | 2/1990 | Columbus et al. |
| 4,914,710 | A | 4/1990 | Ward et al. |
| 4,919,829 | A | 4/1990 | Gates et al. |
| 4,921,809 | A | 5/1990 | Schiff et al. |
| 4,935,342 | A | 6/1990 | Seligson et al. |
| 4,946,562 | A | 8/1990 | Guruswamy |
| 4,948,561 | A | 8/1990 | Hinckley et al. |
| 4,949,742 | A | 8/1990 | Rando et al. |
| D310,413 | S | 9/1990 | Bigler et al. |
| 4,963,498 | A | 10/1990 | Hillman |
| 4,965,188 | A | 10/1990 | Mullis et al. |
| 4,967,950 | A | 11/1990 | Legg et al. |
| D312,692 | S | 12/1990 | Bradley |
| 4,978,502 | A | 12/1990 | Dole et al. |
| 4,978,622 | A | 12/1990 | Mishell et al. |
| 4,989,626 | A | 2/1991 | Takagi et al. |
| 4,994,373 | A | 2/1991 | Stavrianopoulos et al. |
| 4,997,772 | A | 3/1991 | Sutton et al. |
| 5,001,417 | A | 3/1991 | Pumphrey et al. |
| 5,004,583 | A | 4/1991 | Guruswamy et al. |
| 5,048,554 | A | 9/1991 | Kremer |
| 5,053,199 | A | 10/1991 | Keiser et al. |
| 5,060,823 | A | 10/1991 | Perlman |
| 5,061,336 | A | 10/1991 | Soane |
| 5,064,618 | A | 11/1991 | Baker et al. |
| 5,071,531 | A | 12/1991 | Soane |
| 5,089,233 | A | 2/1992 | DeVaney, Jr. et al. |
| 5,091,328 | A | 2/1992 | Miller |
| D324,426 | S | 3/1992 | Fan et al. |
| 5,096,669 | A | 3/1992 | Lauks et al. |
| 5,098,663 | A | 3/1992 | Berthold et al. |
| D325,638 | S | 4/1992 | Sloat et al. |
| 5,126,002 | A | 6/1992 | Iwata et al. |
| 5,126,022 | A | 6/1992 | Soane et al. |
| D328,135 | S | 7/1992 | Fan et al. |
| D328,794 | S | 8/1992 | Frenkel et al. |
| 5,135,627 | A | 8/1992 | Soane |
| 5,135,872 | A | 8/1992 | Pouletty et al. |
| 5,147,606 | A | 9/1992 | Charlton et al. |
| 5,147,777 | A | 9/1992 | Sutton et al. |
| 5,155,166 | A | 10/1992 | Danielson et al. |
| 5,169,512 | A | 12/1992 | Wiedenmann et al. |
| 5,173,269 | A | 12/1992 | Mon et al. |
| D333,522 | S | 2/1993 | Gianino |
| 5,186,339 | A | 2/1993 | Heissler |
| 5,192,507 | A | 3/1993 | Taylor et al. |
| 5,208,163 | A | 5/1993 | Charlton et al. |
| 5,217,694 | A | 6/1993 | Gibler et al. |
| 5,223,226 | A | 6/1993 | Wittmer et al. |
| 5,229,297 | A | 7/1993 | Schnipelsky et al. |
| 5,231,015 | A | 7/1993 | Cummins et al. |
| D338,275 | S | 8/1993 | Fischer et al. |
| 5,234,809 | A | 8/1993 | Boom et al. |
| 5,250,263 | A | 10/1993 | Manz |
| 5,252,743 | A | 10/1993 | Barrett et al. |
| 5,256,376 | A | 10/1993 | Callan et al. |
| 5,273,716 | A | 12/1993 | Northrup et al. |
| 5,275,787 | A | 1/1994 | Yuguchi et al. |
| 5,282,950 | A | 2/1994 | Dietze et al. |
| 5,296,375 | A | 3/1994 | Kricka et al. |
| 5,304,477 | A | 4/1994 | Nagoh et al. |
| 5,304,487 | A | 4/1994 | Wilding et al. |
| D347,478 | S | 5/1994 | Pinkney |
| 5,311,896 | A | 5/1994 | Kaartinen et al. |
| 5,311,996 | A | 5/1994 | Duffy et al. |
| 5,316,727 | A | 5/1994 | Suzuki et al. |
| 5,327,038 | A | 7/1994 | Culp |
| 5,334,499 | A | 8/1994 | Burdick et al. |
| 5,338,671 | A | 8/1994 | Scalice et al. |
| 5,339,486 | A | 8/1994 | Persic, Jr. |
| D351,475 | S | 10/1994 | Gerber |
| D351,913 | S | 10/1994 | Hieb et al. |
| 5,364,591 | A | 11/1994 | Green et al. |
| 5,372,946 | A | 12/1994 | Cusak et al. |
| 5,374,395 | A | 12/1994 | Robinson |
| 5,384,499 | A | 1/1995 | Pedersen et al. |
| 5,389,339 | A | 2/1995 | Petschek et al. |
| D356,232 | S | 3/1995 | Armstrong et al. |
| 5,397,709 | A | 3/1995 | Berndt |
| 5,401,465 | A | 3/1995 | Smethers et al. |
| 5,411,708 | A | 5/1995 | Moscetta et al. |
| 5,414,245 | A | 5/1995 | Hackleman |
| 5,415,839 | A | 5/1995 | Zaun et al. |
| 5,416,000 | A | 5/1995 | Allen et al. |
| 5,422,271 | A | 6/1995 | Chen et al. |
| 5,422,284 | A | 6/1995 | Lau |
| 5,427,946 | A | 6/1995 | Kricka et al. |
| 5,443,791 | A | 8/1995 | Cathcart et al. |
| 5,466,574 | A | 11/1995 | Liberti et al. |
| 5,474,796 | A | 12/1995 | Brennan |
| 5,475,487 | A | 12/1995 | Mariella, Jr. et al. |
| D366,116 | S | 1/1996 | Biskupski |
| 5,486,335 | A | 1/1996 | Wilding et al. |
| 5,494,639 | A | 2/1996 | Grzegorzewski |
| 5,498,392 | A | 3/1996 | Wilding et al. |
| 5,503,803 | A | 4/1996 | Brown |
| 5,516,410 | A | 5/1996 | Schneider et al. |
| 5,519,635 | A | 5/1996 | Miyake et al. |
| 5,529,677 | A | 6/1996 | Schneider et al. |
| 5,559,432 | A | 9/1996 | Logue |
| 5,565,171 | A | 10/1996 | Dovichi et al. |
| 5,569,364 | A | 10/1996 | Hooper et al. |
| 5,576,218 | A | 11/1996 | Zurek et al. |
| 5,578,270 | A | 11/1996 | Reichler et al. |
| 5,578,818 | A | 11/1996 | Kain et al. |
| 5,579,928 | A | 12/1996 | Anukwuem |
| 5,580,523 | A | 12/1996 | Bard |
| 5,582,884 | A | 12/1996 | Ball et al. |

(56) References Cited

U.S. PATENT DOCUMENTS

| | | | |
|---|---|---|---|
| 5,582,988 | A | 12/1996 | Backus et al. |
| 5,585,069 | A | 12/1996 | Zanucchi et al. |
| 5,585,089 | A | 12/1996 | Queen et al. |
| 5,585,242 | A | 12/1996 | Bouma et al. |
| 5,587,128 | A | 12/1996 | Wilding et al. |
| 5,589,136 | A | 12/1996 | Northrup et al. |
| 5,593,838 | A | 1/1997 | Zanzucchi et al. |
| 5,595,708 | A | 1/1997 | Berndt |
| 5,599,432 | A | 2/1997 | Manz et al. |
| 5,599,503 | A | 2/1997 | Manz et al. |
| 5,599,667 | A | 2/1997 | Arnold, Jr. et al. |
| 5,601,727 | A | 2/1997 | Bormann et al. |
| 5,603,351 | A | 2/1997 | Cherukuri et al. |
| 5,605,662 | A | 2/1997 | Heller et al. |
| 5,609,910 | A | 3/1997 | Hackleman |
| D378,782 | S | 4/1997 | LaBarbera et al. |
| 5,628,890 | A | 5/1997 | Carter et al. |
| 5,630,920 | A | 5/1997 | Friese et al. |
| 5,631,337 | A | 5/1997 | Sassi et al. |
| 5,632,876 | A | 5/1997 | Zanzucchi et al. |
| 5,632,957 | A | 5/1997 | Heller et al. |
| 5,635,358 | A | 6/1997 | Wilding et al. |
| 5,637,469 | A | 6/1997 | Wilding et al. |
| 5,639,423 | A | 6/1997 | Northrup et al. |
| 5,639,428 | A | 6/1997 | Cottingham |
| 5,643,738 | A | 7/1997 | Zanzucchi et al. |
| 5,645,801 | A | 7/1997 | Bouma et al. |
| 5,646,039 | A | 7/1997 | Northrup et al. |
| 5,646,049 | A | 7/1997 | Tayi |
| 5,647,994 | A | 7/1997 | Tuunanen et al. |
| 5,651,839 | A | 7/1997 | Rauf |
| 5,652,141 | A | 7/1997 | Henco et al. |
| 5,652,149 | A | 7/1997 | Mileaf et al. |
| D382,346 | S | 8/1997 | Buhler et al. |
| D382,647 | S | 8/1997 | Staples et al. |
| 5,654,141 | A | 8/1997 | Mariani et al. |
| 5,658,515 | A | 8/1997 | Lee et al. |
| 5,667,976 | A | 9/1997 | Van Ness et al. |
| 5,671,303 | A | 9/1997 | Shieh et al. |
| 5,674,394 | A | 10/1997 | Whitmore |
| 5,674,742 | A | 10/1997 | Northrup et al. |
| 5,681,484 | A | 10/1997 | Zanzucchi et al. |
| 5,681,529 | A | 10/1997 | Taguchi et al. |
| 5,683,657 | A | 11/1997 | Mian |
| 5,683,659 | A | 11/1997 | Hovatter |
| 5,699,157 | A | 12/1997 | Parce et al. |
| 5,700,429 | A | 12/1997 | Bühler et al. |
| 5,700,637 | A | 12/1997 | Southern |
| 5,705,610 | A | 1/1998 | Zuckermann et al. |
| 5,705,813 | A | 1/1998 | Apffel et al. |
| 5,720,923 | A | 2/1998 | Haff et al. |
| 5,721,136 | A | 2/1998 | Finney et al. |
| 5,725,831 | A | 3/1998 | Reichler et al. |
| 5,726,026 | A | 3/1998 | Wilding et al. |
| 5,726,404 | A | 3/1998 | Brody |
| 5,726,944 | A | 3/1998 | Pelley et al. |
| 5,731,212 | A | 3/1998 | Gavin et al. |
| 5,744,366 | A | 4/1998 | Kricka et al. |
| 5,746,978 | A | 5/1998 | Bienhaus et al. |
| 5,747,666 | A | 5/1998 | Willis |
| 5,750,015 | A | 5/1998 | Soane et al. |
| 5,755,942 | A | 5/1998 | Zanzucchi et al. |
| 5,762,874 | A | 6/1998 | Seaton et al. |
| 5,763,262 | A | 6/1998 | Wong et al. |
| 5,770,029 | A | 6/1998 | Nelson et al. |
| 5,770,388 | A | 6/1998 | Vorpahl |
| 5,772,966 | A | 6/1998 | Maracas et al. |
| 5,779,868 | A | 7/1998 | Parce et al. |
| 5,783,148 | A | 7/1998 | Cottingham et al. |
| 5,787,032 | A | 7/1998 | Heller et al. |
| 5,788,814 | A | 8/1998 | Sun et al. |
| 5,800,600 | A | 9/1998 | Lima-Marques et al. |
| 5,800,690 | A | 9/1998 | Chow et al. |
| 5,804,436 | A | 9/1998 | Okun et al. |
| D399,959 | S | 10/1998 | Prokop et al. |
| 5,819,749 | A | 10/1998 | Lee et al. |
| 5,827,481 | A | 10/1998 | Bente et al. |
| 5,842,106 | A | 11/1998 | Thaler et al. |
| 5,842,787 | A | 12/1998 | Kopf-Sill et al. |
| 5,846,396 | A | 12/1998 | Zanzucchi et al. |
| 5,846,493 | A | 12/1998 | Bankier et al. |
| 5,849,208 | A | 12/1998 | Hayes et al. |
| 5,849,486 | A | 12/1998 | Heller et al. |
| 5,849,489 | A | 12/1998 | Heller |
| 5,849,598 | A | 12/1998 | Wilson et al. |
| 5,851,492 | A | 12/1998 | Blattner |
| 5,852,495 | A | 12/1998 | Parce |
| 5,856,174 | A | 1/1999 | Lipshutz et al. |
| 5,858,187 | A | 1/1999 | Ramsey et al. |
| 5,858,188 | A | 1/1999 | Soane et al. |
| 5,863,502 | A | 1/1999 | Southgate et al. |
| 5,863,708 | A | 1/1999 | Zanzucchi et al. |
| 5,863,801 | A | 1/1999 | Southgate et al. |
| 5,866,345 | A | 2/1999 | Wilding et al. |
| 5,869,004 | A | 2/1999 | Parce et al. |
| 5,869,244 | A | 2/1999 | Martin et al. |
| 5,872,010 | A | 2/1999 | Karger et al. |
| 5,872,623 | A | 2/1999 | Stabile et al. |
| 5,874,046 | A | 2/1999 | Megerle |
| 5,876,675 | A | 3/1999 | Kennedy |
| 5,880,071 | A | 3/1999 | Parce et al. |
| 5,882,465 | A | 3/1999 | McReynolds |
| 5,883,211 | A | 3/1999 | Sassi et al. |
| 5,885,432 | A | 3/1999 | Hooper et al. |
| 5,885,470 | A | 3/1999 | Parce et al. |
| 5,895,762 | A | 4/1999 | Greenfield et al. |
| 5,900,130 | A | 5/1999 | Benvegnu et al. |
| 5,911,737 | A | 6/1999 | Lee et al. |
| 5,912,124 | A | 6/1999 | Kumar |
| 5,912,134 | A | 6/1999 | Shartle |
| 5,914,229 | A | 6/1999 | Loewy |
| 5,916,522 | A | 6/1999 | Boyd et al. |
| 5,916,776 | A | 6/1999 | Kumar |
| 5,919,646 | A | 7/1999 | Okun et al. |
| 5,919,711 | A | 7/1999 | Boyd et al. |
| 5,922,289 | A | 7/1999 | Wong |
| 5,922,591 | A | 7/1999 | Anderson et al. |
| 5,927,547 | A | 7/1999 | Papen et al. |
| 5,928,161 | A | 7/1999 | Krulevitch et al. |
| 5,928,880 | A | 7/1999 | Wilding et al. |
| 5,929,208 | A | 7/1999 | Heller et al. |
| D413,391 | S | 8/1999 | Lapeus et al. |
| 5,932,799 | A | 8/1999 | Moles |
| 5,935,401 | A | 8/1999 | Amigo |
| 5,935,522 | A | 8/1999 | Swerdlow et al. |
| 5,939,291 | A | 8/1999 | Loewy et al. |
| 5,939,312 | A | 8/1999 | Baier et al. |
| 5,942,443 | A | 8/1999 | Parce et al. |
| 5,944,717 | A | 8/1999 | Lee et al. |
| D413,677 | S | 9/1999 | Dumitrescu et al. |
| D414,271 | S | 9/1999 | Mendoza |
| 5,948,227 | A | 9/1999 | Dubrow |
| 5,948,363 | A | 9/1999 | Gaillard |
| 5,948,673 | A | 9/1999 | Cottingham |
| 5,955,028 | A | 9/1999 | Chow |
| 5,955,029 | A | 9/1999 | Wilding et al. |
| 5,957,579 | A | 9/1999 | Kopf-Sill et al. |
| 5,958,203 | A | 9/1999 | Parce et al. |
| 5,958,349 | A | 9/1999 | Petersen et al. |
| 5,958,694 | A | 9/1999 | Nikiforov |
| 5,959,221 | A | 9/1999 | Boyd et al. |
| 5,959,291 | A | 9/1999 | Jensen |
| 5,964,995 | A | 10/1999 | Nikiforov et al. |
| 5,964,997 | A | 10/1999 | McBride |
| 5,965,001 | A | 10/1999 | Chow et al. |
| 5,965,410 | A | 10/1999 | Chow et al. |
| 5,965,886 | A | 10/1999 | Sauer et al. |
| 5,968,745 | A | 10/1999 | Thorp et al. |
| 5,972,187 | A | 10/1999 | Parce et al. |
| 5,973,138 | A | 10/1999 | Collis |
| D417,009 | S | 11/1999 | Boyd |
| 5,976,336 | A | 11/1999 | Dubrow et al. |
| 5,980,704 | A | 11/1999 | Cherukuri et al. |
| 5,980,719 | A | 11/1999 | Cherukuri et al. |

(56) References Cited

U.S. PATENT DOCUMENTS

| | | | |
|---|---|---|---|
| 5,981,735 | A | 11/1999 | Thatcher et al. |
| 5,985,651 | A | 11/1999 | Hunicke-Smith |
| 5,989,402 | A | 11/1999 | Chow et al. |
| 5,992,820 | A | 11/1999 | Fare et al. |
| 5,993,611 | A | 11/1999 | Moroney et al. |
| 5,993,750 | A | 11/1999 | Ghosh et al. |
| 5,997,708 | A | 12/1999 | Craig |
| 6,001,229 | A | 12/1999 | Ramsey |
| 6,001,231 | A | 12/1999 | Kopf-Sill |
| 6,001,307 | A | 12/1999 | Naka et al. |
| 6,004,450 | A | 12/1999 | Northrup et al. |
| 6,004,515 | A | 12/1999 | Parce et al. |
| 6,007,690 | A | 12/1999 | Nelson et al. |
| 6,010,607 | A | 1/2000 | Ramsey |
| 6,010,608 | A | 1/2000 | Ramsey |
| 6,010,627 | A | 1/2000 | Hood, III |
| 6,012,902 | A | 1/2000 | Parce |
| D420,747 | S | 2/2000 | Dumitrescu et al. |
| D421,130 | S | 2/2000 | Cohen et al. |
| 6,024,920 | A | 2/2000 | Cunanan |
| D421,653 | S | 3/2000 | Purcell |
| 6,033,546 | A | 3/2000 | Ramsey |
| 6,033,880 | A | 3/2000 | Haff et al. |
| 6,043,080 | A | 3/2000 | Lipshutz et al. |
| 6,043,880 | A | 3/2000 | Andrews et al. |
| 6,046,056 | A | 4/2000 | Parce et al. |
| 6,048,734 | A | 4/2000 | Burns et al. |
| 6,054,034 | A | 4/2000 | Soane et al. |
| 6,054,277 | A | 4/2000 | Furcht et al. |
| 6,056,860 | A | 5/2000 | Amigo et al. |
| 6,057,149 | A | 5/2000 | Burns et al. |
| 6,062,261 | A | 5/2000 | Jacobson et al. |
| 6,063,341 | A | 5/2000 | Fassbind et al. |
| 6,063,589 | A | 5/2000 | Kellogg et al. |
| 6,066,300 | A | 5/2000 | Carey et al. |
| 6,068,751 | A | 5/2000 | Neukermans |
| 6,068,752 | A | 5/2000 | Dubrow et al. |
| 6,071,478 | A | 6/2000 | Chow |
| 6,074,725 | A | 6/2000 | Kennedy |
| 6,074,827 | A | 6/2000 | Nelson et al. |
| D428,497 | S | 7/2000 | Lapeus et al. |
| 6,086,740 | A | 7/2000 | Kennedy |
| 6,096,509 | A | 8/2000 | Okun et al. |
| 6,100,541 | A | 8/2000 | Nagle et al. |
| 6,102,897 | A | 8/2000 | Lang |
| 6,103,537 | A | 8/2000 | Ullman et al. |
| 6,106,685 | A | 8/2000 | McBride et al. |
| 6,110,343 | A | 8/2000 | Ramsey et al. |
| 6,117,398 | A | 9/2000 | Bienhaus et al. |
| 6,123,205 | A | 9/2000 | Dumitrescu et al. |
| 6,123,798 | A | 9/2000 | Gandhi et al. |
| 6,130,098 | A | 10/2000 | Handique et al. |
| 6,132,580 | A | 10/2000 | Mathies et al. |
| 6,132,684 | A | 10/2000 | Marino |
| 6,133,436 | A | 10/2000 | Koster et al. |
| D433,759 | S | 11/2000 | Mathis et al. |
| 6,143,250 | A | 11/2000 | Tajima |
| 6,143,547 | A | 11/2000 | Hsu |
| 6,149,787 | A | 11/2000 | Chow et al. |
| 6,149,872 | A | 11/2000 | Mack et al. |
| 6,156,199 | A | 12/2000 | Zuk, Jr. |
| 6,158,269 | A | 12/2000 | Dorenkott et al. |
| 6,167,910 | B1 | 1/2001 | Chow |
| 6,168,948 | B1 | 1/2001 | Anderson et al. |
| 6,171,850 | B1 | 1/2001 | Nagle et al. |
| 6,174,675 | B1 | 1/2001 | Chow et al. |
| 6,180,950 | B1 | 1/2001 | Olsen |
| D438,311 | S | 2/2001 | Yamanishi et al. |
| 6,190,619 | B1 | 2/2001 | Kilcoin et al. |
| 6,194,563 | B1 | 2/2001 | Cruickshank |
| D438,632 | S | 3/2001 | Miller |
| D438,633 | S | 3/2001 | Miller |
| D439,673 | S | 3/2001 | Brophy et al. |
| 6,197,595 | B1 | 3/2001 | Anderson et al. |
| 6,203,759 | B1 | 3/2001 | Pelc et al. |
| 6,211,989 | B1 | 4/2001 | Wulf et al. |
| 6,213,151 | B1 | 4/2001 | Jacobson et al. |
| 6,221,600 | B1 | 4/2001 | Macleod et al. |
| 6,228,635 | B1 | 5/2001 | Armstrong et al. |
| 6,232,072 | B1 | 5/2001 | Fisher |
| 6,235,175 | B1 | 5/2001 | Dubrow et al. |
| 6,235,313 | B1 | 5/2001 | Mathiowitz et al. |
| 6,235,471 | B1 | 5/2001 | Knapp et al. |
| 6,236,456 | B1 | 5/2001 | Giebeler et al. |
| 6,236,581 | B1 | 5/2001 | Foss et al. |
| 6,238,626 | B1 | 5/2001 | Higuchi et al. |
| 6,251,343 | B1 | 6/2001 | Dubrow et al. |
| 6,254,826 | B1 | 7/2001 | Acosta et al. |
| 6,259,635 | B1 | 7/2001 | Khouri et al. |
| 6,261,431 | B1 | 7/2001 | Mathies et al. |
| 6,267,858 | B1 | 7/2001 | Parce et al. |
| D446,306 | S | 8/2001 | Ochi et al. |
| 6,271,021 | B1 | 8/2001 | Burns et al. |
| 6,274,089 | B1 | 8/2001 | Chow et al. |
| 6,280,967 | B1 | 8/2001 | Ransom et al. |
| 6,281,008 | B1 | 8/2001 | Komai et al. |
| 6,284,113 | B1 | 9/2001 | Bjornson et al. |
| 6,284,470 | B1 | 9/2001 | Bitner et al. |
| 6,287,254 | B1 | 9/2001 | Dodds |
| 6,287,774 | B1 | 9/2001 | Nikiforov |
| 6,291,248 | B1 | 9/2001 | Haj-Ahmad |
| 6,294,063 | B1 | 9/2001 | Becker et al. |
| 6,300,124 | B1 | 10/2001 | Blumenfeld et al. |
| 6,302,134 | B1 | 10/2001 | Kellogg et al. |
| 6,302,304 | B1 | 10/2001 | Spencer |
| 6,303,343 | B1 | 10/2001 | Kopf-sill |
| 6,306,273 | B1 | 10/2001 | Wainright et al. |
| 6,306,590 | B1 | 10/2001 | Mehta et al. |
| 6,310,199 | B1 | 10/2001 | Smith et al. |
| 6,316,774 | B1 | 11/2001 | Giebeler et al. |
| 6,319,469 | B1 | 11/2001 | Mian et al. |
| 6,319,474 | B1 | 11/2001 | Krulevitch et al. |
| 6,322,683 | B1 | 11/2001 | Wolk et al. |
| 6,326,083 | B1 | 12/2001 | Yang et al. |
| 6,326,147 | B1 * | 12/2001 | Oldham ............. G01N 35/0092 422/50 |
| 6,326,211 | B1 | 12/2001 | Anderson et al. |
| 6,334,980 | B1 | 1/2002 | Hayes et al. |
| 6,337,435 | B1 | 1/2002 | Chu et al. |
| 6,352,673 | B1 | 3/2002 | Rainin et al. |
| 6,353,475 | B1 | 3/2002 | Jensen et al. |
| 6,358,387 | B1 | 3/2002 | Kopf-sill et al. |
| 6,366,924 | B1 | 4/2002 | Parce |
| 6,368,561 | B1 | 4/2002 | Rutishauser et al. |
| 6,368,871 | B1 | 4/2002 | Christel et al. |
| 6,370,206 | B1 | 4/2002 | Schenk |
| 6,375,185 | B1 | 4/2002 | Lin |
| 6,375,901 | B1 | 4/2002 | Robotti et al. |
| 6,379,884 | B2 | 4/2002 | Wada et al. |
| 6,379,929 | B1 | 4/2002 | Burns et al. |
| 6,379,974 | B1 | 4/2002 | Parce et al. |
| 6,382,254 | B1 | 5/2002 | Yang et al. |
| 6,391,541 | B1 | 5/2002 | Petersen et al. |
| 6,391,623 | B1 | 5/2002 | Besemer et al. |
| 6,395,161 | B1 | 5/2002 | Schneider et al. |
| 6,398,956 | B1 | 6/2002 | Coville et al. |
| 6,399,025 | B1 | 6/2002 | Chow |
| 6,399,389 | B1 | 6/2002 | Parce et al. |
| 6,399,952 | B1 | 6/2002 | Maher et al. |
| 6,401,552 | B1 | 6/2002 | Elkins |
| 6,403,338 | B1 | 6/2002 | Knapp et al. |
| 6,408,878 | B2 | 6/2002 | Unger et al. |
| 6,413,401 | B1 | 7/2002 | Chow et al. |
| 6,416,642 | B1 | 7/2002 | Alajoki et al. |
| 6,420,143 | B1 | 7/2002 | Kopf-sill |
| 6,425,972 | B1 | 7/2002 | McReynolds |
| D461,906 | S | 8/2002 | Pham |
| 6,428,987 | B2 | 8/2002 | Franzen |
| 6,430,512 | B1 | 8/2002 | Gallagher |
| 6,432,366 | B2 | 8/2002 | Ruediger et al. |
| 6,440,725 | B1 | 8/2002 | Pourahmadi et al. |
| D463,031 | S | 9/2002 | Slomski et al. |
| 6,444,461 | B1 | 9/2002 | Knapp et al. |
| 6,447,661 | B1 | 9/2002 | Chow et al. |

(56) References Cited

U.S. PATENT DOCUMENTS 6,447,727 B1 9/2002 Parce et al.
6,448,047 B2 9/2002 Dattagupta et al.
6,448,064 B1 9/2002 Vo-Dinh et al.
6,453,928 B1 9/2002 Kaplan et al.
6,458,259 B1 10/2002 Parce et al.
6,461,570 B2 10/2002 Ishihara et al.
6,465,257 B1 10/2002 Parce et al.
6,468,761 B2 10/2002 Yang et al.
6,472,141 B2 10/2002 Nikiforov
D466,219 S 11/2002 Wynschenk et al.
6,475,364 B1 11/2002 Dubrow et al.
D467,348 S 12/2002 McMichael et al.
D467,349 S 12/2002 Niedbala et al.
6,488,897 B2 12/2002 Dubrow et al.
6,495,104 B1 12/2002 Unno et al.
6,498,497 B1 12/2002 Chow et al.
6,500,323 B1 12/2002 Chow et al.
6,500,390 B1 12/2002 Boulton et al.
D468,437 S 1/2003 McMenamy et al.
6,506,609 B1 1/2003 Wada et al.
6,509,186 B1 1/2003 Zou et al.
6,509,193 B1 1/2003 Tajima
6,511,853 B1 1/2003 Kopf-sill et al.
D470,595 S 2/2003 Crisanti et al.
6,515,753 B2 2/2003 Maher
6,517,783 B2 2/2003 Horner et al.
6,520,197 B2 2/2003 Deshmukh et al.
6,521,181 B1 2/2003 Northrup et al.
6,521,188 B1 2/2003 Webster
6,524,456 B1 2/2003 Ramsey et al.
6,524,532 B1 2/2003 Northrup
6,524,790 B1 2/2003 Kopf-sill et al.
D472,324 S 3/2003 Rumore et al.
6,534,295 B2 3/2003 Tai et al.
6,537,432 B1 3/2003 Schneider et al.
6,537,771 B1 3/2003 Farinas et al.
6,540,896 B1 4/2003 Manz et al.
6,544,734 B1 4/2003 Briscoe et al.
6,547,942 B1 4/2003 Parce et al.
6,555,389 B1 4/2003 Ullman et al.
6,556,923 B2 4/2003 Gallagher et al.
D474,279 S 5/2003 Mayer et al.
D474,280 S 5/2003 Niedbala et al.
6,558,916 B2 5/2003 Veerapandian et al.
6,558,945 B1 5/2003 Kao
6,565,815 B1 5/2003 Chang et al.
6,569,607 B2 5/2003 McReynolds
6,572,830 B1 6/2003 Burdon et al.
6,575,188 B2 6/2003 Parunak
6,576,459 B2 6/2003 Miles et al.
6,579,453 B1 6/2003 Bächler et al.
6,589,729 B2 7/2003 Chan et al.
6,592,821 B1 7/2003 Wada et al.
6,597,450 B1 7/2003 Andrews et al.
6,602,474 B1 8/2003 Tajima
6,605,475 B1 8/2003 Taylor et al.
6,613,211 B1 9/2003 Mccormick et al.
6,613,512 B1 9/2003 Kopf-sill et al.
6,613,580 B1 9/2003 Chow et al.
6,613,581 B1 9/2003 Wada et al.
6,614,030 B2 9/2003 Maher et al.
6,620,625 B2 9/2003 Wolk et al.
6,623,860 B2 9/2003 Hu et al.
6,627,406 B1 9/2003 Singh et al.
D480,814 S 10/2003 Lafferty et al.
6,632,655 B1 10/2003 Mehta et al.
6,633,785 B1 10/2003 Kasahara et al.
D482,796 S 11/2003 Oyama et al.
6,640,981 B2 11/2003 Lafond et al.
6,649,358 B1 11/2003 Parce et al.
6,664,104 B2 12/2003 Pourahmadi et al.
6,669,831 B2 12/2003 Chow et al.
6,670,133 B2 12/2003 Knapp et al.
6,670,153 B2 12/2003 Stern
D484,989 S 1/2004 Gebrian
6,672,458 B2 1/2004 Hansen et al.
6,679,279 B1 1/2004 Lui et al.
6,681,616 B2 1/2004 Spaid et al.
6,681,788 B2 1/2004 Parce et al.
6,685,813 B2 2/2004 Williams et al.
6,692,700 B2 2/2004 Handique
6,695,009 B2 2/2004 Chien et al.
6,699,713 B2 3/2004 Benett et al.
6,706,519 B1 3/2004 Kellogg et al.
6,720,148 B1 4/2004 Nikiforov
6,730,206 B2 5/2004 Ricco et al.
6,733,645 B1 5/2004 Chow
6,734,401 B2 5/2004 Bedingham et al.
6,737,026 B1 5/2004 Bergh et al.
6,740,518 B1 5/2004 Duong et al.
D491,272 S 6/2004 Alden et al.
D491,273 S 6/2004 Biegler et al.
D491,276 S 6/2004 Langille
6,750,661 B2 6/2004 Brooks et al.
6,752,966 B1 6/2004 Chazan
6,756,019 B1 6/2004 Dubrow et al.
6,762,049 B2 7/2004 Zou et al.
6,764,859 B1 7/2004 Kreuwel et al.
6,766,817 B2 7/2004 Dias da Silva
6,773,567 B1 8/2004 Wolk
6,777,184 B2 8/2004 Nikiforov et al.
6,783,962 B1 8/2004 Olander et al.
D495,805 S 9/2004 Lea et al.
6,787,015 B2 9/2004 Lackritz et al.
6,787,016 B2 9/2004 Tan et al.
6,787,111 B2 9/2004 Roach et al.
6,790,328 B2 9/2004 Jacobson et al.
6,790,330 B2 9/2004 Gascoyne et al.
6,811,668 B1 11/2004 Berndt et al.
6,818,113 B2 11/2004 Williams et al.
6,819,027 B2 11/2004 Saraf
6,824,663 B1 11/2004 Boone
D499,813 S 12/2004 Wu
D500,142 S 12/2004 Crisanti et al.
D500,363 S 12/2004 Fanning et al.
6,827,831 B1 12/2004 Chow et al.
6,827,906 B1 12/2004 Björnson et al.
6,838,156 B1 1/2005 Neyer et al.
6,838,680 B2 1/2005 Maher et al.
6,852,287 B2 2/2005 Ganesan
6,858,185 B1 2/2005 Kopf-sill et al.
6,859,698 B2 2/2005 Schmeisser
6,861,035 B2 3/2005 Pham et al.
6,878,540 B2 4/2005 Pourahmadi et al.
6,878,755 B2 4/2005 Singh et al.
6,884,628 B2 4/2005 Hubbell et al.
6,887,693 B2 5/2005 McMillan et al.
6,893,879 B2 5/2005 Petersen et al.
6,900,889 B2 5/2005 Bjornson et al.
6,905,583 B2 6/2005 Wainright et al.
6,905,612 B2 6/2005 Dorian et al.
6,906,797 B1 6/2005 Kao et al.
6,908,594 B1 6/2005 Schaevitz et al.
6,911,183 B1 6/2005 Handique et al.
6,914,137 B2 7/2005 Baker
6,915,679 B2 7/2005 Chien et al.
6,918,404 B2 7/2005 Dias da Silva
D508,999 S 8/2005 Fanning et al.
6,939,451 B2 9/2005 Zhao et al.
6,940,598 B2 9/2005 Christel et al.
6,942,771 B1 9/2005 Kayyem
6,951,632 B2 10/2005 Unger et al.
6,958,392 B2 10/2005 Fomovskaia et al.
D512,155 S 11/2005 Matsumoto
6,964,747 B2 11/2005 Banerjee et al.
6,969,835 B1 11/2005 Rushbrooke et al.
6,977,163 B1 12/2005 Mehta
6,979,424 B2 12/2005 Northrup et al.
6,984,516 B2 1/2006 Briscoe et al.
D515,707 S 2/2006 Sinohara et al.
D516,221 S 2/2006 Wohlstadter et al.
7,001,853 B1 2/2006 Brown et al.
7,004,184 B2 2/2006 Handique et al.
D517,554 S 3/2006 Yanagisawa et al.

(56) References Cited

U.S. PATENT DOCUMENTS 7,010,391 B2 3/2006 Handique et al.
7,023,007 B2 4/2006 Gallagher
7,024,281 B1 4/2006 Unno
7,036,667 B2 5/2006 Greenstein et al.
7,037,416 B2 5/2006 Parce et al.
7,038,472 B1 5/2006 Chien
7,039,527 B2 5/2006 Tripathi et al.
7,040,144 B2 5/2006 Spaid et al.
7,041,258 B2 5/2006 Desmond et al.
7,049,558 B2 5/2006 Baer et al.
D523,153 S 6/2006 Akashi et al.
7,055,695 B2 6/2006 Greenstein et al.
7,060,171 B1 6/2006 Nikiforov et al.
7,066,586 B2 6/2006 Dias da Silva
7,069,952 B1 7/2006 McReynolds et al.
7,072,036 B2 7/2006 Jones et al.
7,099,778 B2 8/2006 Chien
D528,215 S 9/2006 Malmsater
7,101,467 B2 9/2006 Spaid
7,105,304 B1 9/2006 Nikiforov et al.
D531,321 S 10/2006 Godfrey et al.
7,118,892 B2 10/2006 Ammann et al.
7,118,910 B2 10/2006 Unger et al.
7,122,799 B2 10/2006 Hsieh et al.
7,135,144 B2 11/2006 Christel et al.
7,138,032 B2 11/2006 Gandhi et al.
D534,280 S 12/2006 Gomm et al.
7,150,814 B1 12/2006 Parce et al.
7,150,999 B1 12/2006 Shuck
D535,403 S 1/2007 Isozaki et al.
7,160,423 B2 1/2007 Chien et al.
7,161,356 B1 1/2007 Chien
7,169,277 B2 1/2007 Ausserer et al.
7,169,601 B1 1/2007 Northrup et al.
7,169,618 B2 1/2007 Skold
D537,951 S 3/2007 Okamoto et al.
D538,436 S 3/2007 Patadia et al.
7,188,001 B2 3/2007 Young et al.
7,192,557 B2 3/2007 Wu et al.
7,195,986 B1 3/2007 Bousse et al.
7,205,154 B2 4/2007 Corson
7,208,125 B1 4/2007 Dong
7,235,406 B1 6/2007 Woudenberg et al.
7,247,274 B1 7/2007 Chow
D548,841 S 8/2007 Brownell et al.
D549,827 S 8/2007 Maeno et al.
7,252,928 B1 8/2007 Hafeman et al.
7,255,833 B2 8/2007 Chang et al.
7,270,786 B2 9/2007 Parunak et al.
D554,069 S 10/2007 Bolotin et al.
D554,070 S 10/2007 Bolotin et al.
7,276,208 B2 10/2007 Sevigny et al.
7,276,330 B2 10/2007 Chow et al.
7,288,228 B2 10/2007 Lefebvre
7,297,313 B1 11/2007 Northrup et al.
D556,914 S 12/2007 Okamoto et al.
7,303,727 B1 12/2007 Dubrow et al.
D559,995 S 1/2008 Handique et al.
7,315,376 B2 1/2008 Bickmore et al.
7,323,140 B2 1/2008 Handique et al.
7,332,130 B2 2/2008 Handique
7,338,760 B2 3/2008 Gong et al.
D566,291 S 4/2008 Parunak et al.
7,351,377 B2 4/2008 Chazan et al.
D569,526 S 5/2008 Duffy et al.
7,374,949 B2 5/2008 Kuriger
7,390,460 B2 6/2008 Osawa et al.
7,419,784 B2 9/2008 Dubrow et al.
7,422,669 B2 9/2008 Jacobson et al.
7,440,684 B2 10/2008 Spaid et al.
7,476,313 B2 1/2009 Siddiqi
7,480,042 B1 1/2009 Phillips et al.
7,494,577 B2 2/2009 Williams et al.
7,494,770 B2 2/2009 Wilding et al.
7,514,046 B2 4/2009 Kechagia et al.
7,518,726 B2 4/2009 Rulison et al.
7,521,186 B2 4/2009 Burd Mehta
7,527,769 B2 5/2009 Bunch et al.
D595,423 S 6/2009 Johansson et al.
7,553,671 B2 6/2009 Sinclair et al.
D596,312 S 7/2009 Giraud et al.
D598,566 S 8/2009 Allaer
7,578,976 B1 8/2009 Northrup et al.
D599,234 S 9/2009 Ito
7,595,197 B2 9/2009 Brasseur
7,604,938 B2 10/2009 Takahashi et al.
7,622,296 B2 11/2009 Joseph et al.
7,628,902 B2 12/2009 Knowlton et al.
7,633,606 B2 12/2009 Northrup et al.
7,635,588 B2 12/2009 King et al.
7,645,581 B2 1/2010 Knapp et al.
7,670,559 B2 3/2010 Chien et al.
7,674,431 B2 3/2010 Ganesan
7,689,022 B2 3/2010 Weiner et al.
7,704,735 B2 4/2010 Facer et al.
7,705,739 B2 4/2010 Northrup et al.
7,723,123 B1 5/2010 Murphy et al.
D618,820 S 6/2010 Wilson et al.
7,727,371 B2 6/2010 Kennedy et al.
7,727,477 B2 6/2010 Boronkay et al.
7,744,817 B2 6/2010 Bui
D621,060 S 8/2010 Handique
7,785,868 B2 8/2010 Yuan et al.
D628,305 S 11/2010 Gorrec et al.
7,829,025 B2 11/2010 Ganesan et al.
7,858,366 B2 12/2010 Northrup et al.
7,867,776 B2 1/2011 Kennedy et al.
D632,799 S 2/2011 Canner et al.
7,892,819 B2 2/2011 Wilding et al.
D637,737 S 5/2011 Wilson et al.
7,955,864 B2 6/2011 Cox et al.
7,987,022 B2 7/2011 Handique et al.
7,998,708 B2 8/2011 Handique et al.
8,053,214 B2 11/2011 Northrup
8,071,056 B2 12/2011 Burns et al.
8,088,616 B2 1/2012 Handique
8,105,783 B2 1/2012 Handique
8,110,158 B2 2/2012 Handique
8,133,671 B2 3/2012 Williams et al.
8,182,763 B2 5/2012 Duffy et al.
8,232,900 B2 7/2012 Takeda
8,246,919 B2 8/2012 Herchenbach et al.
8,273,308 B2 9/2012 Handique et al.
D669,597 S 10/2012 Cavada et al.
8,287,820 B2 10/2012 Williams et al.
8,323,584 B2 12/2012 Ganesan
8,323,900 B2 12/2012 Handique et al.
8,324,372 B2 12/2012 Brahmasandra et al.
8,415,103 B2 4/2013 Handique
8,420,015 B2 4/2013 Ganesan et al.
8,440,149 B2 5/2013 Handique
8,470,586 B2 6/2013 Wu et al.
8,473,104 B2 6/2013 Handique et al.
D686,749 S 7/2013 Trump
D687,567 S 8/2013 Jungheim et al.
D692,162 S 10/2013 Lentz et al.
8,592,157 B2 11/2013 Petersen et al.
8,679,831 B2 3/2014 Handique et al.
D702,854 S 4/2014 Nakahana et al.
8,685,341 B2 4/2014 Ganesan
8,703,069 B2 4/2014 Handique et al.
8,709,787 B2 4/2014 Handique
8,710,211 B2 4/2014 Brahmasandra et al.
8,734,733 B2 5/2014 Handique
D710,024 S 7/2014 Guo
8,765,076 B2 7/2014 Handique et al.
8,765,454 B2 7/2014 Zhou et al.
8,768,517 B2 7/2014 Handique et al.
8,852,862 B2 10/2014 Wu et al.
8,883,490 B2 11/2014 Handique et al.
8,894,947 B2 11/2014 Ganesan et al.
8,895,311 B1 11/2014 Handique et al.
D729,404 S 5/2015 Teich et al.
9,028,773 B2 5/2015 Ganesan

(56) References Cited

U.S. PATENT DOCUMENTS

| | | | |
|---|---|---|---|
| 9,040,288 | B2 | 5/2015 | Handique et al. |
| 9,051,604 | B2 | 6/2015 | Handique |
| 9,080,207 | B2 | 7/2015 | Handique et al. |
| D742,027 | S | 10/2015 | Lentz et al. |
| 9,186,677 | B2 | 11/2015 | Williams et al. |
| 9,217,143 | B2 | 12/2015 | Brahmasandra et al. |
| 9,222,954 | B2 | 12/2015 | Lentz et al. |
| 9,234,236 | B2 | 1/2016 | Thomas et al. |
| 9,238,223 | B2 | 1/2016 | Handique |
| 9,259,734 | B2 | 2/2016 | Williams et al. |
| 9,259,735 | B2 | 2/2016 | Handique et al. |
| 9,347,586 | B2 | 5/2016 | Williams et al. |
| 9,382,532 | B2 | 7/2016 | Brahmasandra et al. |
| 9,480,983 | B2 | 11/2016 | Lentz et al. |
| 9,528,142 | B2 | 12/2016 | Handique |
| 9,618,139 | B2 | 4/2017 | Handique |
| D787,087 | S | 5/2017 | Duffy et al. |
| 9,670,528 | B2 | 6/2017 | Handique et al. |
| 9,677,121 | B2 | 6/2017 | Ganesan et al. |
| 9,701,957 | B2 | 7/2017 | Wilson et al. |
| 9,745,623 | B2 | 8/2017 | Steel |
| 9,765,389 | B2 | 9/2017 | Gubatayao et al. |
| 9,789,481 | B2 | 10/2017 | Petersen et al. |
| 9,802,199 | B2 | 10/2017 | Handique et al. |
| 9,815,057 | B2 | 11/2017 | Handique |
| 9,958,466 | B2 | 5/2018 | Dalbert et al. |
| 10,065,185 | B2 | 9/2018 | Handique |
| 10,071,376 | B2 | 9/2018 | Williams et al. |
| 10,076,754 | B2 | 9/2018 | Lentz et al. |
| 10,100,302 | B2 | 10/2018 | Brahmasandra et al. |
| 10,139,012 | B2 | 11/2018 | Handique |
| 10,179,910 | B2 | 1/2019 | Duffy et al. |
| 10,234,474 | B2 | 3/2019 | Williams et al. |
| 10,351,901 | B2 | 7/2019 | Ganesan et al. |
| 10,364,456 | B2 | 7/2019 | Wu et al. |
| 10,443,088 | B1 | 10/2019 | Wu et al. |
| 10,494,663 | B1 | 12/2019 | Wu et al. |
| 10,571,935 | B2 | 2/2020 | Handique et al. |
| 10,590,410 | B2 | 3/2020 | Brahmasandra et al. |
| 10,604,788 | B2 | 3/2020 | Wu et al. |
| 10,619,191 | B2 | 4/2020 | Ganesan et al. |
| 10,625,261 | B2 | 4/2020 | Williams et al. |
| 10,625,262 | B2 | 4/2020 | Williams et al. |
| 10,632,466 | B1 | 4/2020 | Williams et al. |
| 10,695,764 | B2 | 6/2020 | Handique et al. |
| 10,710,069 | B2 | 7/2020 | Handique et al. |
| 10,717,085 | B2 | 7/2020 | Williams et al. |
| 10,731,201 | B2 | 8/2020 | Handique et al. |
| 10,781,482 | B2 | 9/2020 | Gubatayao et al. |
| 10,799,862 | B2 | 10/2020 | Handique et al. |
| 10,821,436 | B2 | 11/2020 | Handique et al. |
| 10,821,446 | B1 | 11/2020 | Handique et al. |
| 10,822,644 | B2 | 11/2020 | Steel et al. |
| 10,843,188 | B2 | 11/2020 | Handique et al. |
| 10,844,368 | B2 | 11/2020 | Duffy et al. |
| 10,857,535 | B2 | 12/2020 | Handique et al. |
| 10,865,437 | B2 | 12/2020 | Handique et al. |
| 10,875,022 | B2 | 12/2020 | Williams et al. |
| 10,900,066 | B2 | 1/2021 | Handique et al. |
| 10,913,061 | B2 | 2/2021 | Handique et al. |
| 11,060,082 | B2 | 7/2021 | Brahmasandra et al. |
| 11,078,523 | B2 | 8/2021 | Handique et al. |
| 11,085,069 | B2 | 8/2021 | Handique et al. |
| 11,141,734 | B2 | 10/2021 | Handique et al. |
| 11,142,785 | B2 | 10/2021 | Handique et al. |
| 11,254,927 | B2 | 2/2022 | Brahmasandra et al. |
| 11,266,987 | B2 | 3/2022 | Handique |
| 11,441,171 | B2 | 9/2022 | Wu et al. |
| 11,453,906 | B2 | 9/2022 | Handique |
| 11,466,263 | B2 | 10/2022 | Duffy et al. |
| 11,549,959 | B2 | 1/2023 | Williams et al. |
| 11,666,903 | B2 | 6/2023 | Handique et al. |
| 11,788,127 | B2 | 10/2023 | Gubatayao et al. |
| 11,806,718 | B2 | 11/2023 | Handique et al. |
| 11,845,081 | B2 | 12/2023 | Williams et al. |
| 11,959,126 | B2 | 4/2024 | Handique et al. |
| 12,030,050 | B2 | 7/2024 | Handique |
| 12,128,402 | B2 | 10/2024 | Handique |
| 12,128,405 | B2 | 10/2024 | Handique et al. |
| 12,139,745 | B2 | 11/2024 | Handique et al. |
| 12,162,007 | B2 | 12/2024 | Handique et al. |
| 2001/0005489 | A1 | 6/2001 | Roach et al. |
| 2001/0012492 | A1 | 8/2001 | Acosta et al. |
| 2001/0016358 | A1 | 8/2001 | Osawa et al. |
| 2001/0018513 | A1 | 8/2001 | Baker |
| 2001/0021355 | A1 | 9/2001 | Baugh et al. |
| 2001/0023848 | A1 | 9/2001 | Gjerde et al. |
| 2001/0038450 | A1 | 11/2001 | McCaffrey et al. |
| 2001/0045358 | A1 | 11/2001 | Kopf-Sill et al. |
| 2001/0046702 | A1 | 11/2001 | Schembri |
| 2001/0048899 | A1 | 12/2001 | Marouiss et al. |
| 2001/0051340 | A1 | 12/2001 | Singh et al. |
| 2001/0055765 | A1 | 12/2001 | O'Keefe et al. |
| 2002/0001848 | A1 | 1/2002 | Bedingham et al. |
| 2002/0008053 | A1 | 1/2002 | Hansen et al. |
| 2002/0009015 | A1 | 1/2002 | Laugharn, Jr. et al. |
| 2002/0014443 | A1 | 2/2002 | Hansen et al. |
| 2002/0015667 | A1 | 2/2002 | Chow |
| 2002/0021983 | A1 | 2/2002 | Comte et al. |
| 2002/0022261 | A1 | 2/2002 | Anderson et al. |
| 2002/0037499 | A1 | 3/2002 | Quake et al. |
| 2002/0039783 | A1 | 4/2002 | McMillan et al. |
| 2002/0047003 | A1 | 4/2002 | Bedingham et al. |
| 2002/0053399 | A1 | 5/2002 | Soane et al. |
| 2002/0054835 | A1 | 5/2002 | Robotti et al. |
| 2002/0055167 | A1 | 5/2002 | Pourahmadi et al. |
| 2002/0058332 | A1 | 5/2002 | Quake et al. |
| 2002/0060156 | A1 | 5/2002 | Mathies et al. |
| 2002/0068357 | A1 | 6/2002 | Mathies et al. |
| 2002/0068821 | A1 | 6/2002 | Gundling |
| 2002/0081669 | A1 | 6/2002 | Festoc |
| 2002/0086417 | A1 | 7/2002 | Chen |
| 2002/0086443 | A1 | 7/2002 | Bamdad |
| 2002/0090320 | A1 | 7/2002 | Burow et al. |
| 2002/0092767 | A1 | 7/2002 | Bjornson et al. |
| 2002/0094303 | A1 | 7/2002 | Yamamoto et al. |
| 2002/0131903 | A1 | 9/2002 | Ingenhoven et al. |
| 2002/0141903 | A1 | 10/2002 | Parunak et al. |
| 2002/0143297 | A1 | 10/2002 | Francavilla et al. |
| 2002/0155010 | A1 | 10/2002 | Karp et al. |
| 2002/0155477 | A1 | 10/2002 | Ito |
| 2002/0169518 | A1 | 11/2002 | Luoma et al. |
| 2002/0173032 | A1 | 11/2002 | Zou et al. |
| 2002/0176804 | A1 | 11/2002 | Strand et al. |
| 2002/0187557 | A1 | 12/2002 | Hobbs et al. |
| 2002/0192808 | A1 | 12/2002 | Gambini et al. |
| 2003/0008308 | A1 | 1/2003 | Enzelberger et al. |
| 2003/0008320 | A1 | 1/2003 | Baker |
| 2003/0019522 | A1 | 1/2003 | Parunak |
| 2003/0022392 | A1 | 1/2003 | Hudak |
| 2003/0036067 | A1 | 2/2003 | Schwartz |
| 2003/0049833 | A1 | 3/2003 | Chen et al. |
| 2003/0059823 | A1 | 3/2003 | Matsunaga et al. |
| 2003/0064507 | A1 | 4/2003 | Gallagher et al. |
| 2003/0072683 | A1 | 4/2003 | Stewart et al. |
| 2003/0073106 | A1 | 4/2003 | Johansen et al. |
| 2003/0073110 | A1 | 4/2003 | Aritomi et al. |
| 2003/0083686 | A1 | 5/2003 | Freeman et al. |
| 2003/0087300 | A1 | 5/2003 | Knapp et al. |
| 2003/0088657 | A1 | 5/2003 | Eggers |
| 2003/0096310 | A1 | 5/2003 | Hansen et al. |
| 2003/0099954 | A1 | 5/2003 | Miltenyi et al. |
| 2003/0124611 | A1 | 7/2003 | Schwartz |
| 2003/0127327 | A1 | 7/2003 | Kurnik |
| 2003/0129094 | A1 | 7/2003 | Schubert et al. |
| 2003/0134333 | A1 | 7/2003 | Dehlinger et al. |
| 2003/0136679 | A1 | 7/2003 | Bohn et al. |
| 2003/0156991 | A1 | 8/2003 | Halas et al. |
| 2003/0180192 | A1 | 9/2003 | Seippel |
| 2003/0186295 | A1 | 10/2003 | Colin et al. |
| 2003/0190608 | A1 | 10/2003 | Blackburn et al. |
| 2003/0199081 | A1 | 10/2003 | Wilding et al. |
| 2003/0211517 | A1 | 11/2003 | Carulli et al. |
| 2004/0014202 | A1 | 1/2004 | King et al. |

(56) References Cited

U.S. PATENT DOCUMENTS

2004/0014238 A1 1/2004 Krug et al.
2004/0018116 A1 1/2004 Desmond et al.
2004/0018119 A1 1/2004 Massaro
2004/0022689 A1 2/2004 Wulf et al.
2004/0029258 A1 2/2004 Heaney et al.
2004/0029260 A1 2/2004 Hansen et al.
2004/0037739 A1 2/2004 McNeely et al.
2004/0043479 A1 3/2004 Briscoe et al.
2004/0053290 A1 3/2004 Terbrueggen et al.
2004/0063217 A1 4/2004 Webster et al.
2004/0065655 A1 4/2004 Brown
2004/0072278 A1 4/2004 Chou et al.
2004/0072375 A1 4/2004 Gjerde et al.
2004/0076996 A1 4/2004 Kondo et al.
2004/0086427 A1 5/2004 Childers et al.
2004/0086870 A1 5/2004 Tyvoll et al.
2004/0086956 A1 5/2004 Bachur
2004/0132059 A1 7/2004 Scurati et al.
2004/0141887 A1 7/2004 Mainquist et al.
2004/0151629 A1 8/2004 Pease et al.
2004/0157220 A1 8/2004 Kurnool et al.
2004/0161788 A1 8/2004 Chen et al.
2004/0171515 A1 9/2004 Hamers et al.
2004/0189311 A1 9/2004 Glezer et al.
2004/0197810 A1 10/2004 Takenaka et al.
2004/0200909 A1 10/2004 McMillan et al.
2004/0203173 A1 10/2004 Peck et al.
2004/0209331 A1 10/2004 Ririe
2004/0209354 A1 10/2004 Mathies et al.
2004/0224317 A1 11/2004 Kordunsky et al.
2004/0235154 A1 11/2004 Oh et al.
2004/0240097 A1 12/2004 Evans
2004/0258565 A1 12/2004 Watari
2005/0009174 A1 1/2005 Nikiforov et al.
2005/0013737 A1 1/2005 Chow et al.
2005/0019902 A1 1/2005 Mathies et al.
2005/0037471 A1 2/2005 Liu et al.
2005/0041525 A1 2/2005 Pugia et al.
2005/0042639 A1 2/2005 Knapp et al.
2005/0048540 A1 3/2005 Inami et al.
2005/0058574 A1 3/2005 Bysouth et al.
2005/0058577 A1 3/2005 Micklash et al.
2005/0064535 A1 3/2005 Favuzzi et al.
2005/0069898 A1 3/2005 Moon et al.
2005/0084424 A1 4/2005 Ganesan et al.
2005/0106066 A1 5/2005 Saltsman et al.
2005/0112754 A1 5/2005 Yoon et al.
2005/0121324 A1 6/2005 Park et al.
2005/0129580 A1 6/2005 Swinehart et al.
2005/0130198 A1 6/2005 Ammann et al.
2005/0133370 A1 6/2005 Park et al.
2005/0135655 A1 6/2005 Kopf-Sill et al.
2005/0142036 A1 6/2005 Kim et al.
2005/0158781 A1 7/2005 Woudenberg et al.
2005/0170362 A1 8/2005 Wada et al.
2005/0186585 A1 8/2005 Juncosa et al.
2005/0196321 A1 9/2005 Huang
2005/0202470 A1 9/2005 Sundberg et al.
2005/0202489 A1 9/2005 Cho et al.
2005/0202504 A1 9/2005 Anderson et al.
2005/0205788 A1 9/2005 Itoh
2005/0208676 A1 9/2005 Kahatt
2005/0214172 A1 9/2005 Burgisser
2005/0220675 A1 10/2005 Reed et al.
2005/0226779 A1 10/2005 Oldham et al.
2005/0227269 A1 10/2005 Lloyd et al.
2005/0233370 A1 10/2005 Ammann et al.
2005/0238545 A1 10/2005 Parce et al.
2005/0239127 A1 10/2005 Ammann et al.
2005/0266489 A1 12/2005 Ammann et al.
2005/0276728 A1 12/2005 Muller-Cohn et al.
2006/0002817 A1 1/2006 Bohm et al.
2006/0003373 A1 1/2006 Ammann et al.
2006/0041058 A1 2/2006 Yin et al.
2006/0057039 A1 3/2006 Morse et al.
2006/0057629 A1 3/2006 Kim
2006/0058519 A1 3/2006 Deggerdal et al.
2006/0062696 A1 3/2006 Chow et al.
2006/0081539 A1 4/2006 Safar et al.
2006/0094004 A1 5/2006 Nakajima et al.
2006/0094108 A1 5/2006 Yoder et al.
2006/0113190 A1 6/2006 Kurnik
2006/0133965 A1 6/2006 Tajima et al.
2006/0134790 A1 6/2006 Tanaka et al.
2006/0148063 A1 7/2006 Fauzzi et al.
2006/0154341 A1 7/2006 Chen
2006/0165558 A1 7/2006 Witty et al.
2006/0165559 A1 7/2006 Greenstein et al.
2006/0177376 A1 8/2006 Tomalia et al.
2006/0177855 A1 8/2006 Utermohlen et al.
2006/0183216 A1 8/2006 Handique
2006/0201887 A1 9/2006 Siddiqi
2006/0205085 A1 9/2006 Handique
2006/0207944 A1 9/2006 Siddiqi
2006/0210435 A1 9/2006 Alavie et al.
2006/0223169 A1 10/2006 Bedingham et al.
2006/0228268 A1 10/2006 Heimberg et al.
2006/0228734 A1 10/2006 Vann et al.
2006/0246493 A1 11/2006 Jensen et al.
2006/0246533 A1 11/2006 Fathollahi et al.
2006/0269641 A1 11/2006 Atwood et al.
2006/0269961 A1 11/2006 Fukushima et al.
2007/0004028 A1 1/2007 Lair et al.
2007/0009386 A1 1/2007 Padmanabhan et al.
2007/0014695 A1 1/2007 Yue et al.
2007/0020699 A1 1/2007 Carpenter et al.
2007/0020764 A1 1/2007 Miller
2007/0026421 A1 2/2007 Sundberg et al.
2007/0042441 A1 2/2007 Masters et al.
2007/0048188 A1 3/2007 Bigus
2007/0054413 A1 3/2007 Aviles et al.
2007/0077643 A1 4/2007 Nakamura et al.
2007/0077648 A1 4/2007 Okamoto et al.
2007/0092901 A1 4/2007 Ligler et al.
2007/0098600 A1 5/2007 Kayyem et al.
2007/0099200 A1 5/2007 Chow et al.
2007/0104617 A1 5/2007 Coulling et al.
2007/0116613 A1 5/2007 Elsener
2007/0134808 A1 6/2007 Sullivan
2007/0154895 A1 7/2007 Spaid et al.
2007/0177147 A1 8/2007 Parce
2007/0178603 A1 8/2007 Takii et al.
2007/0178607 A1 8/2007 Prober et al.
2007/0184463 A1 8/2007 Molho et al.
2007/0184547 A1 8/2007 Handique et al.
2007/0196237 A1 8/2007 Neuzil et al.
2007/0196238 A1 8/2007 Kennedy et al.
2007/0199821 A1 8/2007 Chow
2007/0215554 A1 9/2007 Kreuwel et al.
2007/0218459 A1 9/2007 Miller et al.
2007/0231213 A1 10/2007 Prabhu et al.
2007/0238161 A1 10/2007 Cerrone et al.
2007/0243626 A1 10/2007 Windeyer et al.
2007/0248958 A1 10/2007 Jovanovich et al.
2007/0261479 A1 11/2007 Spaid et al.
2007/0269861 A1 11/2007 Williams et al.
2007/0292941 A1 12/2007 Handique et al.
2008/0000774 A1 1/2008 Park et al.
2008/0003649 A1 1/2008 Maltezos et al.
2008/0017306 A1 1/2008 Liu et al.
2008/0056948 A1 3/2008 Dale et al.
2008/0069729 A1 3/2008 McNeely
2008/0090244 A1 4/2008 Knapp et al.
2008/0095673 A1 4/2008 Xu
2008/0118987 A1 5/2008 Eastwood et al.
2008/0124723 A1 5/2008 Dale et al.
2008/0149840 A1 6/2008 Handique et al.
2008/0153152 A1 6/2008 Wakabayashi et al.
2008/0166793 A1 7/2008 Beer et al.
2008/0176230 A1 7/2008 Owen et al.
2008/0182301 A1* 7/2008 Handique .............. C12Q 1/686 435/303.1
2008/0192254 A1 8/2008 Kim et al.
2008/0220509 A1 9/2008 Segawa et al.

(56) References Cited

U.S. PATENT DOCUMENTS

| | | | |
|---|---|---|---|
| 2008/0226502 | A1 | 9/2008 | Jonsmann et al. |
| 2008/0240898 | A1 | 10/2008 | Manz et al. |
| 2008/0247914 | A1 | 10/2008 | Edens et al. |
| 2008/0257882 | A1 | 10/2008 | Turner |
| 2008/0280285 | A1 | 11/2008 | Chen et al. |
| 2008/0308500 | A1 | 12/2008 | Brassard |
| 2009/0047180 | A1 | 2/2009 | Kawahara |
| 2009/0066339 | A1 | 3/2009 | Glezer et al. |
| 2009/0130719 | A1 | 5/2009 | Handique |
| 2009/0130745 | A1 | 5/2009 | Williams et al. |
| 2009/0136385 | A1 | 5/2009 | Handique et al. |
| 2009/0148933 | A1 | 6/2009 | Battrell et al. |
| 2009/0189089 | A1 | 7/2009 | Bedingham et al. |
| 2009/0223925 | A1 | 9/2009 | Morse et al. |
| 2009/0325164 | A1 | 12/2009 | Vossenaar et al. |
| 2009/0325276 | A1 | 12/2009 | Battrell et al. |
| 2010/0009343 | A1 | 1/2010 | Fischer et al. |
| 2010/0009351 | A1 | 1/2010 | Brahmasandra et al. |
| 2010/0120129 | A1 | 5/2010 | Amshey et al. |
| 2010/0233763 | A1 | 9/2010 | Shigeura et al. |
| 2010/0284864 | A1 | 11/2010 | Holenstein et al. |
| 2011/0008825 | A1 | 1/2011 | Ingber et al. |
| 2011/0027151 | A1 | 2/2011 | Handique et al. |
| 2011/0060136 | A1 | 3/2011 | Matsunaga et al. |
| 2011/0097493 | A1 | 4/2011 | Kerr et al. |
| 2011/0127292 | A1 | 6/2011 | Sarofim et al. |
| 2011/0158865 | A1 | 6/2011 | Miller et al. |
| 2011/0245061 | A1* | 10/2011 | Haechler ............ G01N 35/0092 494/37 |
| 2011/0287447 | A1 | 11/2011 | Norderhaug |
| 2011/0300033 | A1 | 12/2011 | Battisti |
| 2012/0122231 | A1 | 5/2012 | Tajima |
| 2012/0160826 | A1 | 6/2012 | Handique |
| 2012/0171678 | A1 | 7/2012 | Maltezos et al. |
| 2012/0258463 | A1 | 10/2012 | Duffy et al. |
| 2013/0183769 | A1 | 7/2013 | Tajima |
| 2013/0210127 | A1 | 8/2013 | Williams et al. |
| 2013/0315800 | A1 | 11/2013 | Yin et al. |
| 2014/0030798 | A1 | 1/2014 | Wu et al. |
| 2014/0120544 | A1 | 5/2014 | Brahmasandra et al. |
| 2014/0227710 | A1 | 8/2014 | Handique et al. |
| 2014/0329301 | A1 | 11/2014 | Handique et al. |
| 2015/0045234 | A1 | 2/2015 | Stone et al. |
| 2015/0174579 | A1 | 6/2015 | Iten et al. |
| 2015/0315631 | A1 | 11/2015 | Handique et al. |
| 2016/0038942 | A1 | 2/2016 | Roberts |
| 2017/0275702 | A1 | 9/2017 | Dahiya et al. |
| 2018/0333722 | A1 | 11/2018 | Handique |
| 2019/0054467 | A1 | 2/2019 | Handique |
| 2019/0054471 | A1 | 2/2019 | Williams et al. |
| 2019/0144849 | A1 | 5/2019 | Duffy et al. |
| 2019/0145546 | A1 | 5/2019 | Handique |
| 2019/0151854 | A1 | 5/2019 | Baum et al. |
| 2019/0154719 | A1 | 5/2019 | LaChance et al. |
| 2019/0284606 | A1 | 9/2019 | Wu et al. |
| 2019/0324050 | A1 | 10/2019 | Williams et al. |
| 2020/0139363 | A1 | 5/2020 | Handique et al. |
| 2020/0156059 | A1 | 5/2020 | Handique et al. |
| 2020/0156060 | A1 | 5/2020 | Handique et al. |
| 2020/0164363 | A1 | 5/2020 | Handique et al. |
| 2020/0215536 | A1 | 7/2020 | Handique et al. |
| 2020/0216831 | A1 | 7/2020 | Brahmasandra et al. |
| 2020/0291388 | A1 | 9/2020 | Brahmasandra et al. |
| 2020/0324293 | A1 | 10/2020 | Handique et al. |
| 2020/0325523 | A1 | 10/2020 | Brahmasandra et al. |
| 2020/0325524 | A1 | 10/2020 | Handique et al. |
| 2021/0001334 | A1 | 1/2021 | Handique et al. |
| 2021/0010059 | A1 | 1/2021 | Handique et al. |
| 2021/0047676 | A1 | 2/2021 | Wu et al. |
| 2021/0060565 | A1 | 3/2021 | Handique et al. |
| 2021/0087609 | A1 | 3/2021 | Handique et al. |
| 2021/0121887 | A1 | 4/2021 | Handique et al. |
| 2021/0123090 | A1 | 4/2021 | Handique et al. |
| 2021/0276008 | A1 | 9/2021 | Handique et al. |
| 2021/0299663 | A1 | 9/2021 | Handique |
| 2021/0317437 | A1 | 10/2021 | Duffy et al. |
| 2021/0362155 | A1 | 11/2021 | Williams et al. |
| 2022/0010364 | A1 | 1/2022 | Handique et al. |
| 2022/0136034 | A1 | 5/2022 | Handique et al. |
| 2022/0170008 | A1 | 6/2022 | Brahmasandra et al. |
| 2022/0203371 | A1 | 6/2022 | Handique et al. |
| 2022/0241782 | A1 | 8/2022 | Handique et al. |
| 2023/0023741 | A1 | 1/2023 | Handique |
| 2023/0041595 | A1 | 2/2023 | Wu et al. |
| 2024/0326057 | A1 | 10/2024 | Handique et al. |
| 2024/0359179 | A1 | 10/2024 | Williams et al. |
| 2025/0010295 | A1 | 1/2025 | Handique |
| 2025/0075250 | A1 | 3/2025 | Handique et al. |

FOREIGN PATENT DOCUMENTS

| | | | |
|---|---|---|---|
| AU | 4437602 | | 7/2002 |
| AU | 4437702 | | 7/2002 |
| AU | 764319 | B2 | 8/2003 |
| CA | 2574107 | | 9/1998 |
| CA | 2294819 | | 1/1999 |
| CN | 1934451 | | 3/2007 |
| CN | 1312287 | C | 4/2007 |
| CN | 1942590 | A | 4/2007 |
| CN | 1968754 | A | 5/2007 |
| CN | 101466848 | | 6/2009 |
| CN | 101522909 | | 9/2009 |
| CN | 103540518 | | 1/2014 |
| DE | 19755479 | A1 | 6/1999 |
| DE | 19929734 | | 12/1999 |
| DE | 19833293 | C1 | 1/2000 |
| EP | 0136126 | A2 | 4/1985 |
| EP | 0365828 | A2 | 5/1990 |
| EP | 0483620 | A2 | 5/1992 |
| EP | 0402994 | B1 | 11/1994 |
| EP | 0393744 | B1 | 1/1995 |
| EP | 0688602 | A2 | 12/1995 |
| EP | 0707077 | A2 | 4/1996 |
| EP | 0698046 | B1 | 3/1997 |
| EP | 0766256 | | 4/1997 |
| EP | 0772494 | B1 | 5/1997 |
| EP | 0810030 | A1 | 12/1997 |
| EP | 1059458 | A2 | 12/2000 |
| EP | 1064090 | A1 | 1/2001 |
| EP | 1077086 | A2 | 2/2001 |
| EP | 1346772 | A2 | 9/2003 |
| EP | 1541237 | A2 | 6/2005 |
| EP | 1574586 | A2 | 9/2005 |
| EP | 1621890 | A1 | 2/2006 |
| EP | 1745153 | | 1/2007 |
| EP | 1780290 | A2 | 5/2007 |
| EP | 1792656 | A1 | 6/2007 |
| EP | 2372367 | A1 | 10/2011 |
| FR | 2672301 | | 8/1992 |
| FR | 2795426 | | 12/2000 |
| GB | 2453432 | A | 4/2009 |
| JP | S50-100881 | | 8/1975 |
| JP | 58212921 | A | 12/1983 |
| JP | S62-119460 | | 5/1987 |
| JP | H01-502319 | | 8/1989 |
| JP | H03181853 | | 8/1991 |
| JP | 04-053555 | U | 5/1992 |
| JP | 06-064156 | U | 9/1994 |
| JP | 07-020010 | | 1/1995 |
| JP | H07-290706 | | 11/1995 |
| JP | H08-122336 | | 5/1996 |
| JP | H08-173194 | | 7/1996 |
| JP | H08-211071 | | 8/1996 |
| JP | H08-285859 | | 11/1996 |
| JP | H08-337116 | | 12/1996 |
| JP | H09-304385 | | 11/1997 |
| JP | H09-325151 | | 12/1997 |
| JP | 2001-502790 | | 1/1998 |
| JP | H01-219669 | | 9/1998 |
| JP | H10-327515 | | 12/1998 |
| JP | H11-501504 | | 2/1999 |
| JP | H11-503315 | | 3/1999 |
| JP | 2000-514928 | | 4/1999 |
| JP | H11-316226 | | 11/1999 |

(56) References Cited

FOREIGN PATENT DOCUMENTS

| | | | |
|---|---|---|---|
| JP | H11-515106 | | 12/1999 |
| JP | 2000-180455 | | 6/2000 |
| JP | 2000-266760 | | 9/2000 |
| JP | 2000-275255 | | 10/2000 |
| JP | 2001-502319 | | 2/2001 |
| JP | 2001-204462 | | 7/2001 |
| JP | 2001-509437 | | 7/2001 |
| JP | 3191150 | B2 | 7/2001 |
| JP | 2001-515216 | | 9/2001 |
| JP | 2001-523812 | | 11/2001 |
| JP | 2001-527220 | | 12/2001 |
| JP | 2002-503331 | | 1/2002 |
| JP | 2002-085961 | | 3/2002 |
| JP | 2002-517735 | | 6/2002 |
| JP | 2002-215241 | | 7/2002 |
| JP | 2002-540382 | | 11/2002 |
| JP | 2002-544476 | | 12/2002 |
| JP | 2003-500169 | | 1/2003 |
| JP | 2003-500674 | | 1/2003 |
| JP | 2003-047839 | A | 2/2003 |
| JP | 2003-047840 | A | 2/2003 |
| JP | 2003-516125 | | 5/2003 |
| JP | 2003-164279 | | 6/2003 |
| JP | 2003-185584 | | 7/2003 |
| JP | 2003-299485 | | 10/2003 |
| JP | 2003-329693 | | 11/2003 |
| JP | 2003-329696 | | 11/2003 |
| JP | 2003-532382 | A | 11/2003 |
| JP | 2004-003989 | | 1/2004 |
| JP | 2004-506179 | A | 2/2004 |
| JP | 2004-150797 | A | 5/2004 |
| JP | 2004-283728 | A | 10/2004 |
| JP | 2004-531360 | A | 10/2004 |
| JP | 2004-533838 | | 11/2004 |
| JP | 2004-534157 | | 11/2004 |
| JP | 2004-361421 | | 12/2004 |
| JP | 2004-536291 | | 12/2004 |
| JP | 2005-009870 | | 1/2005 |
| JP | 2005-010179 | | 1/2005 |
| JP | 2005-511264 | | 4/2005 |
| JP | 2005-514718 | | 5/2005 |
| JP | 2005-518825 | | 6/2005 |
| JP | 2005-176613 | A | 7/2005 |
| JP | 2005-192439 | | 7/2005 |
| JP | 2005-192554 | | 7/2005 |
| JP | 2005-519751 | | 7/2005 |
| JP | 2005-204661 | | 8/2005 |
| JP | 2005-525816 | | 9/2005 |
| JP | 2005-291954 | A | 10/2005 |
| JP | 2005-323519 | | 11/2005 |
| JP | 2005-533652 | | 11/2005 |
| JP | 2005-535904 | | 11/2005 |
| JP | 2006-021156 | A | 1/2006 |
| JP | 2006-055837 | A | 3/2006 |
| JP | 2006-094866 | A | 4/2006 |
| JP | 2006-145458 | | 6/2006 |
| JP | 2006-167569 | | 6/2006 |
| JP | 2006-284409 | | 10/2006 |
| JP | 2007-024742 | A | 2/2007 |
| JP | 2007-074960 | | 3/2007 |
| JP | 2007-097477 | | 4/2007 |
| JP | 2007-101364 | | 4/2007 |
| JP | 2007-510518 | | 4/2007 |
| JP | 2007-514405 | A | 6/2007 |
| JP | 2007-178328 | | 7/2007 |
| JP | 2009-542207 | | 12/2009 |
| JP | 3193848 | U | 10/2014 |
| KR | 1020060044489 | A | 5/2006 |
| RU | 2418633 | C2 | 5/2011 |
| WO | WO 1988/006633 | | 9/1988 |
| WO | WO 1990/012350 | | 10/1990 |
| WO | WO 1992/005443 | | 4/1992 |
| WO | WO 1994/005414 | | 3/1994 |
| WO | WO 1994/011103 | | 5/1994 |
| WO | WO 1995/033846 | | 12/1995 |
| WO | WO 1996/000228 | | 1/1996 |
| WO | WO 1996/004547 | | 2/1996 |
| WO | WO 1996/018731 | | 6/1996 |
| WO | WO 1996/039547 | | 12/1996 |
| WO | WO 1997/005492 | | 2/1997 |
| WO | WO 1997/016835 | | 5/1997 |
| WO | WO 1997/021090 | | 6/1997 |
| WO | WO 1997/022825 | | 6/1997 |
| WO | WO 1997/027324 | | 7/1997 |
| WO | WO 1998/000231 | | 1/1998 |
| WO | WO 1998/007019 | | 2/1998 |
| WO | WO 1998/022625 | | 5/1998 |
| WO | WO 1998/035013 | | 8/1998 |
| WO | WO 1998/038487 | | 9/1998 |
| WO | WO 1998/049548 | | 11/1998 |
| WO | WO 1998/050147 | | 11/1998 |
| WO | WO 1998/053311 | | 11/1998 |
| WO | WO 1999/001688 | | 1/1999 |
| WO | WO 1999/009042 | | 2/1999 |
| WO | WO 1999/012016 | | 3/1999 |
| WO | WO 1999/016549 | | 4/1999 |
| WO | WO 1999/017093 | | 4/1999 |
| WO | WO 1999/029703 | | 6/1999 |
| WO | WO 1999/033559 | | 7/1999 |
| WO | WO 1999/060397 | | 11/1999 |
| WO | WO 2000/022436 | | 4/2000 |
| WO | WO 2000/066783 | | 11/2000 |
| WO | WO 2000/073412 | | 12/2000 |
| WO | WO 2000/075623 | | 12/2000 |
| WO | WO 2000/078455 | | 12/2000 |
| WO | WO 2001/005510 | | 1/2001 |
| WO | WO 2001/014931 | | 3/2001 |
| WO | WO 2001/027614 | | 4/2001 |
| WO | WO 2001/028684 | | 4/2001 |
| WO | WO 2001/030995 | | 5/2001 |
| WO | WO 2001/041931 | | 6/2001 |
| WO | WO 2001/046474 | | 6/2001 |
| WO | WO 2001/054813 | | 8/2001 |
| WO | WO 2001/089681 | | 11/2001 |
| WO | WO 2001/089705 | | 11/2001 |
| WO | WO 2001/092569 | | 12/2001 |
| WO | WO 2002/043864 | | 6/2002 |
| WO | WO 2002/048164 | | 6/2002 |
| WO | WO 2002/052002 | | 7/2002 |
| WO | WO 2002/072264 | | 9/2002 |
| WO | WO 2002/078845 | | 10/2002 |
| WO | WO 2002/086454 | | 10/2002 |
| WO | WO 2002/094185 | | 11/2002 |
| WO | WO 2003/007677 | | 1/2003 |
| WO | WO 2003/012325 | | 2/2003 |
| WO | WO 2003/012406 | | 2/2003 |
| WO | WO 2003/048295 | | 6/2003 |
| WO | WO 2003/055605 | | 7/2003 |
| WO | WO 2003/076661 | | 9/2003 |
| WO | WO 2003/078065 | | 9/2003 |
| WO | WO 2003/080868 | | 10/2003 |
| WO | WO 2003/087410 | | 10/2003 |
| WO | WO 2004/007081 | | 1/2004 |
| WO | WO 2004/010760 | | 2/2004 |
| WO | WO 2004/048545 | | 6/2004 |
| WO | WO 2004/055522 | | 7/2004 |
| WO | WO 2004/056485 | | 7/2004 |
| WO | WO 2004/074848 | | 9/2004 |
| WO | WO 2004/094986 | | 11/2004 |
| WO | WO 2005/008255 | | 1/2005 |
| WO | WO 2005/011867 | | 2/2005 |
| WO | WO 2005/030984 | | 4/2005 |
| WO | WO 2005/072353 | | 8/2005 |
| WO | WO 2005/094981 | | 10/2005 |
| WO | WO 2005/100538 | | 10/2005 |
| WO | WO 2005/107947 | | 11/2005 |
| WO | WO 2005/108571 | | 11/2005 |
| WO | WO 2005/108620 | | 11/2005 |
| WO | WO 2005/116202 | | 12/2005 |
| WO | WO 2005/118867 | | 12/2005 |
| WO | WO 2005/120710 | | 12/2005 |
| WO | WO 2006/010584 | | 2/2006 |
| WO | WO 2006/032044 | | 3/2006 |
| WO | WO 2006/035800 | | 4/2006 |

(56) References Cited

FOREIGN PATENT DOCUMENTS

| | | |
|---|---|---|
| WO | WO 2006/043642 | 4/2006 |
| WO | WO 2006/066001 | 6/2006 |
| WO | WO 2006/079082 | 7/2006 |
| WO | WO 2006/081324 | 8/2006 |
| WO | WO 2006/081995 | 8/2006 |
| WO | WO 2006/113198 | 10/2006 |
| WO | WO 2006/118420 | 11/2006 |
| WO | WO 2006/119280 | 11/2006 |
| WO | WO 2007/044917 | 4/2007 |
| WO | WO 2007/050327 | 5/2007 |
| WO | WO 2007/064117 | 6/2007 |
| WO | WO 2007/075919 | 7/2007 |
| WO | WO 2007/091530 | 8/2007 |
| WO | WO 2007/112114 | 10/2007 |
| WO | WO 2007/120240 | 10/2007 |
| WO | WO 2007/120241 | 10/2007 |
| WO | WO 2008/005321 | 1/2008 |
| WO | WO 2008/030914 | 3/2008 |
| WO | WO 2008/044387 | 4/2008 |
| WO | WO 2008/060604 | 5/2008 |
| WO | WO 2008/118566 | 10/2008 |
| WO | WO 2008/134470 | 11/2008 |
| WO | WO 2008/149282 | 12/2008 |
| WO | WO 2009/012185 | 1/2009 |
| WO | WO 2009/054870 | 4/2009 |
| WO | WO 2010/118541 | 10/2010 |
| WO | WO 2010/130310 | 11/2010 |
| WO | WO 2010/140680 | 12/2010 |
| WO | WO 2011/009073 | 1/2011 |
| WO | WO 2011/101467 | 8/2011 |

OTHER PUBLICATIONS

Asymtek: High-Speed Dispensejet DJ-9000 Jet; ASI Adhesives & Sealants Industry; Press Release dated Nov. 17, 2003; 2 pages.

Yang et al., "Integrated Multiprocess Microfluidic Systems for Automating Analysis", JALA Jun. 2010;15(3): 198-209.

Benters et al., "Dendrimer-Activated Solid Supports for Nucleic Acid and Protein Microarrays", ChemBioChem (2001) 2(9): 686-694.

Devarakonda et al., "The effect of PAMAM dendrimer generation size and surface functional group on the aqueous solubility of nifedipine", Int J Pharma. 284(1-2): 133-140.

Brief for Appellee HandyLab, Inc. in Appeals from the USPTO, PTAB, in Nos. IPR2019-00488, IPR2019-00490, IPR2019-01493 and IPR2019-01494 filed May 24, 2021 in U.S. Court of Appeals for the Federal Circuit Case Nos. 20-2249, 20-2250, 20-2273 and 20-2276 (74 pages).

Reply Brief of Appellants Qiagen North American Holdings, Inc. and NeuMoDx Molecular, Inc. in Appeals from the USPTO, PTAB, in Nos. IPR2019-00488, IPR2019-00490, IPR2019-01493 and IPR2019-01494 filed Jun. 21, 2021 in U.S. Court of Appeals for the Federal Circuit Case Nos. 20-2249, 20-2250, 20-2273 and 20-2276 (44 pages).

Decision Denying Institution of Inter Partes Review of U.S. Pat. No. 10,625,262 (Paper 7 in IPR2021-00250) dated Jul. 15, 2021 (15 pages).

Decision Denying Institution of Inter Partes Review of U.S. Pat. No. 10,632,466 (Paper 7 in IPR2021-00253) dated Jul. 15, 2021 (22 pages).

Decision Denying Institution of Inter Partes Review of U.S. Pat. No. 10,625,261 (Paper 7 in IPR2021-00251) dated Jul. 15, 2021 (24 pages).

Patent Owner's Response in Inter Partes Review of U.S. Pat. No. 8,709,787 and Exhibit List (Paper 29 in IPR 2020-01132) dated Jul. 15, 2021 (87 pages).

Decision Granting Institution of Inter Partes Review of U.S. Pat. No. 8,415,103 on Rehearing (Paper 23 in IPR2020-01133) dated Aug. 6, 2021 (20 pages).

Decision of U.S. Court of Appeal for the Federal Circuit Affirming Inter Partes Review Final Written Decisions Determining No Challenged Claims of U.S. Pat. Nos. 7,998,708 and 8,323,900 are Unpatentable (IPR2019-00488, IPR2019-00490, IPR2019-01493, and IPR2019-01494) dated Oct. 29, 2021 (12 pages).

Joint Motion to Terminate Inter Partes Review of U.S. Pat. No. 8,709,787 (Paper 37 in IPR 2020-01132) dated Nov. 15, 2021 (8 pages).

Joint Motion to Terminate Inter Partes Review of U.S. Pat. No. 8,415,103 (Paper 35 in IPR 2020-01133) dated Nov. 15, 2021 (8 pages).

Stipulation of Dismissal filed by Plaintiffs Becton, Dickinson and Company, Geneohm Sciences Canada, Inc. and HandyLab, Inc. and Defendants NeuMoDx Molecular, Inc., Qiagen GmbH, and Qiagen North American Holdings, Inc. on Nov. 12, 2021 in U.S. District Court, Delaware, Case # 1:19-cv-01226-LPS (3 pages).

Allemand et al., "pH-Dependent Specific Binding and Combing of DNA", Biophys J. (1997) 73(4): 2064-2070.

Altet et al., [Eds.] "Thermal Transfer and Thermal Coupling in IC's", Thermal Testing of Integrated Circuits; Chapter 2 (2002) Springer Science pp. 23-51.

Ateya et al., "The good, the bad, and the tiny: a review of microflow cytometry", Anal Bioanal Chem. (2008) 391(5):1485-1498.

Auroux et al., "Miniaturised nucleic acid analysis", Lab Chip. (2004) 4(6):534-546.

Baechi et al., "High-density microvalve arrays for sample processing in PCR chips", Biomed Microdevices. (2001) 3(3):183-190.

Baker M., "Clever PCR: more genotyping, smaller volumes." Nature Methods (May 2010) 70(5):351-356.

Becker H. "Fabrication of Polymer Microfluidic Devices", in Biochip Technology (2001), Chapter 4, pp. 63-96.

Becker H., "Microfluidic Devices Fabricated by Polymer Hot Embossing," in Integrated Microfabricated Biodevices: Advanced Technologies for Genomics, Drug Discovery, Bioanalysis, and Clinical Diagnostics (2002), Chapter 13, 32 pages.

Becker H., "Microfluidics: A Technology Coming of Age", Med Device Technol. (2008) 19(3):21-24.

Becker et al., "Portable CE system with contactless conductivity detection in an injection molded polymer chip for on-site food analysis", SPIE Proceedings MOEMS-MEMS 2008 Micro and Nanofabrication (2008) vol. 6886 in 8 pages.

Becker H., "Hype, hope and hubris: the quest for the killer application in microfluidics", Lab on a Chip, The Royal Society of Chemistry (2009) 9:2119-2122.

Becker H., "Collective Wisdom", Lab on a Chip, The Royal Society of Chemistry (2010) 10:1351-1354.

Belgrader et al., " Rapid PCR for Identity Testing Using a Battery-Powered Miniature Thermal Cycler", J Forensic Sci. (1998) 43(2):315-319.

Belgrader et al., "A minisonicator to rapidly disrupt bacterial spores for DNA analysis.", Anal Chem. (1999) 71(19):4232-4236.

Belgrader et al., "Real-time PCR Analysis on Nucleic Acids Purified from Plasma Using a Silicon Chip", Micro Total Analysis Systems 2000 (pp. 525-528). Springer, Dordrecht.

Belgrader et al., "A microfluidic cartridge to prepare spores for PCR analysis", Biosens Bioelectron. (2000) 14(10-11):849-852.

Belgrader et al., "A Battery-Powered Notebook Thermal Cycler for Rapid Multiplex Real-Time PCR Analysis", Anal Chem. (2001) 73(2):286-289.

Belgrader et al., "Rapid and Automated Cartridge-based Extraction of Leukocytes from Whole Blood for Microsatellite DNA Analysis by Capillary Electrophoresis", Clin Chem. (2001) 47(10):1917-1933.

Belgrader et al., "A Rapid, Flow-through, DNA Extraction Module for Integration into Microfluidic Systems", Micro Total Analysis Systems (2002) pp. 697-699). Springer, Dordrecht.

Belgrader et al., "Development of a Battery-Powered Portable Instrumentation for RapidPCR Analysis", in Integrated Microfabricated Devices, (2002) Ch. 8, pp. 183-206, CRC Press.

Bell M., "Integrated Microsystems in Clinical Chemistry", in Integrated Microfabricated Devices, (2002) Ch. 16, pp. 415-435, CRC Press.

Berthier et al., "Managing evaporation for more robust microscale assays Part 1. Volume loss in high throughput assays", Lab Chip (2008) 8(6):852-859.

(56) References Cited

OTHER PUBLICATIONS

Berthier et al., "Managing evaporation for more robust microscale assays Part 2. Characterization of convection and diffusion for cell biology", Lab Chip (2008) 8(6):860-864.
Berthier et al., "Microdrops," in Microfluidics for Biotechnology (2006), Chapter 2, pp. 51-88.
Biomerieux Press Release: "bioMérieux—2018 Financial Results," dated Feb. 27, 2019, accessed at www.biomerieux.com, p. 13.
Blanchard et al., "Micro structure mechanical failure characterization using rotating Couette flow in a small gap", J Micromech Microengin. (2005) 15(4):792-801.
Blanchard et al., "Single-disk and double-disk viscous micropumps", Sensors and Actuators A (2005) 122:149-158.
Blanchard et al., "Performance and Development of a Miniature Rotary Shaft Pump", J Fluids Eng. (2005) 127(4):752-760.
Blanchard et al., "Single-disk and double-disk viscous micropump", ASME 2004 Inter'l Mechanical Engineering Congress & Exposition, Nov. 13-20, 2004, Anaheim, CA, IMECE2004-61705:411-417.
Blanchard et al., "Miniature Single-Disk Viscous Pump (Single-DVP), Performance Characterization", J Fluids Eng. (2006) 128(3):602-610.
Bollet, C. et al., "A simple method for the isolation of chromosomal DNA from Gram positive or acid-fast bacteria", Nucleic Acids Research, vol. 19, No. 8 (1991), p. 1955.
Brahmasandra et al., On-chip DNA detection in microfabricated separation systems,SPIE Conference on Microfluidic Devices and Systems, 1998, vol. 3515, pp. 242-251, Santa Clara, CA.
Brahmasandra et al., "Microfabricated Devices for Integrated DNA Analysis", in Biochip Technology by Cheng et al., [Eds.] (2001) pp. 229-250.
Breadmore, M.C. et al., "Microchip-Based Purification of DNA from Biological Samples", Anal. Chem., vol. 75 (2003), pp. 1880-1886.
Brody, et al., Diffusion-Based Extraction in a Microfabricated Device, Sensors and Actuators Elsevier, 1997, vol. A58, No. 1, pp. 13-18.
Broyles et al., "Sample Filtration, Concentration, and Separation Integrated on Microfluidic Devices" Analytical Chemistry (American Chemical Society), (2003) 75(11): 2761-2767.
Bu et al., "Design and theoretical evaluation of a novel microfluidic device to be used for PCR", J Micromech Microengin. (2003) 13(4):S125-S130.
Burns et al., "An Integrated Nanoliter DNA Analysis Device", Science 282:484-487 (1998).
Cady et al., "Real-time PCR detection of Listeria monocytogenes using an integrated microfluidics platform", Sensors Actuat B. (2005) 107:332-341.
Carlen et al., "Paraffin Actuated Surface Micromachined Valve," in IEEE MEMS 2000 Conference, Miyazaki, Japan, (Jan. 2000) pp. 381-385.
Carles et al., "Polymerase Chain Reaction on Microchips" in Methods in Molecular Biology—Microfluidic Techniques, Reviews & Protocols by Minteer S.D. [Ed.] Humana Press (2006), vol. 321; Chapter 11, pp. 131-140.
Chang-Yen et al., "A novel integrated optical dissolved oxygen sensor for cell culture and micro total analysis systems", IEEE Technical Digest MEMS International Conference Jan. 24, 2002, 4 pages.
Chang-Yen et al., "A PDMS microfluidic spotter for fabrication of lipid microarrays", IEEE 3rd EMBS Special Topic Conference May 12-15, 2005; 2 pages.
Chang-Yen et al., "Design and fabrication of a multianalyte-capable optical biosensorusing a multiphysics approach", IEEE 3rd EMBS Special Topic Conference May 12-15, 2005; 2 pages.
Chang-Yen et al., "A Novel PDMS Microfluidic Spotter for Fabrication of Protein Chips and Microarrays", IEEE J of Microelectromech Sys. (2006) 15(5): 1145-1151.
Chang-Yen et al., "Design, fabrication, and packaging of a practical multianalyte-capable optical biosensor," J Microlith Microfab Microsyst. (2006) 5(2):021105 in 8 pages.
Chang-Yen et al., "Spin-assembled nanofilms for gaseous oxygen sensing." Sens Actuators B: Chemical (2007), 120(2):426-433.
Chaudhari et al., "Transient Liquid Crystal Thermometry of Microfabricated PCR Vessel Arrays", J Microelectro Sys., (1998) 7(4):345-355.
Chen P-C., "Accelerating micro-scale PCR (polymerase chain reactor) for modular lab-on-a-chip system", LSU Master's Theses—Digital Commons, (2006) 111 pages.
Chen et al., "Total nucleic acid analysis integrated on microfluidic devices," Lab on a Chip. (2007) 7:1413-1423.
Cheng et al., "Biochip-Based Portable Laboratory", Biochip Tech. (2001):269-289.
Cho et al., "A facility for characterizing the steady-state and dynamic thermal performance of microelectromechanical system thermal switches", Rev Sci Instrum. (2008) 79(3):034901-1 to -8.
Chong et al., "Disposable Polydimethylsiloxane Package for 'Bio-Microfluidic System'", IEEE Proceedings Electronic Components and Technology (2005); 5 pages.
Chou et al., "A miniaturized cyclic PCR device-modeling and experiments", Microelec Eng. (2002) 61-62:921-925.
Christel et al., "Nucleic Acid Concentration and PCR for Diagnostic Applications", in Micro Total Analysis Systems. (1998) D.J. Harrison et al. [Eds.] pp. 277-280.
Christel et al., "Rapid, Automated Nucleic Acid Probe Assays Using Silicon Microstructures for Nucleic Acid Concentration", J Biomech Eng. (1999) 121(1):22-27.
Christensen et al., "Characterization of interconnects used in PDMS microfluidic systems", J Micromech Microeng. (2005) 15:928 in 8 pages.
Chung, Y. et al., "Microfluidic chip for high efficiency DNA extraction", Miniaturisation for Chemistry, Biology & Bioengineering, vol. 4, No. 2 (Apr. 2004), pp. 141-147.
Cooley et al., "Applications of Ink-Jet Printing Technology to BioMEMS and Microfluidic Systems", Proceedings, SPIE Conference on Microfluids and BioMEMS, (Oct. 2001), 12 pages.
Crews et al., "Rapid Prototyping of a Continuous-Flow PCR Microchip", Proceedings of the AiChE Annual Meeting (Nov. 15, 2006) (335a) 3 pages.
Crews et al., Thermal gradient PCR in a continuous-flow microchip. In Microfluidics, BioMEMS, and Medical Microsystems V; Jan. 2007; vol. 6465, p. 646504; 12 pages.
Crews et al., "Continuous-flow thermal gradient PCR", Biomed Microdevices. (2008) 10(2):187-195.
Cui et al., "Electrothermal modeling of silicon PCR chips", In MEMS Design, Fabrication, Characterization, and Packaging, (Apr. 2001) (vol. 4407, pp. 275-280.
Cui et al., "Design and Experiment of Silicon PCR Chips," Proc. SPIE 4755, Design, Test, Integration, and Packaging of MEMS/MOEMS 2002, (Apr. 19, 2002) pp. 71-76.
Danaher Press Release: "Danaher to Acquire Cepheid for $53.00 per share, or approximately $4 Billion," dated Sep. 6, 2016, accessed at www.danaher.com, p. 3.
Demchenko A.P., "The problem of self-calibration of fluorescence signal in microscale sensor systems", Lab Chip. (2005) 5(11):1210-1223.
Dineva et al., "Sample preparation: a challenge in the development of point-of-care nucleic acid-based assays for resource-limited settings", Analyst. (2007) 132(12):1193-1199.
Dishinger et al., "Multiplexed Detection and Applications for Separations on Parallel Microchips", Electrophoresis. (2008) 29(16):3296-3305.
Dittrich et al., "Single-molecule fluorescence detection in microfluidic channels—the Holy Grail in muTAS?", Anal Bioanal Chem. (2005) 382(8):1771-1782.
Dittrich et al., "Lab-on-a-chip: microfluidics in drug discovery", Nat Rev Drug Discov. (2006) 5(3):210-218.
Dunnington et al., "Approaches to Miniaturized High-Throughput Screening of Chemical Libraries", in Integrated Microfabricated Devices, (2002) Ch. 15, pp. 371-414, CRC Press.

(56) References Cited

OTHER PUBLICATIONS

Eddings et al., "A PDMS-based gas permeation pump for on-chip fluid handling in microfluidic devices", J Micromech Microengin. (2006) 16(11):2396-2402.
Edwards, "Silicon (Si)," in "Handbook of Optical Constants of Solids" (Ghosh & Palik eds., 1997) in 24 pages.
Edwards et al., "Micro Scale Purification Systems for Biological Sample Preparation", Biomed Microdevices (2001) 3(3):211-218.
Edwards et al., "A microfabricated thermal field-flow fractionation system", Anal Chem. (2002) 74(6):1211-1216.
Ehrlich et al., "Microfluidic devices for DNA analysis", Trends Biotechnol. (1999) 17(8):315-319.
El-Ali et al., "Simulation and experimental validation of a SU-8 based PCR thermocycler chip with integrated heaters and temperature sensor", Sens Actuators A: Physical (2004) 110(1-3):3-10.
Erickson et al., "Joule heating and heat transfer in poly(dimethylsiloxane) microfluidic systems", Lab Chip (2003) 3(3):141-149.
Erickson et al., "Integrated Microfluidic Devices", Analytica Chim Acta. (2004) 507:11-26.
Erill et al., "Development of a CMOS-compatible PCR chip: comparison of design and system strategies", J Micromech Microengin. (2004) 14(11):1-11.
Fair R.B., Digital microfluidics: is a true lab-on-a-chip possible? Microfluidics Nanofluid. (2007) 3:245-281.
Fan et al., "Integrated Plastic Microfluidic Devices for Bacterial Detection", in Integrated Biochips for DNA Analysis by Liu et al. [Eds], (2007) Chapter 6, pp. 78-89.
Fiorini et al., "Disposable microfluidic devices: fabrication, function, and application", Biotechniques (2005) 38(3):429-446.
Frazier et al., "Integrated micromachined components for biological analysis systems", J Micromech. (2000) 1(1):67-83.
Gale et al., "Micromachined electrical field-flow fractionation (mu-EFFF) system", IEEE Trans Biomed Eng. (1998) 45(12):1459-1469.
Gale et al., "Geometric scaling effects in electrical field flow fractionation. 1. Theoretical analysis", Anal Chem. (2001) 73(10):2345-2352.
Gale et al., "BioMEMS Education at Louisiana Tech University", Biomed Microdevices, (2002) 4:223-230.
Gale et al., "Geometric scaling effects in electrical field flow fractionation. 2. Experimental results", Anal Chem. (2002) 74(5):1024-1030.
Gale et al., "Cyclical electrical field flow fractionation", Electrophoresis. (2005) 26(9):1623-1632.
Gale et al., "Low-Cost MEMS Technologies", Elsevier B.V. (2008), Chapter 1.12; pp. 342-372.
Garst et al., "Fabrication of Multilayered Microfluidic 3D Polymer Packages", IEEE Proceedings Electronic Components & Tech, Conference May/Jun. 2005, pp. 603-610.
GÄRTNER et al., "Methods and instruments for continuous-flow PCR on a chip", Proc. SPIE 6465, Microfluidics, BioMEMS, and Medical Microsystems V, (2007) 646502; 8 pages.
Giordano et al., "Toward an Integrated Electrophoretic Microdevice for Clinical Diagnostics", in Integrated Microfabricated Biodevices: Advanced Technologies for Genomics, Drug Discovery, Bioanalysis, and Clinical Diagnostics (2002) Chapter 1; pp. 1-34.
Goldmeyer et al., "Identification of *Staphylococcus aureus* and Determination of Methicillin Resistance Directly from Positive Blood Cultures by Isothermal Amplification and a Disposable Detection Device", J Clin Microbiol. (Apr. 2008) 46(4): 1534-1536.
Graff et al., "Nanoparticle Separations Using Miniaturized Field-flow Fractionation Systems", Proc. Nanotechnology Conference and Trade Show (NSTI) (2005); pp. 8-12.
Greer et al., "Comparison of glass etching to xurography prototyping of microfluidic channels for DNA melting analysis", J Micromech Microengin. (2007) 17(12):2407-2413.
Grunenwald H., "Optimization of Polymerase Chain Reactions," in Methods in Molecular Biology, PCR Protocols., Second Edition by Bartlett et al. [Eds.] Humana Press (2003) vol. 226, pp. 89-99.
Guijt et al., "Chemical and physical processes for integrated temperature control in microfluidic devices", Lab Chip. (2003) 3(1):1-4.
Gulliksen A., "Microchips for Isothermal Amplification of RNA", Doctoral Thesis (2007); Department of Mol. Biosciences-University of Oslo; 94 pages.
Guttenberg et al., "Planar chip device for PCR and hybridization with surface acoustic wave pump", Lab Chip. (2005) 5(3):308-317.
Haeberle et al., "Microfluidic platforms for lab-on-a-chip applications", Lab Chip. (2007) 7(9):1094-1110.
Hale et al., "Optical constants of Water in the 200-nm to 200-um Wavelength Region", Applied Optics, 12(3): 555-563 (1973).
Handal et al., "DNA mutation detection and analysis using miniaturized microfluidic systems", Expert Rev Mol Diagn. (2006) 6(1):29-38.
Handique et al., "Microfluidic flow control using selective hydrophobic patterning", SPIE, (1997) 3224: 185-194.
Handique et al., "On-Chip Thermopneumatic Pressure for Discrete Drop Pumping", Anal. Chem., (2001) 73(8):1831-1838.
Handique et al., "Nanoliter-volume discrete drop injection and pumping in microfabricated chemical analysis systems", Solid-State Sensor and Actuator Workshop (Hilton Head, South Carolina, Jun. 8-11, 1998) pp. 346-349.
Handique et al., "Mathematical Modeling of Drop Mixing in a Slit-Type Microchannel", J. Micromech. Microeng., 11:548-554 (2001).
Handique et al., "Nanoliter Liquid Metering in Microchannels Using Hydrophobic Patterns", Anal. Chem., 72(17):4100-4109 (2000).
Hansen et al., "Microfluidics in structural biology: smaller, faster . . . better", Curr Opin Struct Biol. (2003) 13(5):538-544.
Harding et al., "DNA isolation using Methidium-Spermine-Sepharose", Meth Enzymol. (1992) 216: 29-39.
Harding et al., "Rapid isolation of DNA from complex biological samples using a novel capture reagent—methidium-spermine-sepharose", Nucl Acids Res. (1989) 17(17):6947-6958.
He et al., Microfabricated Filters for Microfluidic Analytical Systems, Analytical Chemistry, American Chemical Society, 1999, vol. 71, No. 7, pp. 1464-1468.
Heid et al., "Genome Methods—Real Time Quantitative PCR", Genome Res. (1996) 6(10):986-994.
Henry C.S. [Ed], "Microchip Capillary electrophoresis", Methods in Molecular Biology, Humana Press 339 (2006) Parts I-IV in 250 pages.
Herr et al., "Investigation of a miniaturized capillary isoelectric focusing (cIEF) system using a full-field detection approach", Solid State Sensor and Actuator Workshop, Hilton Head Island (2000), pp. 4-8.
Herr et al., "Miniaturized Isoelectric Focusing (μIEF) as a Component of a Multi-Dimensional Microfluidic System", Micro Total Analysis Systems (2001) pp. 51-53.
Herr et al., Miniaturized Capillary Isoelectric Focusing (cIEF): Towards a Portable High-Speed Separation Method. In Micro Total Analysis Systems (2000) Springer, Dordrecht; pp. 367-370.
Holland et al., "Point-of-care molecular diagnostic systems—past, present and future", Curr Opin Microbiol. (2005) 8(5):504-509.
Hong et al., "Integrated nanoliter systems", Nat Biotechnol. (2003) 21(10):1179-1183.
Hong et al., "Molecular biology on a microfluidic chip", J Phys.: Condensed Matter (2006) 18(18):S691-S701.
Hong et al., "Integrated Nucleic Acid Analysis in Parallel Matrix Architecture", in Integrated Biochips for DNA Analysis by Liu et al. [Eds], (2007) Chapter 8, pp. 107-116.
Horsman et al., "Forensic DNA Analysis on Microfluidic Devices: A Review", J Forensic Sci. (2007) 52(4):784-799.
Hsieh et al., "Enhancement of thermal uniformity for a microthermal cycler and its application for polymerase chain reaction", Sens Actuators B: Chemical. (2008) 130(2):848-856.
Huang et al., "Temperature Uniformity and DNA Amplification Efficiency in Micromachined Glass PCR Chip", TechConnect Briefs; Tech Proc. of the 2005 NSTI Nanotechnology Conference and Trade Show. (2005) vol. 1:452-455.
Huebner et al., "Microdroplets: A sea of applications?", Lab Chip. (2008) 8(8):1244-1254.

(56) References Cited

OTHER PUBLICATIONS

Ibrahim, et al., Real-Time Microchip PCR for Detecting Single-Base Differences in Viral and Human DNA, Analytical Chemistry, American Chemical Society, 1998, 70(9): 2013-2017.
International Search Report and Written Opinion dated Jun. 13, 2013 in Application No. PCT/US2013/024494, filed Feb. 1, 2013.
Iordanov et al., "PCR Array on Chip—Thermal Characterization", IEEE Sensors (2003) Conference Oct. 22-24, 2003; pp. 1045-1048.
Irawan et al., "Cross-Talk Problem on a Fluorescence Multi-Channel Microfluidic Chip System," Biomed Micro. (2005) 7(3):205-211.
Ji et al., "DNA Purification Silicon Chip", Sensors and Actuators A: Physical (2007) 139(1-2):139-144.
Jia et al., "A low-cost, disposable card for rapid polymerase chain reaction", Colloids Surfaces B: Biointerfaces (2007) 58:52-60.
Kaigala et al., "An inexpensive and portable microchip-based platform for integrated RT-PCR and capillary electrophoresis", The Analyst (2008) 133(3):331-338.
Kajiyama et al., "Genotyping on a Thermal Gradient DNA Chip", Genome Res. (2003) 13(3):467-475.
Kang et al., "Simulation and Optimization of a Flow-Through Micro PCR Chip", NSTI-Nanotech (2006) vol. 2, pp. 585-588.
Kantak et al., "Microfluidic platelet function analyzer for shear-induced platelet activation studies", 2nd Annual International IEEE-EMBS Special Topic Conference on Microtechnologies in Med and Biol. (May 2002) 5 pages.
Kantak et al., "Microfabricated cyclical electrical field flow fractionation", 7th International Conference on Miniaturized Chomical and Biochem Analysis Sys. (2003) pp. 1199-1202.
Kantak et al., "Platelet function analyzer: Shear activation of platelets in microchannels", Biomedical Microdevices (2003) 5(3):207-215.
Kantak et al., "Characterization of a microscale cyclical electrical field flow fractionation system", Lab Chip. (2006) 6(5):645-654.
Kantak et al., "Effect of carrier ionic strength in microscale cyclical electrical field-flow fractionation", Anal Chem. (2006) 78(8):2557-2564.
Kantak et al., "Improved theory of cyclical electrical field flow fractions", Electrophoresis (2006) 27(14):2833-2843.
Karunasiri et al., "Extraction of thermal parameters of microbolometer infrared detectors using electrical measurement", SPIE's Inter'l Symposium on Optical Science, Engineering, and Instrumentation; Proceedings (1998) vol. 3436, Infrared Technology and Applications XXIV; (1998) 8 pages.
Kelly et al., "Microfluidic Systems for Integrated, High-Throughput DNA Analysis," Analytical Chemistry, (2005), 97A-102A, Mar. 1, 2005, in 7 pages.
Khandurina et al., Microfabricated Porous Membrane Structure for Sample Concentration and Electrophoretic Analysis, Analytical Chemistry American Chemical Society, 1999, 71(9):1815-1819.
Khandurina et al., "Bioanalysis in microfluidic devices," J Chromatography A, (2002) 943:159-183.
Kim et al., "Reduction of Microfluidic End Effects In Micro-Field Flow Fractionation Channels", Proc. MicroTAS 2003, pp. 5-9.
Kim et al., "Multi-DNA extraction chip based on an aluminum oxide membrane integrated into a PDMS microfluidic structure", 3rd IEEE/EMBS Special Topic Conference on Microtechnology in Med and Biol. (May 2005).
Kim et al., "Electrohydrodynamic Generation and Delivery of Monodisperse Picoliter Droplets Using a Poly(dimethylsiloxane) Microchip", Anal Chem. (2006) 78: 8011-8019.
Kim et al., "Geometric optimization of a thin film ITO heater to generate a uniform temperature distribution", (2006), Tokyo, Japan; pp. 293-295; Abstract.
Kim et al., "Micro-Raman thermometry for measuring the temperature distribution inside the microchannel of a polymerase chain reaction chip", J Micromech Microeng. (2006) 16(3):526-530.
Kim et al., "Patterning of a Nanoporous Membrane for Multi-sample DNA Extraction", J Micromech Microeng. (2006) 16:33-39.
Kim et al., "Performance evaluation of thermal cyclers for PCR in a rapid cycling condition", Biotechniques. (2008) 44(4):495-505.
Kim et al., "Quantitative and qualitative analysis of a microfluidic DNA extraction system using a nanoporous AlO(x) membrane", Lab Chip. (2008) 8(9):1516-1523.
Kogi et al., "Microinjection-microspectroscopy of single oil droplets in water: an application to liquid/liquid extraction under solution-flow conditions", Anal Chim Acta. (2000) 418(2):129-135.
Kopf-Sill et al., "Creating a Lab-on-a-Chip with Microfluidic Technologies", in Integrated Microfabricated Biodevices: Advanced Technologies for Genomics, Drug Discovery, Bioanalysis, and Clinical Diagnostics (2002) Chapter 2; pp. 35-54.
Kopp et al., Chemical Amplification: Continuous-Flow PCR on a Chip, www.sciencemag.org, 1998, vol. 280, pp. 1046-1048.
Kricka L.J., "Microchips, Bioelectronic Chips, and Gene Chips—Microanalyzers for the Next Century", in Biochip Technology by Cheng et al. [Eds]; (2006) Chapter 1, pp. 1-16.
Krishnan et al., "Polymerase chain reaction in high surface-to-volume ratio SiO2 microstructures", Anal Chem. (2004) 76(22):6588-6593.
Kuo et al., "Remnant cationic dendrimers block RNA migration in electrophoresis after monophasic lysis", J Biotech. (2007) 129: 383-390.
Kuswandi et al., "Optical sensing systems for microfluidic devices: a review", Anal Chim Acta. (2007) 601(2):141-155.
Kutter et al., Solid Phase Extraction on Microfluidic Devices, J. Microcolumn Separations, John Wiley & Sons, Inc., 2000, 12(2): 93-97.
Labchem; Sodium Hydroxide, 0,5N (0.5M); Safety Data Sheet, 2015; 8 pages.
Lagally et al., Single-Molecule DNA Amplification and Analysis in an Integrated Microfluidic Device, Analytical Chemistry, American Chemical Society, 2001, 73(3): 565-570.
Lagally et al., "Genetic Analysis Using Portable PCR-CE Microsystem", Proceedings 7th International Conference on Miniaturized Chemical and Biochemical Analysis Systems (2003) pp. 1283-1286.
Lagally et al., "Integrated portable genetic analysis microsystem for pathogen/infectious disease detection", Anal Chem. (2004) 76(11):3152-3170.
Lauerman L.H., "Advances in PCR technology", Anim Health Res Rev. (2004) 5(2):247-248.
Lawyer et al., "High-level Expression, Purification, and Enzymatic Characterization of Full-length Thermus aquaticus DNA Polymerase and a Truncated Form Deficient in 5'to 3'Exonuclease Activity." Genome research (1993) 2(4):275-287.
Lee et al., "Submicroliter-volume PCR chip with fast thermal response and very power consumption", 7th International Conference on Miniaturized Chemical and Biochemical Analysis Systems, (2003) pp. 187-190.
Lee et al., "Bulk-micromachined submicroliter-volume PCR chip with very rapid thermal response and low power consumption", Lab Chip. (2004) 4(4):401-407.
Lewin et al., "Use of Real-Time PCR and Molecular Beacons to Detect Virus Replication in Human Immunodeficiency Virus Type 1-infected Individuals on Prolonged Effective Antiretroviral Therapy". J Virol. (1999) 73(7), 6099-6103.
Li et al., "Effect of high-aspect-ratio microstructures on cell growth and attachment", 1st Annual Inter'l IEEE-EMBS Special Topic Conference on Microtechnologies in Med and Biol. Proceedings Cat. No.00EX451; (Oct. 2000) Poster 66, pp. 531-536.
Li Pch., "Micromachining Methods et al." in Microfluidic Lab-on-a-Chip for Chemical and Biological Analysis and Discovery, CRC Press (2005), Chapter 2-3 to 2-5; pp. 10-49.
Li Pch., "Microfluidic Flow" in Microfluidic Lab-on-a-Chip for Chemical and Biological Analysis and Discovery, CRC Press (2005), Chapter 3, pp. 55-99.
Li Pch., "Detection Methods" in Microfluidic Lab-on-a-Chip for Chemical and Biological Analysis and Discovery, CRC Press (2005), Chapter 7, pp. 187-249.
Li Pch., "Applications to Nucleic Acids Analysis" in Microfluidic Lab-on-a-Chip for Chemical and Biological Analysis and Discovery, CRC Press (2005), Chapter 9; pp. 293-325.

(56) References Cited

OTHER PUBLICATIONS

Li et al., "A Continuous-Flow Polymerase Chain Reaction Microchip With Regional Velocity Control", J Microelectromech Syst. (2006) 15(1):223-236.
Liao et al., "Miniature RT-PCR system for diagnosis of RNA-based viruses," Nucl Acids Res. (2005) 33(18):e156 in 7 pages.
Lien et al., "Integrated reverse transcription polymerase chain reaction systems for virus detection", Biosens Bioelectron. (2007) 22(8):1739-1748.
Lien et al., "Microfluidic Systems Integrated with a Sample Pretreatment Device for Fast Nucleic-Acid Amplification", J Microelectro Sys. (2008) 17(2):288-301.
Lifesciences et al., "Microfluidics in commercial applications; an industry perspective." Lab Chip (2006) 6:1118-1121.
Lin et al., "Thermal Uniformity of 12-in Silicon Wafer During Rapid Thermal Processing by Inverse Heat Transfer Method," IEEE Transactions on Semiconductor Manufacturing, (2000) 13(4):448-456.
Lin et al., "Simulation and experimental validation of micro polymerase chain reaction chips", Sens Actuators B: Chemical. (2000) 71(1-2):127-133.
Linder et al., "Microfluidics at the Crossroad with Point-of-care Diagnostics", Analyst (2007) 132:1186-1192.
Liu et al., "Integrated portable polymerase chain reaction-capillary electrophoresis microsystem for rapid forensic short tandem repeat typing", Anal Chem. (2007) 79(5):1881-1889.
Liu et al. [Eds], Integrated Biochips for DNA Analysis—Biotechnology Intelligence Unit; Springer/Landes Bioscience (2007) ISBN:978-0-387-76758-1; 216 pages.
Livache et al., "Polypyrrole DNA chip on a Silicon Device: Example of Hepatitis C Virus Genotyping", Analytical Biochemistry, (1998) 255: 188-194.
Locascio et al., "ANYL 67 Award Address—Microfluidics as a tool to enable research and discovery in the life sciences", Abstract; The 236th ACS National Meeting (Aug. 2008); 2 pages.
Mahjoob et al., "Rapid microfluidic thermal cycler for polymerase chain reaction nucleic acid amplification", Inter'l J Heat Mass Transfer. (2008) 51(9-10):2109-2122.
Malitson, "Interspecimen Comparison of the Refractive Index of Fused Silica," J Optical Society of America, 55:1205-1209 (1965).
Manz et al., "Miniaturized Total Chemical Analysis Systems: a Novel Concept for Chemical Sensing," Sensors and Actuators B1, (1990) 244-248.
Marcus et al., "Parallel picoliter rt-PCR assays using microfluidics", Anal Chem. (2006) 78(3):956-958.
Mariella R.P. Jr., "Microtechnology", Thrust Area Report FY 96 UCRL-ID-125472; Lawrence Livermore National Lab., CA (Feb. 1997) Chapter 3 in 44 pages.
Mariella R., "Sample preparation: the weak link in microfluidics-based biodetection", Biomed Microdevices. (2008) 10(6):777-784.
Mastrangelo et al., Microfabricated Devices for Genetic Diagnostics. Proceedings of the IEEE (1998) 86(8):1769-1787.
Mascini et al., "DNA electrochemical biosensors", Fresenius J. Anal. Chem., 369: 15-22, (2001).
McMillan et al., "Application of advanced microfluidics and rapid PCR to analysis of microbial targets", In Proceedings of the 8th international symposium on microbial ecology (1999), in 13 pages.
Melin et al., "Microfluidic large-scale integration: the evolution of design rules for biological automation", Annu Rev Biophys Biomol Struct. (2007) 36:213-231.
Merugu et al., "High Throughput Separations Using a Microfabricated Serial Electric Split System" (2003), Proceedings of μTAS 2003, 7th International Conference on Miniaturized Chemical and Biochemical Analysis Systems, Oct. 5-9, 2003, Squaw Valley, California; 1191-1194, in 3 pages.
Meyers, R.A., Molecular Biology and Biotechnology: A Comprehensive Desk Reference; VCH Publishers, Inc. New York, NY; (1995) pp. 418-419.
Miao et al., "Low cost micro-PCR array and micro-fluidic integration on single silicon chip", Int'l J Comput Eng Science (2003) 4(2):231-234.
Miao et al., "Flip-Chip packaged micro-plate for low cost thermal multiplexing", Int'l J Comput Eng Science. (2003) 4(2):235-238.
Micheletti et al., "Microscale Bioprocess Optimisation", Curr Opin Biotech. (2006) 17:611-618.
MicroTAS 2005., "Micro Total Analysis Systems", Proceedings 9th Int. Conference on Miniaturized Systems for Chemistry and Life Sciences; Presentations/Posters/Articles for Conference; Boston, MA in Oct. 10-12, 2005 in 1667 pages.
MicroTAS 2007., "Micro Total Analysis Systems", Proceedings 11th Int. Conference on Miniaturized Systems for Chemistry and Life Sciences; Presentations/Posters/Articles for Conference; Paris, France in Oct. 7-11, 2007 in 1948 pages.
MicroTAS 2007., "Micro Total Analysis Systems", Advance Program for the Proceedings 11th Int. Conference on Miniaturized Systems for Chemistry and Life Sciences; Presentations/Posters/Articles for Conference; Paris, France in Oct. 7-11, 2007 in 42 pages.
Minco, "Conductive Heating Technologies for Medical Diagnostic Equipment," (2006) in 13 pages.
Mitchell et al., "Modeling and validation of a molded polycarbonate continuous-flow polymerase chain reaction device," Microfluidics, BioMEMS, and Medical Microsystems, Proc. SPIE (2003) 4982:83-98.
Myers et al., "Innovations in optical microfluidic technologies for point-of-care diagnostics", Lab Chip (2008) 8:2015-2031.
Nakagawa et al., Fabrication of amino silane-coated microchip for DNA extraction from whole blood, J of Biotechnology, Mar. 2, 2005, 116: 105-111.
Namasivayam et al., "Advances in on-chip photodetection for applications in miniaturized genetic analysis systems", J Micromech Microeng. (2004) 14:81-90.
Narayanan et al., "A microfabricated electrical SPLITT system," Lab Chip, (2006) 6:105-114.
Neuzil et al., "Disposable real-time microPCR device: lab-on-a-chip at a low cost, " Mol. Biosyst., (2006) 2:292-298.
Neuzil et al., "Ultra fast miniaturized real-time PCR: 40 cycles in less than six minutes," Nucleic Acids Research, (2006) 34(11)e77, in 9 pages.
Nguyen et al. [Eds], "Microfluidics for Internal Flow Control: Microfluidics" in Fundamentals and Applications of Microfluidics; 2nd Edition (2006) Introduction Chapter 1, pp. 1-9.
Nguyen et al. [Eds], "Microfluidics for Internal Flow Control: Microvalves" in Fundamentals and Applications of Microfluidics; (2006) 2nd Edition, Chapter 6, pp. 211-254.
Nguyen et al. [Eds], "Microfluidics for Internal Flow Control: Micropumps" in Fundamentals and Applications of Microfluidics; (2006) 2nd Edition, Chapter 7, pp. 255-309.
Nguyen et al. [Eds], "Microfluidics for Life Sciences and Chemistry: Microdispensers" in Fundamentals and Applications of Microfluidics; (2006) , Chapter 11, pp. 395-418.
Nguyen et al. [Eds], "Microfluidics for Life Sciences and Chemistry: Microreactors" in Fundamentals and Applications of Microfluidics; (2006) 2nd Edition, Chapter 13, pp. 443-477.
Ning et al., "Microfabrication Processes for Silicon and Glass Chips", in Biochip Technology, CRC-Press (2006) Chapter 2, pp. 17-38.
Northrup et al., "A MEMS-based Miniature DNA Analysis System," Lawrence Livermore National Laboratory, (1995), submitted to Transducers '95, Stockholm, Sweden, Jun. 25-29, 1995, in 7 pages (Prepublication).
Northrup et al., "Advantages Afforded by Miniaturization and Integration of DNA Analysis Instrumentation," Microreaction Technology, (1998) 278-288.
Northrup et al., A Miniature Analytical Instrument for Nucleic Acids Based on Micromachined Silicon Reaction Chambers, Analytical Chemistry, American Chemical Society, 1998, 70(5): 918-922.
Northrup et al., "A New Generation of PCR Instruments and Nucleic Acid Concentration Systems," in PCR Applications: Protocols for Functional Genomics, (1999), Chapter 8, pp. 105-125.

(56) References Cited

OTHER PUBLICATIONS

Northrup, "Microfluidics, A few good tricks," Nature materials (2004), 3:282-283.
Northrup et al., "Microfluidics-based integrated airborne pathogen detection systems," Abstract, Proceedings of the SPIE, (2006), vol. 6398, Abstract in 2 pages.
Oh et al., "World-to-chip microfluidic interface with built-in valves for multichamber chip-based PCR assays," Lab Chip, (2005), 5:845-850.
Oh K.W. et al., "A Review of Microvalves", J Micromech Microeng. (2006) 16:R13-R39.
Ohno et al., "Microfluidics: Applications for analytical purposes in chemistry and biochemistry," Electrophoresis (2008), 29:4443-4453.
Oleschuk et al., Trapping of Bead-Based Reagents within Microfluidic Systems: On-ChipSolid-Phase Extraction and Electrochromatography, Analytical Chemistry, American Chemical Society, 2000, 72(3): 585-590.
Pal et al., "Phase Change Microvalve for Integrated Devices", Anal Chem. (2004) 76: 3740-3748.
Pal et al., "An integrated microfluidic for influenza and other genetic analyses," Lab Chip, (2005), 5:1024-1032.
Palina et al., "Laser Assisted Boron Doping of Silicon Wafer Solar Cells Using Nanosecond and Picosecond Laser Pulses," 2011 37th IEEE Photovoltaic Specialists Conference, pp. 002193-002197, IEEE (2011).
Pamme, "Continuous flow separations in microfluidic devices," Lab Chip, (2007), 7:1644-1659.
Pang et al., "A novel single-chip fabrication technique for three-dimensional MEMS structures," Institute of Microelectronics, Tsinghua University, Beijing, P.R. China, (1998), IEEE, 936-938.
Pang et al., "The Study of Single-Chip Integrated Microfluidic System," Tsinghua University, Beijing, P.R. China, (1998), IEEE, 895-898.
Papautsky et al., "Effects of rectangular microchannel aspect ratio on laminar friction constant", in Microfluidic Devices and Systems II (1999) 3877:147-158.
Paulson et al., "Optical dispersion control in surfactant-free DNA thin films by vitamin B2 doping," Nature, Scientific Reports 8:9358 (2018) published at www.nature.com/scientificreports, Jun. 19, 2018.
Petersen, Kurt E., "Silicon as a Mechanical Material." Proceedings of the IEEE, (May 1982) 70(5):420-457.
Petersen et al., "Toward Next Generation Clinical Diagnostic Instruments: Scaling and New Processing Paradigms," Biomedical Microdevices (1998) 1(1):71-79.
Picard et al., Laboratory Detection of Group B Streptococcus for Prevention of Perinatal Disease, Eur. J. Clin. Microbiol. Infect. Dis., Jul. 16, 2004, 23: 665-671.
Plambeck et al., "Electrochemical Studies of Antitumor Antibiotics", J. Electrochem Soc.: Electrochemical Science and Technology (1984), 131(11): 2556-2563.
Poser et al., "Chip elements for fast thermocycling," Sensors and Actuators A, (1997), 62:672-675.
Pourahmadi et al., "Toward a Rapid, Integrated, and Fully Automated DNA Diagnostic Assay for Chlamydia trachomatis and Neisseria gonorrhea," Clinical Chemistry, (2000), 46(9):1511-1513.
Pourahmadi et al., "Versatile, Adaptable and Programmable Microfluidic Platforms for DNA Diagnostics and Drug Discovery Assays," Micro Total Analysis Systems, (2000), 243-248.
Raisi et al., "Microchip isoelectric focusing using a miniature scanning detection system," Electrophoresis, (2001), 22:2291-2295.
Raja et al., "Technology for Automated, Rapid, and Quantitative PCR or Reverse Transcription-PCR Clinical Testing," Clinical Chemistry, (2005), 51(5):882-890.
Reyes et al., "Micro Total Analysis Systems. 1. Introduction, Theory, and Technology", Anal Chem (2002) 74:2623-2636.
Roche et al. "Ectodermal commitment of insulin-producing cells derived from mouse embryonic stem cells" Faseb J (2005) 19: 1341-1343.
Rodriguez et al., "Practical integration of polymerase chain reaction amplification and electrophoretic analysis in microfluidic devices for genetic analysis," Electrophoresis, (2003), 24:172-178.
Rohsenow et al. [Eds.], Handbook of Heat Transfer, 3rd Edition McGraw-Hill Publishers (1998) Chapters 1 & 3; p. 108.
Roper et al., "Advances in Polymer Chain Reaction on Microfluidic Chips," Anal. Chem., (2005), 77:3887-3894.
Ross et al., Analysis of DNA Fragments from Conventional and Microfabricated PCR Devices Using Delayed Extraction MALDI-TOF Mass Spectrometry, Analytical Chemistry, American Chemical Society, 1998, 70(10): 2067-2073.
Ross et al., "Scanning Temperature Gradient Focusing for Simultaneous Concentration and Separation of Complex Samples," Micro Total Analysis Systems 2005, vol. 2, (2005), Proceedings of µTAS 2005, Ninth International Conference on Miniaturized Systems for Chemistry and Life Sciences, Oct. 9-13, 2005, Boston, Massachusetts; 1022-1024.
Ross et al., "Simple Device for Multiplexed Electrophoretic Separations Using Gradient Elution Moving Boundary Electrophoresis with Channel Current Detection," Anal. Chem., (2008), 80(24):9467-9474.
Sadler et al., "Thermal Management of BioMEMS: Temperature Control for Ceramic-Based PCR and DNA Detection Devices," IEEE Transactions on Components and Packaging Technologies, (2003) 26(2):309-316.
Sanchez et al., "Linear-After-The-Exponential (LATE)-PCR: An advanced method of asymmetric PCR and its uses in quantitative real-time analysis", PNAS (2004) 101(7): 1933-1938.
Sant et al., "An Integrated Optical Detector for Microfabricated Electrical Field Flow Fractionation System," Proceedings of µTAS 2003, 7th International Conference on Miniaturized Chemical and Biochemical Analysis Systems, Oct. 5-9, 2003, Squaw Valley, California; pp. 1259-1262.
Sant et al., "Geometric scaling effects on instrumental plate height in field flow fractionation", J Chromatography A (2006) 1104:282-290.
Sant H.J., "Reduction of End Effect-Induced Zone Broadening in Field-Flow Fractionation Channels", Anal Chem. (2006) 78:7978-7985.
Sant et al., "Microscale Field-Flow Fractionation: Theory and Practice", in Microfluidic Technologies for Miniaturized Analysis Systems. (2007) Chapter 12, p. 4710521.
Schäferling et al., "Optical technologies for the read out and quality control of DNA and protein microarrays," Anal Bioanal Chem, (2006), 385: 500-517.
Serpengüzel et al., "Microdroplet identification and size measurement in sprays with lasing images", Optics express (2002) 10(20):1118-1132.
Shackman et al., "Gradient Elution Moving Boundary Electrophoresis for High-Throughput Multiplexed Microfluidic Devices," Anal. Chem. (2007), 79(2), 565-571.
Shackman et al., "Temperature gradient focusing for microchannel separations," Anal Bioanal Chem, (2007), 387:155-158.
Shadpour et al., "Multichannel Microchip Electrophoresis Device Fabricated in Polycarbonate with an Integrated Contact Conductivity Sensor Array," Anal Chem., (2007), 79(3), 870-878.
Shen et al., "A microchip-based PCR device using flexible printed circuit technology," Sensors and Actuators B (2005), 105:251-258.
Shoffner et al., Chip PCR.I. Surface Passivation of Microfabricated Silicon-Glass Chips for PCR, Nucleic Acids Research, Oxford University Press, (1996) 24(2): 375-379.
Sia et al., "Microfluidic devices fabricated in poly(dimethylsiloxane) for biological studies," Electrophoresis, (2003), 24:3563-3576.
Sigurdson M., "AC Electrokinetic Enhancement for Assay Enhancement", ProQuest LLC (2008) Doctoral Thesis UMI Microform 3319791 in 24 pages.
Singh et al., "PCR thermal management in an integrated Lab on Chip," Journal of Physics: Conference Series, (2006), 34:222-227.
Situma et al., "Merging microfluidics with microarray-based bioassays", Biomol Engin. (2006) 23:213-231.

(56) References Cited

OTHER PUBLICATIONS

Smith, K. et al., "Comparison of Commercial DNA Extraction Kits for Extraction of Bacterial Genomic DNA from Whole-Blood Samples", Journal of Clinical Microbiology, vol. 41, No. 6 (Jun. 2003), pp. 2440-2443.
Smith et al., "(576d) Micropatterned fluid lipid bilayers created using a continuous flow microspotter for multi-analyte assays," (2007), Biosensors II, 2007 AIChE Annual Meeting, Nov. 8, 2007, Abstract in 2 pages.
Sommer et al., "Introduction to Microfluidics", in Microfluidics for Biological Applications by Tian et al. [Eds] (2008) Chapter 1, pp. 1-34.
Spitzack et al., "Polymerase Chain Reaction in Miniaturized Systems: Big Progress in Little Devices", in Methods in Molecular Biology—Microfluidic Techniques, Minteer S.D. [Ed.] Humana Press (2006), Chapter 10, pp. 97-129.
Squires et al., "Microfluidics: Fluid physics at the nanoliter scale", Rev Modern Phys. (2005) 77(3):977-1026.
Sundberg et al., "Solution-phase DNA mutation scanning and SNP genotyping by nanoliter melting analysis," Biomed Microdevices, (2007), 9:159-166, in 8 pages.
Tabeling, P. [Ed.], "Physics at the micrometric scale," in Introduction to Microfluidics (2005) Chapter 1, pp. 24-69.
Tabeling, P. [Ed.], "Hydrodynamics of Microfluidic Systems", in Introduction to Microfluidics; (2005) Chapter 2, pp. 70-129.
Tabeling, P. [Ed.], Introduction to Microfluidics; (2005) Chapters 5-7, pp. 216-297.
Tanaka et al., "Improved Method of DNA Extraction from Seeds Using Amine-Dendrimer Modified Magnetic Particles", Proceedings of the 74th Annual Meeting of the Electrochemical Society of Japan; Abstract #2E09 on p. 149, Mar. 29, 2007; Faculty of Engineering, Science University of Tokyo; 4 pages.
Taylor et al., Fully Automated Sample Preparation for Pathogen Detection Performed in a Microfluidic Cassette, in Micro Total Analysis Systems, Springer (2001), pp. 670-672.
Taylor et al., "Lysing Bacterial Spores by Sonication through a Flexible Interface in a Microfluidic System," Anal. Chem., (2001), 73(3):492-496.
Taylor et al., "Microfluidic Bioanalysis Cartridge with Interchangeable Microchannel Separation Components," (2001), The 11th International Conference on Solid-State Sensors and Actuators, Jun. 10-14, 2001, Munich, Germany; 1214-1247.
Taylor et al., "Disrupting Bacterial Spores and Cells using Ultrasound Applied through a Solid Interface," (2002), 2nd Annual International IEEE-EMBS Special Topic Conference on Microtechnologies in Medicine & Biology, May 2-4, 2002, Madison, Wisconsin; 551-555.
Thorsen et al., "Microfluidic Large-scale integration," Science, (2002), 298:580-584.
Toriello et al., "Multichannel Reverse Transcription-Polymerase Chain Reaction Microdevice for Rapid Gene Expression and Biomarker Analysis," Anal. Chem., (2006) 78(23):7997-8003.
Ugaz et al., "Microfabricated electrophoresis systems for DNA sequencing and genotyping applications," Phil. Trans. R. Soc. Lond. A, (2004), 362:1105-1129.
Ugaz et al., "PCR in Integrated Microfluidic Systems", in Integrated Biochips for DNA Analysis by Liu et al. [Eds]; (2007) Chapter 7, pp. 90-106.
Ullman et al., "Luminescent oxygen channeling assay (LOCI™): sensitive, broadly applicable homogeneous immunoassay method". Clin Chem. (1996) 42(9), 1518-1526.
Velten et al., "Packaging of Bio-MEMS: Strategies, Technologies, and Applications," IEEE Transactions on Advanced Packaging, (2005) 28(4):533-546.
Vinet et al., "Microarrays and microfluidic devices: miniaturized systems for biological analysis," Microelectronic Engineering, (2002), 61-62:41-47.
Wang, "Survey and Summary, from DNA Biosensors to Gene Chips", Nucleic Acids Research, 28(16):3011-3016, (2000).
Wang et al., "From biochips to laboratory-on-a-chip system", in Genomic Signal Processing and Statistics by Dougherty et al. [Eds]; (2005) Chapter 5, pp. 163-200.
Wang et al., "A disposable microfluidic cassette for DNA amplification and detection", Lab on a Chip (2006) 6(1):46-53.
Wang et al., "Micromachined Flow-through Polymerase Chain Reaction Chip Utilizing Multiple Membrane-activated Micropumps," (2006), MEMS 2006, Jan. 22-26, 2006, Istanbul, Turkey; 374-377.
Waters et al., Microchip Device for Cell Lysis, Multiplex PCR Amplification, and Electrophoretic Sizing, Analytical Chemistry, American Chemical Society, 1998, 70(1): 158-162.
Weigl, et al., Microfluidic Diffusion-Based Separation and Detection, www.sciencemag.org, 1999, vol. 283, pp. 346-347.
Woolley et al., "Functional integration of PCR amplification and capillary electrophoresis in a microfabricated DNA analysis device" Anal. Chem. (1996) vol. 68, pp. 4081-4086.
Wu et al., "Polycationic dendrimers interact with RNA molecules: polyamine dendrimers inhibit the catalytic activity of Candida ribozymes", Chem Commun. (2005) 3: 313-315.
Xiang et al., "Real Time PCR on Disposable PDMS Chip with a Miniaturized Thermal Cycler," Biomedical Microdevices, (2005), 7(4):273-279.
Xuan, "Joule heating in electrokinetic flow," Electrophoresis, (2008), 298:33-43.
Yang et al., "High sensitivity PCR assay in plastic micro reactors," Lab Chip, (2002), 2:179-187.
Yang et al., "An independent, temperature controllable-microelectrode array," Anal. Chem., (2004), 76(5):1537-1543.
Yang et al., "Cost-effective thermal isolation techniques for use on microfabricated DNA amplification and analysis devices," J Micromech Microeng, (2005), 15:221-230.
Yobas et al., Microfluidic Chips for Viral RNA Extraction & Detection, (2005), 2005 IEEE, 49-52.
Yobas et al., "Nucleic Acid Extraction, Amplification, and Detection on Si-Based Microfluidic Platforms," IEEE Journal of Solid-State Circuits, (2007), 42(8):1803-1813.
Yoon et al., "Precise temperature control and rapid thermal cycling in a micromachined DNA polymer chain reaction chip," J. Micromech. Microeng., (2002), 12:813-823.
Yoza et al., "Fully Automated DNA Extraction from Blood Using Magnetic Particles Modified with a Hyperbranched Polyamidoamine Dendrimer", J Biosci Bioeng, 2003, 95(1): 21-26.
Yoza et al., DNA extraction using bacterial magnetic particles modified with hyperbranched polyamidoamine dendrimer, J Biotechnol., Mar. 20, 2003, 101(3): 219-228.
Zhang et al., "Temperature analysis of continuous-flow micro-PCR based on FEA," Sensors and Actuators B, (2002), 82:75-81.
Zhang et al., "PCR Microfluidic Devices for DNA Amplification," Biotechnology Advances, 24:243-284 (2006).
Zhang et al., "Continuous-flow PCR Microfluidics for Rapid DNA Amplification Using Thin Film Heater with Low Thermal Mass," Analytical Letters, (2007), 40:1672-1685, in 15 pages.
Zhang et al., "Direct Adsorption and Detection of Proteins, Including Ferritin, onto Microlens Array Patterned Bioarrays," J Am Chem Soc., (2007), 129:9252-9253.
Zhang et al., "Micropumps, microvalves, and micromixers within PCR microfluidic chips: Advances and trends," Biotechnology Advances, (2007), 25:483-514.
Zhang et al., "Miniaturized PCR chips for nucleic acid amplification and analysis: latest advances and future trends," Nucl Acids Res., (2007) 35(13):4223-4237.
Zhao et al., "Heat properties of an integrated micro PCR vessel," Proceedings of SPIE, (2001), International Conference on Sensor Technology, 4414:31-34.
Zhou et al., "Cooperative binding and self-assembling behavior of cationic low molecular-weight dendrons with RNA molecules", Org Biomol Chem. (2006) 4(3): 581-585.
Zhou et al., "PAMAM dendrimers for efficient siRNA delivery and potent gene silencing", Chem Comm. (Camb.) (2006) 22: 2362-2364.
Zou et al., "A Micromachined Integratable Thermal Reactor," technical digest from International Electron Devices Meeting, IEEE, Washington, D.C., Dec. 2-5, 2001 (6 pages).

(56) References Cited

OTHER PUBLICATIONS

Zou et al., "Micro-assembled multi-chamber thermal cycler for low-cost reaction chip thermal multiplexing," Sensors and Actuators A, (2002), 102:114-121.
Zou et al., "Miniaturized Independently Controllable Multichamber Thermal Cycler," IEEE Sensors Journal, (2003), 3(6):774-780.
Petition for Inter Partes Review of U.S. Pat. No. 7,998,708 (Paper 1 in IPR2019-00488) dated Dec. 20, 2018 (94 pages).
Declaration of Bruce K. Gale, Ph.D. (Exhibit 1001 in IPR2019-00488 and IPR2019-00490) dated Dec. 20, 2018 (235 pages).
Patent Owner Preliminary Response to Petition for Inter Partes Review of U.S. Pat. No. 7,998,708 and Exhibit List (Papers 5 and 6 in IPR2019-00488) dated Apr. 18, 2019 (79 pages).
Decision instituting Inter Partes Review of U.S. Pat. No. 7,998,708 (Paper 8 in IPR2019-00488) dated Jul. 16, 2019 (20 pages).
Petition for Inter Partes Review of U.S. Pat. No. 8,323,900 (Paper 1 in IPR2019-00490) dated Dec. 20, 2018 (85 pages).
Declaration of Michael G. Mauk, Ph. D. in Support of Patent Owner Preliminary Responses in IPR2019-00488 and IPR2019-00490 dated Apr. 18, 2019 (43 pages).
Patent Owner Preliminary Response to Petition for Inter Partes Review of U.S. Pat. No. 8,323,900 and Exhibit List (Papers 5 and 6 in IPR2019-00490) dated Apr. 18, 2019 (73 pages).
Decision instituting Inter Partes Review of U.S. Pat. No. 8,323,900 (Paper 8 in IPR2019-00490) dated Jul. 16, 2019 (23 pages).
Patent Owner's Response in Inter Partes Review of U.S. Pat. No. 8,323,900 and Exhibit List (Paper 25 in IPR2019-00490) dated Oct. 16, 2019 (80 pages).
Patent Owner's Response in Inter Partes Review of U.S. Pat. No. 7,998,708 and Exhibit List (Paper 25 in IPR 2019-00488) dated Oct. 16, 2019 (93 pages).
Transcript of Deposition of Bruce K. Gale, Ph.D., in Support of Patent Owner's Responses (Exhibit 2012 in IPR2019-00488 and IPR2019-00490), taken Sep. 24, 2019 (124 pages).
Declaration of M. Allen Northrup, Ph.D. in Support of Patent Owner's Responses (Exhibit 2036 in IPR2019-00488 and IPR2019-00490) dated Oct. 16, 2019 (365 pages).
Petitioner's Reply to Patent Owner's Response to Petition in Inter Partes Review of U.S. Pat. No. 7,998,708 and Exhibit List (Paper 32 in IPR 2019-00488) dated Jan. 31, 2020 (34 pages).
Petitioner's Reply to Patent Owner's Response to Petition in Inter Partes Review of U.S. Pat. No. 8,323,900 and Exhibit List (Paper 32 in IPR 2019-00490) dated Jan. 31, 2020 (35 pages).
Second Declaration of Bruce K. Gale, Ph.D. (Exhibit 1026 in IPR2019-00488 and IPR2019-00490) dated Jan. 31, 2020 (91 pages).
Transcript of Deposition of M. Allen Northrup, Ph.D., (Exhibit 1027 in IPR2019-00488 and IPR2019-00490), taken Dec. 19, 2019 (109 pages).
Patent Owner's Sur-Reply in Inter Partes Review of U.S. Pat. No. 8,323,900 (Paper 42 in IPR2019-00490) dated Mar. 12, 2020 (39 pages).
Patent Owner's Sur-Reply in Inter Partes Review of U.S. Pat. No. 7,998,708 (Paper 43 in IPR 2019-00488) dated Mar. 12, 2020 (41 pages).
Transcript of Second Deposition of Bruce K. Gale, Ph.D., (Exhibit 2068 in IPR2019-00488 and IPR2019-00490), taken Feb. 19, 2020 (352 pages).
Complaint filed by *Becton, Dickinson et al*., v. *NeuModx Molecular, Inc*. on Jun. 18, 2019 in U.S. District Court, Delaware, Case #1:19-cv-01126-LPS, Infringement Action involving U.S. Pat. Nos. 7,998,708; 8,273,308; 8,323,900; 8,415,103; 8,703,069; and 8,709,787 (29 pages).
Answer to Complaint filed by NeuModx Molecular, Inc. on Aug. 9, 2019 in U.S. District Court, Delaware, Case #1:19-cv-01126-LPS (24 pages).
Amended Answer to Complaint filed by NeuModx Molecular, Inc. on Oct. 4, 2019 in U.S. District Court, Delaware, Case #1:19-cv-01126-LPS (31 pages).
Anderson et al., "Microfluidic biochemical analysis system" Proc. 1997 IEEE Int. Conf. Solid-State Sens. Actuat. (1997) pp. 477-480.
Anderson et al., "Advances in Integrated Genetic Analysis" Micro Total Analysis Systems '98 Conference Proceedings, D. Kluwer Academic Publishers (1998) in 6 pages.
Anderson et al., "A Miniature Integrated Device for Automated Multistep Genetic Assays" Nucleic Acids Research (2000) 28(12), i-vi.
Burns et al., "Microfabricated Structures for Integrated DNA Analysis" Proc. Natl. Acad. Sci. USA (May 1996) 93: 5556-5561.
Harrison et al., "Capillary Electrophoresis and Sample Injection Systems Integrated on a Planar Glass Chip", Anal. Chem., (1992) 64: 1926-1932.
Hsueh et al., "A microfabricated, electrochemiluminescence cell for the detection of amplified DNA" Proc. 1995 IEEE Int. Conf. Solid-State Sens. Actuators (1995) pp. 768-771.
Hsueh et al., "DNA quantification with an electrochemiluminescence microcell" Proc. 1997 IEEE Int. Conf. Solid-State Sens. Actuators (1997) pp. 175-178.
Jiang et al., "Directing cell migration with asymmetric micropatterns" Proc. Natl. Acad. Sci. USA (2005) 102, 975-978.
Lagally et al., "Monolithic integrated microfluidic DNA amplification and capillary electrophoresis analysis system" Sensors and Actuators B (2000) 63:138-146.
Manz et al., "Design of an open-tubular column liquid chromatograph using silicon chip technology" Sensors and Actuators B (1990) 1:249-255.
Manz et al., "Planar chips technology for miniaturization and integration of separation techniques into monitoring systems: Capillary electrophoresis on a chip" Journal of Chromatography A (1992) 593:253-258.
Northrup et al., "A MEMS-based Miniature DNA Analysis System." Transducers '95—Eurosensors in Proc. 1995 (8th) IEEE Int. Conf. Solid-State Sens. Actuators, pp. 764-767.
Rhee et al., "Drop Mixing in a Microchannel for Lab-on-a-Chip Applications" Langmuir (2008) 24 (2): 590-601.
Sammarco et al., "Thermocapillary Pumping of Discrete Drops in Microfabricated Analysis Devices" AlChE Journal (1999) 45(2): 350-366.
Taylor et al., "Optimization of the performance of the polymerase chain reaction in silicon-based microstructures" Nucleic Acids Res. (1997) vol. 25, pp. 3164-3168.
Terry et al., "A Gas Chromatographic Air Analyzer Fabricated on a Silicon Wafer" IEEE T Electron Dev (1979) 26:1880-1886.
U.S. Appl. No. 60/491,264, filed Jul. 31, 2003 (41 pages).
U.S. Appl. No. 60/491,269, filed Jul. 31, 2003 (52 pages).
U.S. Appl. No. 60/491,539, filed Aug. 1, 2003 (45 pages).
U.S. Appl. No. 60/553,553, filed Mar. 17, 2004 (49 pages).
U.S. Appl. No. 60/726,066, filed Oct. 11, 2005 (54 pages).
U.S. Appl. No. 60/786,007, filed Mar. 24, 2006 (223 pages).
U.S. Appl. No. 60/859,284, filed Nov. 14, 2006 (114 pages).
Whitesides G.M., "The origins and the future of microfluidics" Nature (2006) 442(7101):368-373.
Woias P., "Micropumps—past, progress and future prospects" Sensors and Actuators B (2005) 105, 28-38.
Wu et al., "Fabrication of Complex Three-dimensional Microchannel Systems in PDMS" J. Am. Chem. Soc. (2003) 125, 554-559.
Zhang et al., "Parallel DNA amplification by convective polymerase chain reaction with various annealing temperatures on a thermal gradient device," Analytical Biochemistry, (2009) 387:102-112.
Record of Oral Hearing in IPR2019-00488 and IPR2019-00490 held Apr. 21, 2020 (80 pages); Petitioner's Demonstratives for Oral Hearing in IPR2019-00488 and IPR2019-00490 held Apr. 21, 2020 (72 pages); Patent Owner's Demonstratives for Oral Hearing in IPR2019-0488 and IPR2019-00490 held Apr. 21, 2020 (88 pages); Patent Owner's Objections to Petitioner's Oral Hearing Demonstratives in IPR2019-00488 and IPR2019-00490 dated Apr. 16, 2020 (4 pages).
Petition for Inter Partes Review of U.S. Pat. No. 8,273,308 (Paper 2 in IPR2020-01083) dated Jun. 12, 2020 (104 pages).
Petition for Inter Partes Review of U.S. Pat. No. 8,273,308 (Paper 2 in IPR2020-01091) dated Jun. 12, 2020 (105 pages).

(56) References Cited

OTHER PUBLICATIONS

Petition for Inter Partes Review of U.S. Pat. No. 8,803,069 (Paper 2 in IPR2020-01095) dated Jun. 12, 2020 (84 pages).
Petition for Inter Partes Review of U.S. Pat. No. 8,803,069 (Paper 3 in IPR2020-01100) dated Jun. 12, 2020 (83 pages).
Petition for Inter Partes Review of U.S. Pat. No. 8,709,787 (Paper 2 in IPR2020-01132) dated Jun. 18, 2020 (96 pages).
Petition for Inter Partes Review of U.S. Pat. No. 8,415,103 (Paper 2 in IPR2020-01133) dated Jun. 18, 2020 (96 pages).
Petition for Inter Partes Review of U.S. Pat. No. 8,709,787 (Paper 2 in IPR2020-01137) dated Jun. 19, 2020 (86 pages).
Petition for Inter Partes Review of U.S. Pat. No. 8,415,103 (Paper 2 in IPR2020-01136) dated Jun. 19, 2020 (85 pages).
Declaration of Mark A. Burns, Ph.D. (Exhibit N1001 in IPR2020-01083, IPR2020-01091, IPR2020-01095 and IPR2020-01100) dated Jun. 12, 2020 (378 pages).
Declaration of Mark A. Burns, Ph.D. (Exhibit N1101 in IPR2020-01132 and IPR2020-01133) dated Jun. 17, 2020 (253 pages).
Declaration of Mark A. Burns, Ph.D. (Exhibit N1201 in IPR2020-01136 and IPR2020-01137) dated Jun. 19, 2020 (205 pages).
Judgment/Final Written Decision in Inter Partes Review of U.S. Pat. No. 7,998,708 (Paper No. 52 in IPR2019-00488) dated Jul. 14, 2020 (43 pages).
Judgment/Final Written Decision in Inter Partes Review of U.S. Pat. No. 8,323,900 (Paper No. 51 in IPR2019-00490) dated Jul. 14, 2020 (43 pages).
First Amended and Supplemental Complaint filed by Becton, Dickinson and Company et al. on Jun. 25, 2020 in U.S. District Court, Delaware, Case #1:19-cv-01126-LPS, InfringementAction involving U.S. Pat. Nos. 7,998,708; 8,273,308; 8,323,900; 8,415,103; 8,703,069; 8,709,787; 10,494,663; 10,364,456; 10,443,088; 10,604,788; 10,625,261; 10,625,262; and 10,632,466 (55 pages).
Answer to Amended and Supplemental Complaint filed by NeuModx Molecular, Inc. on Jul. 16, 2020 in U.S. District Court, Delaware, Case #1:19-cv-01126-LPS (42 pages).
Petitioner's Notice of Appeal in Inter Partes Review of U.S. Pat. No. 7,998,708 (Paper No. 54 in IPR2019-00488) dated Sep. 9, 2020 (48 pages).
Petitioner's Notice of Appeal in Inter Partes Review of U.S. Pat. No. 8,323,900 (Paper No. 53 in IPR2019-00490) dated Sep. 9, 2020 (48 pages).
Patent Owner Preliminary Response to Petition for Inter Partes Review of U.S. Pat. No. 8,703,069 (Paper 13 in IPR2020-01095) dated Sep. 17, 2020 (77 pages).
Patent Owner Preliminary Response to Petition for Inter Partes Review of U.S. Pat. No. 8,273,308 (Paper 13 in IPR2020-01091) dated Sep. 17, 2020 (70 pages).
Patent Owner Preliminary Response to Petition for Inter Partes Review of U.S. Pat. No. 8,703,069 (Paper 14 in IPR2020-01100) dated Sep. 17, 2020 (59 pages).
Declaration of M. Allen Northrup, Ph.D. in Support of Patent Owner Preliminary Responsesin IPR2020-01091, IPR2020-01095 and IPR2020-01100 (Exhibit H2003) dated Sep. 16, 2020 (137 pages).
Patent Owner Preliminary Response to Petition for Inter Partes Review of U.S. Pat. No. 8,273,308 (Paper 13 in IPR2020-01083) dated Oct. 22, 2020 (88 pages).
Declaration of M. Allen Northrup, Ph.D. in support of Patent Owner Preliminary Responses in IPR2020-01083, IPR2020-01091, IPR2020-01095 and IPR2020-01100 (Exhibit H2003) dated Oct. 21, 2020 (171 pages).
Defendant NeuModx's Initial Invalidity Contentions filed Sep. 30, 2020 in U.S. District Court, Delaware, Case #1:19-cv-01126-LPS (47 pages).
Petition for Inter Partes Review of U.S. Pat. No. 10,625,262 (Paper 2 in IPR2021-00250) dated Nov. 25, 2020 (107 pages).
Petition for Inter Partes Review of U.S. Pat. No. 10,625,261 (Paper 2 in IPR2021-00251) dated Nov. 25, 2020 (117 pages).
Petition for Inter Partes Review of U.S. Pat. No. 10,632,466 (Paper 2 in IPR2021-00253) dated Nov. 25, 2020 (121 pages).
Declaration of Mark A. Burns, Ph.D. (Exhibit N1001 in IPR2021-00250, IPR2021-00251 and IPR2021-00253) dated Nov. 24, 2020 (311 pages).
Declaration of James L. Mullins, Ph.D. (Exhibit N1029 in IPR2021-00250, IPR2021-00251, and IPR2021-00253) dated Nov. 18, 2020 (54 pages).
Decision Denying Institution of Inter Partes Review of U.S. Pat. No. 8,273,308 (Paper 14 in IPR2020-01091) dated Dec. 4, 2020 (21 pages).
Decision Denying Institution of Inter Partes Review of U.S. Pat. No. 8,703,069 (Paper 14 in IPR2020-01095) dated Dec. 4, 2020 (22 pages).
Decision Denying Institution of Inter Partes Review of U.S. Pat. No. 8,703,069 (Paper 15 in IPR2020-01100) dated Dec. 4, 2020 (19 pages).
Defendant NeuModx's Joint Claim Construction Chart filed Oct. 21, 2020 in U.S. District Court, Delaware, Case #1:19-cv-01126-LPS (25 pages).
Defendant NeuModx's Amended Answer, Affirmative Defenses, and Counterclaims to Plaintiffs' First Amended and Supplemental Complaint filed Dec. 11, 2020 in U.S. District Court, Delaware, Case #1:19-cv-01126-LPS (43 pages).
BDProbeTec™ ET Neisseria gonorrhoeae Amplified DNA Assay Package Insert, Jul. 2010 (13 pages).
BDProbeTec™ ET System Brochure, Aug. 2010 (9 pages).
Gill et al., "Nucleic Acid Isothermal Amplification Technologies—A Review", Nucleosides Nucleotides Nucleic Acids, (2008) 27(3): 224-243.
Rush et al., "Dispersion by Pressure-Driven Flow in Serpentine Microfluidic Channels", Ind Eng Chem Res., (2002) 41: 4652-4662.
Walker et al., "Strand displacement amplification—an isothermal, in vitro DNA amplification technique", Nucleic Acids Res. (1992) 20(7): 1691-1696.
Decision Denying Institution of Inter Partes Review of U.S. Pat. No. 8,273,308 (Paper 14 in IPR2020-01083) dated Jan. 7, 2021 (24 pages).
Patent Owner's Preliminary Response to Petition for Inter Partes Review of U.S. Pat. No. 8,415,103 (Paper 20 in IPR2020-01133) dated Jan. 20, 2021 (67 pages).
Patent Owner's Preliminary Response to Petition for Inter Partes Review of U.S. Pat. No. 8,709,787 (Paper 19 in IPR2020-01132) dated Jan. 20, 2021 (78 pages).
Declaration of M. Allen Northrup, Ph.D. in support of Patent Owner Preliminary Responsesin IPR2020-01132 and IPR2020-01133 (Exhibit H2016) dated Jan. 20, 2021 (154 pages).
Patent Owner's Preliminary Response to Petition for Inter Partes Review of U.S. Pat. No. 8,415,103 (Paper 19 in IPR2020-01136) dated Jan. 20, 2021 (77 pages).
Patent Owner's Preliminary Response to Petition for Inter Partes Review of U.S. Pat. No. 8,709,787 (Paper 19 in IPR2020-01137) dated Jan. 20, 2021 (69 pages).
Declaration of M. Allen Northrup, Ph.D. in support of Patent Owner Preliminary Responses in IPR2020-01136 and IPR2020-01137 (Exhibit H2016) dated Jan. 20, 2021 (111 pages).
Opening Brief [Corrected] of Appellants Qiagen North American Holdings, Inc. and NeuMoDx Molecular Inc. in Appeals to IPR2019-00488, IPR2019-00490, IPR2019-01493 and IPR2019-01494 filed Jan. 22, 2021 in U.S. Court of Appeals for the Federal Circuit Case Nos. 20-2249, 20-2250, 20-2273 and 20-2276 (82 pages).
Decision Granting Institution of Inter Partes Review of U.S. Pat. No. 8,709,787 (Paper 20 in IPR2020-01132) dated Apr. 19, 2021 (33 pages).
Decision Denying Institution of Inter Partes Review of U.S. Pat. No. 8,415,103 (Paper 21 in IPR2020-01133) dated Apr. 19, 2021 (24 pages).
Decision Denying Institution of Inter Partes Review of U.S. Pat. No. 8,415,103 (Paper 20 in IPR2020-01136) dated Apr. 19, 2021 (19 pages).
Decision Denying Institution of Inter Partes Review of U.S. Pat. No. 8,709,787 (Paper 20 in IPR2020-01137) dated Apr. 19, 2021 (14 pages).

(56) References Cited

OTHER PUBLICATIONS

Patent Owner's Preliminary Response to Petition for Inter Partes Review of U.S. Pat. No. 10,625,262 (Paper 6 in IPR2021-00250) dated Apr. 19, 2021 (71 pages).
Patent Owner's Preliminary Response to Petition for Inter Partes Review of U.S. Pat. No. 10,625,261 (Paper 6 in IPR2021-00251) dated Apr. 19, 2021 (82 pages).
Patent Owner's Preliminary Response to Petition for Inter Partes Review of U.S. Pat. No. 10,632,466 (Paper 6 in IPR2021-00253) dated Apr. 19, 2021 (66 pages).
Declaration of James P. Landers, Ph.D. in support of Patent Owner Preliminary Responses in IPR2021-00250, IPR2021-00251, and IPR2021-00253 (Exhibit H2003) dated Apr. 19, 2021 (189 pages).
Second Amended and Supplemental Complaint filed by Becton, Dickinson and Company et al. on Feb. 25, 2021 in U.S. District Court, Delaware, Case #1:19-cv-01126-LPS (75 pages).
Defendant NeuMoDx's First Supplemental Invalidity Contentions filed Mar. 17, 2021 in U.S. District Court, Delaware, Case #1:19-cv-01126-LPS (55 pages).
Defendant NeuModx's Answer, Affirmative Defenses, and Counterclaims to Plaintiffs'Second and Supplemental Complaint filed Mar. 18, 2021 in U.S. District Court, Delaware, Case #1:19-cv-01126-LPS (67 pages).
Plaintiffs' Answer and/or Reply to Defendants' Counterclaims and Counterclaims-In-Reply filed Apr. 22, 2021 in U.S. District Court, Delaware, Case #1:19-cv-01126-LPS (127 pages).
Claim Construction (Markman) Order dated May 10, 2021 in in U.S. District Court, Delaware, Case #1:19-cv-01126-LPS (30 pages).

* cited by examiner

Automated Instrument with Independent Workstations and a Shared Service

Fig. 5

Level 2 Index: Run Compatible?

| Level 1 Index: Rack Compatible? | 1 | 2 | 3 | 4 | 5 | 6 | 7 | 8 | 9 | 10 |
|---|---|---|---|---|---|---|---|---|---|---|
| 1 | | N | N | N | N | Y | Y | N | N | N |
| 2 | N | | Y | Y | N | N | N | Y | Y | N |
| 3 | N | N | | Y | N | N | N | Y | Y | N |
| 4 | N | N | Y | | N | N | N | Y | Y | N |
| 5 | N | N | N | N | | N | N | N | N | N |
| 6 | N | N | N | N | N | | N | N | N | N |
| 7 | N | N | N | N | N | Y | | N | N | N |
| 8 | N | N | N | N | N | N | N | | Y | N |
| 9 | N | N | N | N | N | N | N | N | | N |
| 10 | N | N | N | N | N | N | N | N | N | |

Tests with the same Level 1 Index are by definition rack and run compatible

EXTERNAL FILES FOR DISTRIBUTION OF MOLECULAR DIAGNOSTIC TESTS AND DETERMINATION OF COMPATIBILITY BETWEEN TESTS

CROSS REFERENCE TO RELATED APPLICATIONS

The present application is a continuation of U.S. application Ser. No. 13/757,392, entitled "EXTERNAL FILES FOR DISTRIBUTION OF MOLECULAR DIAGNOSTIC TESTS AND DETERMINATION OF COMPATIBILITY BETWEEN TESTS," filed Feb. 1, 2013, which claims priority to U.S. Provisional Application Ser. No. 61/594,867, entitled "EXTERNAL FILES FOR DISTRIBUTION OF MOLECULAR DIAGNOSTIC TESTS AND DETERMINATION OF COMPATIBILITY BETWEEN TESTS," filed Feb. 3, 2012, both of which are herein incorporated by reference in their entirety.

BACKGROUND OF THE INVENTION

Field of the Invention

Embodiments disclosed herein relate to methods and systems for performing an automated assay, and particularly to performing a plurality of assays on a plurality of samples on an automated instrument.

Description of the Related Art

The medical diagnostics industry is a critical element of today's healthcare infrastructure. In the last decade, the use of nucleic acid based assays for diagnostic testing has become increasingly more common. The automation of processing and testing samples in diagnostic testing is appealing, as it minimizes experimental variability and reduces the need for highly trained technicians. In addition to benefits in the field of diagnostics, automation of processing and testing samples has facilitated high throughput testing.

Understanding that processing samples for purposes such as diagnostic testing or high throughput testing may break down into several key steps, it is often desirable to automate one or more steps. For example, in the context of diagnostics, a biological sample, such as those obtained from a patient, can be used in nucleic acid amplification assays in order to amplify a target nucleic acid (e.g., DNA, RNA, or the like) of interest. Once amplified, the presence of a target nucleic acid, or amplification product of a target nucleic acid (e.g., a target amplicon) can be detected, wherein the presence of a target nucleic acid and/or target amplicon is used to identify and/or quantify the presence of a target (e.g., a target microorganism or the like). Often, nucleic acid amplification assays involve multiple steps, which can include nucleic acid extraction, nucleic acid amplification, and detection. It is desirable to automate certain steps of these processes.

There is a need for improved methods and devices for carrying out assays on multiple samples in parallel. The embodiments described herein address this need and can advantageously be used in clinical and research settings.

SUMMARY OF THE INVENTION

The present technology relates to methods and systems for performing an automated assay, and particularly to performing a plurality of assays on a plurality of samples on an automated instrument. In some embodiments of the present technology, such methods and systems can permit the concurrent performance of discrete assay workflows on an instrument when the assay workflows are compatible, and can prevent the concurrent performance of incompatible assays within the same workstation. Some embodiments relate to performing a plurality of user-defined protocols (UDP) on an automated instrument. Some embodiments relate to performing a plurality of assay definition files (ADF) developed by an assay manufacturer. Some embodiments relate to performing one or more UDPs, optionally in combination with one or more ADFs, concurrently on the same automated instrument.

In some embodiments of the technology presented herein, methods of performing an automated assay on a plurality of samples are provided that allow for improved reliability and ease of use when performing an assay on an automated instrument. The methods can include providing an automated instrument comprising a first workstation and a second workstation, each of the first and second workstations configured to receive and processes a plurality of samples according to a plurality of different automated assay workflows, wherein each different automated assay workflow has an associated unique assay definition or user-defined protocol file; determining whether two discrete assay workflows are compatible or incompatible with each other for concurrent processing on the automated instrument; and performing the discrete assay workflows concurrently on the instrument when the assays are compatible.

In some embodiments, the assay definition or user defined protocol file can comprise a first level compatibility index value, and wherein the determining step can comprise: (a) selecting a first assay from among a first list of available assays; and (b) evaluating which of a plurality of other available assays have an assay definition file comprising the same first level compatibility index value as the first assay, wherein the same first level compatibility index value is indicative of first-level compatibility.

In some embodiments, the evaluating step can comprise (b1) identifying any assays which have first level compatibility index values different from the first compatibility index value of the first assay; and (b2) providing a second list of second assays, wherein the second list excludes any assay having a first level compatibility index value different from the first compatibility index value of the first assay.

In some embodiments, each assay definition file can comprise a second level compatibility index value, and wherein the determining step further can comprise (c) evaluating which of a plurality of other available assays have an assay definition file comprising the same second level compatibility index value as the first assay, wherein the same second level compatibility index value is indicative of second-level compatibility.

In some embodiments, the evaluating step can comprise (c1) identifying any assays which have second level compatibility index values different from the second compatibility index value of the first assay; and (c2) providing a second list of second assays, wherein the second list excludes any assay having a second level compatibility index value different from the second compatibility index value of the first assay.

In some embodiments, the first level compatibility can comprise compatibility of performing two assays concurrently at a single workstation, the parameters selected from the group consisting of: incubation time, lysis time, reagent volume, reagent type, incubation temperature, lysis temperature, workstation time demands, regulatory classification, business considerations, and a combination thereof.

In some embodiments, the second level compatibility can comprise compatibility of performing two assays concurrently on the automated instrument, the parameters selected from the group consisting of: regulatory classification, workflow incompatibility, business considerations, and a combination thereof.

In some embodiments, the instrument prevents the concurrent performance of incompatible assays within the same workstation when the first compatibility indexes are different. In some embodiments, the two discrete assay workflows are performed in the same workstation. In some embodiments, the instrument is prevented from concurrently performing assays with different second compatibility index values. In some embodiments, two assays have the same first level compatibility index value and have different second level compatibility index values. In some embodiments, the difference in the second level compatibility index values can comprise a business reason. In some embodiments, the difference in the second level compatibility index values can comprise a regulatory classification.

In some embodiments, if the assays are compatible, the method can further comprise one or more of the following (d) initiating an assay-specific sample preparation script on the instrument; (e) comparing identifying indicia on a consumable package to a set of assay-specific identifying data stored on the instrument; (f) initiating an assay-specific load cartridge script on the instrument; (g) comparing levels of detectable signals fluorescence ratios in a loaded cartridge to a set of assay-specific detectable signal data stored on the instrument to determine whether the cartridge was successfully loaded; (h) initiating an assay-specific reaction script on the instrument; (i) initiating an assay-specific data analysis algorithm on the instrument; or (j) deriving a final call for the assay, based on one or more assay-specific result algorithms or scripts.

In some embodiments, the assay protocol can comprise a reaction selected from the group selected from: Polymerase Chain Reaction (PCR), Transcription Mediated Amplification (TMA), Oligonucleotide Ligation Assay (OLA), Ligase Chain Reaction (LCR), Rolling Circle Amplification (RCA), Strand Displacement Amplification (SDA), and a hybridization reaction.

Also presented herein is a system for performing an automated assay, the system comprising an automated instrument comprising a first workstation and a second workstation, each of the first and second workstations configured to receive and processes a plurality of samples according to a plurality of different automated assay workflows, wherein each different automated assay workflow has an associated unique assay definition file or user-defined protocol file; a processor; a storage capacity; and a program for performing an automated assay, the program comprising instructions for determining whether two discrete assay workflows are compatible or incompatible with each other for concurrent processing on the automated instrument; and performing the discrete assay workflows concurrently on the instrument when the assays are compatible.

In some embodiments of the above system, the assay definition file or user defined protocol file can comprise a first level compatibility index value, and wherein the determining step can comprise: (a) selecting a first assay from among a first list of available assays; and (b) evaluating which of a plurality of other available assays have an assay definition file comprising the same first level compatibility index value as the first assay, wherein the same first level compatibility index value is indicative of first-level compatibility.

In some embodiments of the above system, the evaluating step can comprise (b1) identifying any assays which have first level compatibility index values different from the first compatibility index value of the first assay; and (b2) providing a second list of second assays, wherein the second list excludes any assay having a first level compatibility index value different from the first compatibility index value of the first assay.

In some embodiments of the above system, each assay definition file can comprise a second level compatibility index value, and wherein the determining step further can comprise (c) evaluating which of a plurality of other available assays have an assay definition file comprising the same second level compatibility index value as the first assay, wherein the same second level compatibility index value is indicative of second-level compatibility.

In some embodiments of the above system, the evaluating step can comprise (c1) identifying any assays which have second level compatibility index values different from the second compatibility index value of the first assay; and (c2) providing a second list of second assays, wherein the second list excludes any assay having a second level compatibility index value different from the second compatibility index value of the first assay.

In some embodiments of the above system, the first level compatibility can comprise compatibility of performing two assays concurrently at a single workstation, the parameters selected from the group consisting of: incubation time, lysis time, reagent volume, reagent type, incubation temperature, lysis temperature, workstation time demands, regulatory classification, business considerations, and a combination thereof.

In some embodiments of the above system, the second level compatibility can comprise compatibility of performing two assays concurrently on the automated instrument, the parameters selected from the group consisting of: regulatory classification, workflow incompatibility, business considerations, and a combination thereof.

In some embodiments of the above system, the instrument prevents the concurrent performance of incompatible assays within the same workstation when the first compatibility indexes are different. In some embodiments, the two discrete assay workflows are performed in the same workstation. In some embodiments, the instrument is prevented from concurrently performing assays with different second compatibility index values. In some embodiments, two assays have the same first level compatibility index value and have different second level compatibility index values. In some embodiments, the difference in the second level compatibility index values can comprise a business reason. In some embodiments, the difference in the second level compatibility index values can comprise a regulatory classification.

In some embodiments of the above system, if the assays are compatible, the system can further comprise instructions for one or more of the following (d) initiating an assay-specific sample preparation script on the instrument; (e) comparing identifying indicia on a consumable package to a set of assay-specific identifying data stored on the instrument; (f) initiating an assay-specific load cartridge script on the instrument; (g) comparing levels of detectable signals in a loaded cartridge to a set of assay-specific detectable signal data stored on the instrument to determine whether the cartridge was successfully loaded; (h) initiating an assay-specific reaction script on the instrument; (i) initiating an assay-specific data analysis algorithm on the instrument; or (j) deriving a final call for the assay, based on one or more assay-specific result algorithms or scripts.

In some embodiments of the above system, the assay protocol can comprise a reaction selected from the group selected from: Polymerase Chain Reaction (PCR), Transcription Mediated Amplification (TMA), Oligonucleotide Ligation Assay (OLA), Ligase Chain Reaction (LCR), Rolling Circle Amplification (RCA), Strand Displacement Amplification (SDA), and a hybridization reaction.

In some embodiments of the above system, the system further can comprise a bar code reader. In some embodiments of the above system, the identifying indicia can comprise a bar code.

Also presented herein is a method of performing a plurality of compatible discrete assays concurrently on a single automated instrument, the method comprising, for each discrete assay: providing an automated instrument comprising a first workstation and a second workstation, each of the first and second workstations configured to receive and processes a plurality of samples according to a plurality of different automated assay workflows, wherein each different automated assay workflow has an associated unique assay definition file or user-defined protocol file comprising a first level compatibility index value and a second level compatibility index value; selecting a first assay from among a first list of available assays; evaluating which of a plurality of other available assays have an assay definition file or user-defined protocol file comprising the same first level compatibility index value as the first assay, wherein the same first level compatibility index value is indicative of compatibility for concurrent processing on the same workstation of the automated instrument; evaluating which of a plurality of other available assays have an assay definition file or user-defined protocol file comprising the same second level compatibility index value as the first assay, wherein the same second level compatibility index value is indicative of compatibility for concurrent processing on the automated instrument; and performing the discrete assay workflows concurrently on the instrument when the assays are compatible.

BRIEF DESCRIPTION OF THE DRAWINGS

FIG. 5 is a look up table to show rack and run compatibility according to one embodiment.

DETAILED DESCRIPTION

Figure 1:
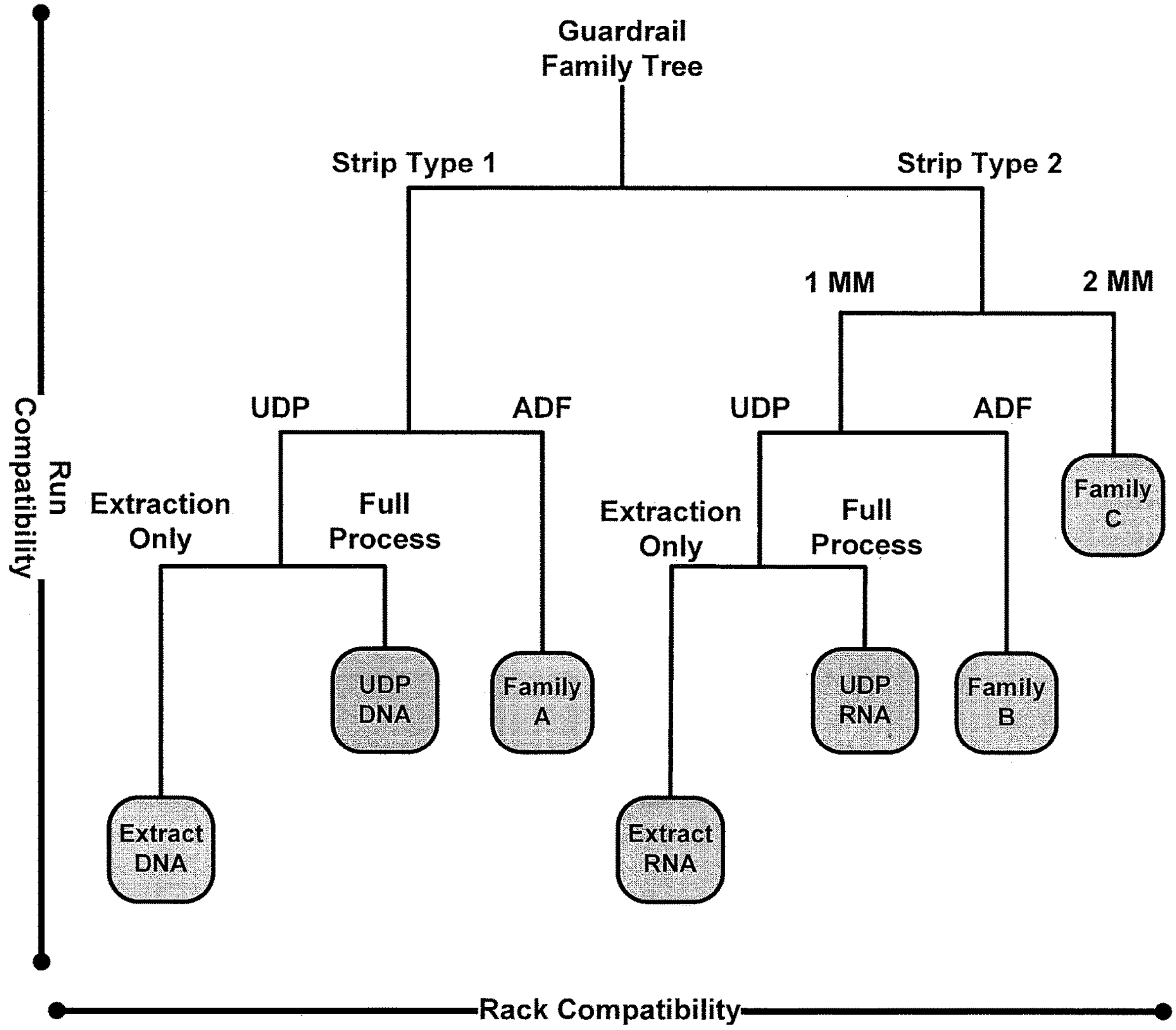
FIG. 1 is a schematic drawing demonstrating a method of assigning first- and second-level compatibility index values to a particular assay workflow or user defined protocol (UDP).

Automated diagnostic instruments are now able to carry out processing and testing of multiple samples in parallel. These devices can advantageously be used in high throughput to facilitate the sample preparation and testing. By way of example, automated diagnostic instruments can prepare samples for nucleic acid amplification assays, and perform the amplification and detection. Depending on the type of samples and the type of assay, however, many times, assay protocols are not compatible with each other on the same instrument, either because of physical constraints on the instrument, or for business reasons. For example, any two assay protocols may have different incubation times, lysis times, reagent volumes, reagent types, incubation temperatures, lysis temperatures, workstation time demands, or other parameters that render it impossible for the instrument to perform different assays in samples in a single workstation, or even on the same instrument. In addition to physical constraints, regulatory classifications and business considerations are each factors which may prevent the instrument from processing samples concurrently. In order to address this issue, users had to manually compare assay protocols on a chart or table to determine whether they can be performed concurrently on the same rack, or even on different racks of the same instrument. Such manual approaches can be error prone, as well as inefficient and labor intensive. Thus, there exists a great need for improved methods to identify compatible assay protocols and prevent incompatible assay protocols from being performed concurrently.

In accordance with the above, provided herein are methods and systems for performing an assay protocol on an automated instrument. In some embodiments of the present technology, such methods and systems can permit the concurrent performance of discrete assay workflows on an instrument when the assay workflows are compatible, and can prevent the concurrent performance of incompatible assay protocols within the same instrument. The methods provided herein allow for improved reliability and ease of use when performing an assay on an automated instrument.

Accordingly, provided herein is a method of providing an automated instrument comprising a first workstation and a second workstation and a common service that is shared by both workstations, each of the first and second workstations configured to receive and processes a plurality of samples according to a plurality of different automated assay workflows, wherein each different automated assay workflow has an associated unique assay definition or user-defined protocol file; determining whether two discrete assay workflows are compatible or incompatible with each other for concurrent processing on the automated instrument; and performing the discrete assay workflows concurrently on the instrument when the assay protocols are compatible.

As used herein, the terms "workstation," "rack" and like terms refer to an assembly that can hold a plurality of samples within an instrument designed to process those samples together. Thus, two workflows which can be performed concurrently on the same rack are designated herein as "rack-compatible."

Two workflows which can be performed concurrently on the same instrument are designated herein as "run-compatible." In certain embodiments, two run-compatible workflows are not compatible on the same rack, but can be performed on separate racks in the instrument. In certain embodiments, two run-compatible workflows are compatible on the same rack. In certain other embodiments, two run-incompatible workflows are compatible on the same rack, but cannot, for any one of a variety of reasons, be performed concurrently on the same instrument.

As used herein, the terms "workflow," "assay workflow," "assay," "assay protocol," "test," and like terms refer to a procedure for processing a sample. In typical embodiments, a workflow can include sample preparation steps, such as cell lysis, nucleic acid extraction, nucleic acid purification, nucleic acid digestion, nucleic acid modification, protein extraction, protein purification, and the like. Several methods of nucleic acid extraction useful in the embodiments disclosed herein are known in the art. Exemplary discussions of nucleic acid extraction can be found, for example, in U.S. patent application Ser. No. 12/172,214, filed Jul. 11, 2008, U.S. patent application Ser. No. 12/172,208, filed Jul. 11, 2008, and U.S. patent application Ser. No. 11/281,247, filed Nov. 16, 2005, all of which are incorporated herein by reference in their entirety. Likewise, exemplary discussions of protein extraction can be found, for example, in U.S. Pat. Nos. 8,053,239 and 6,864,100, both of which are incorporated herein by reference in their entirety.

In some typical embodiments, a workflow can also include nucleic acid amplification reactions. In some typical embodiments, a workflow can further include data analysis procedures.

Accordingly, in certain embodiments, workflows are not directly compatible with each other due to physical differences, such as incubation time, lysis time, reagent volume, reagent type, incubation temperature, lysis temperature, workstation time demands, and the like. Each of these parameters place unique physical restraints on the motion and capacity of either the workstation itself or on a shared service resource within an automated instrument. For example, an RNA extraction protocol, a DNA extraction protocol, and a protein extraction protocol may each require different motions for a pipetting head on an instrument, and therefore cannot be processed at the same time on the same workstation. By way of another example, a PCR assay and an assay based solely upon hybridization of detectable probes to a target may require different temperature cycling and timing requirements, and therefore cannot be processed at the same time. It will be appreciated that any physical, temporal or other limitation can present a reason for which two workflows are not directly compatible with each other.

Figure 4:
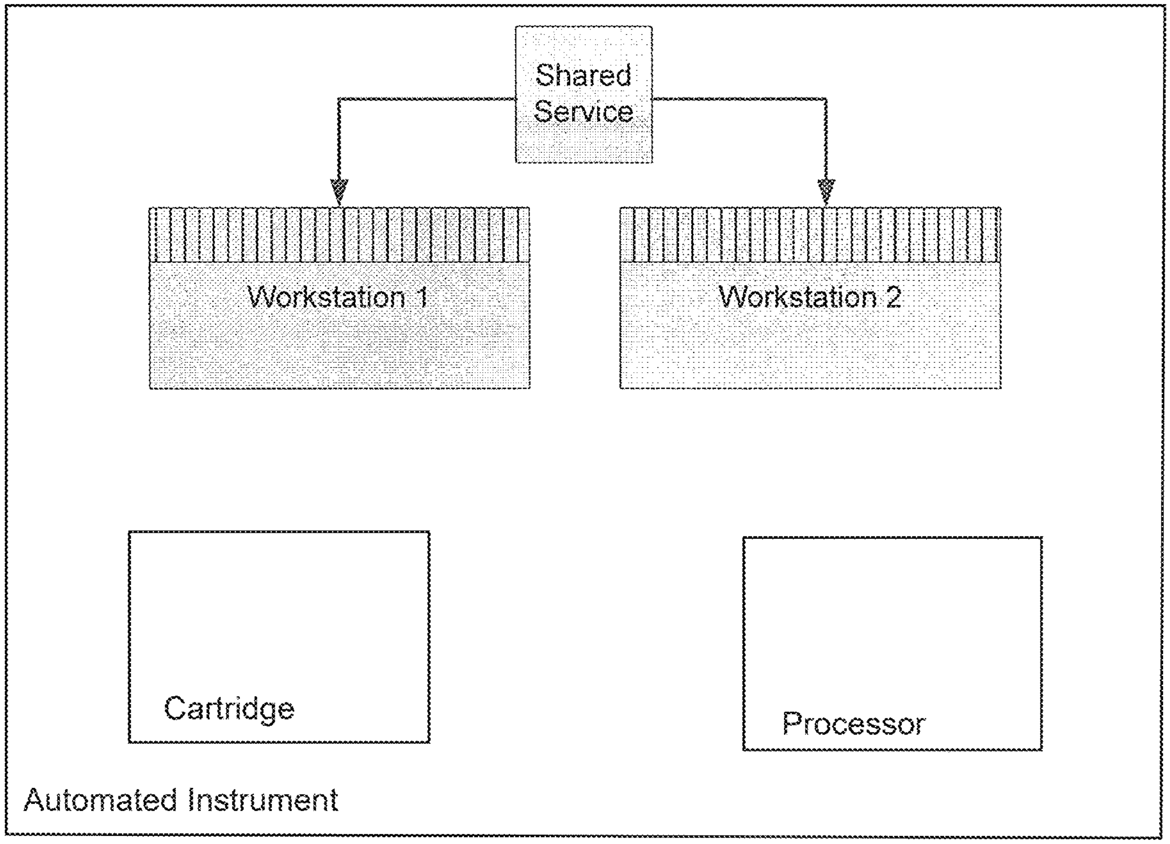
FIG. 4 is a schematic drawing that illustrates an automated instrument with independent workstations and a shared service according to one embodiment.

In certain embodiments, incompatibility is driven by physical restraints on motion and capacity of a shared service resource within an automated instrument that is shared by two or more workstations. As illustrated in FIG. 4, two or more independent workstations can utilize a shared resource. The shared resource can be, for example, a pipettor, a robotic arm, a single detector unit, or any other resource that is shared by two or more workstations.

The physical, temporal or other parameters need not be identical between assays in order to indicate compatibility. Rather, parameters can fall within a range which confers compatibility of, for example, a shared resource. Table 2 in Example 1 below provides an example for assays with parameters that vary within a range, yet still maintain compatibility, whereas assays with parameters outside any one range are no longer compatible.

In addition, workflows that are otherwise physically compatible on an instrument can nonetheless be incompatible for other reasons. In certain embodiments, two workflows cannot be performed concurrently in order to comply with regulatory restraints. For example, if one assay protocol has been approved by a regulatory agency such as the United Stated Food and Drug Administration (FDA), that agency may stipulate that the assay protocol cannot be performed concurrently with an unapproved assay protocol. Likewise, in certain embodiments, a manufacturer or user of instruments, consumable materials, or reagents may be under contractual restrictions or other business limitations, under which two workflows cannot be performed concurrently on the same instrument. It will be appreciated that incompatibility can be determined for any reason for which a manufacturer or user determines that two workflows should be incompatible. The methods and systems provided herein make it possible to identify compatible workflows and perform a plurality of compatible workflows on the same instrument at the same time.

Figure 3:
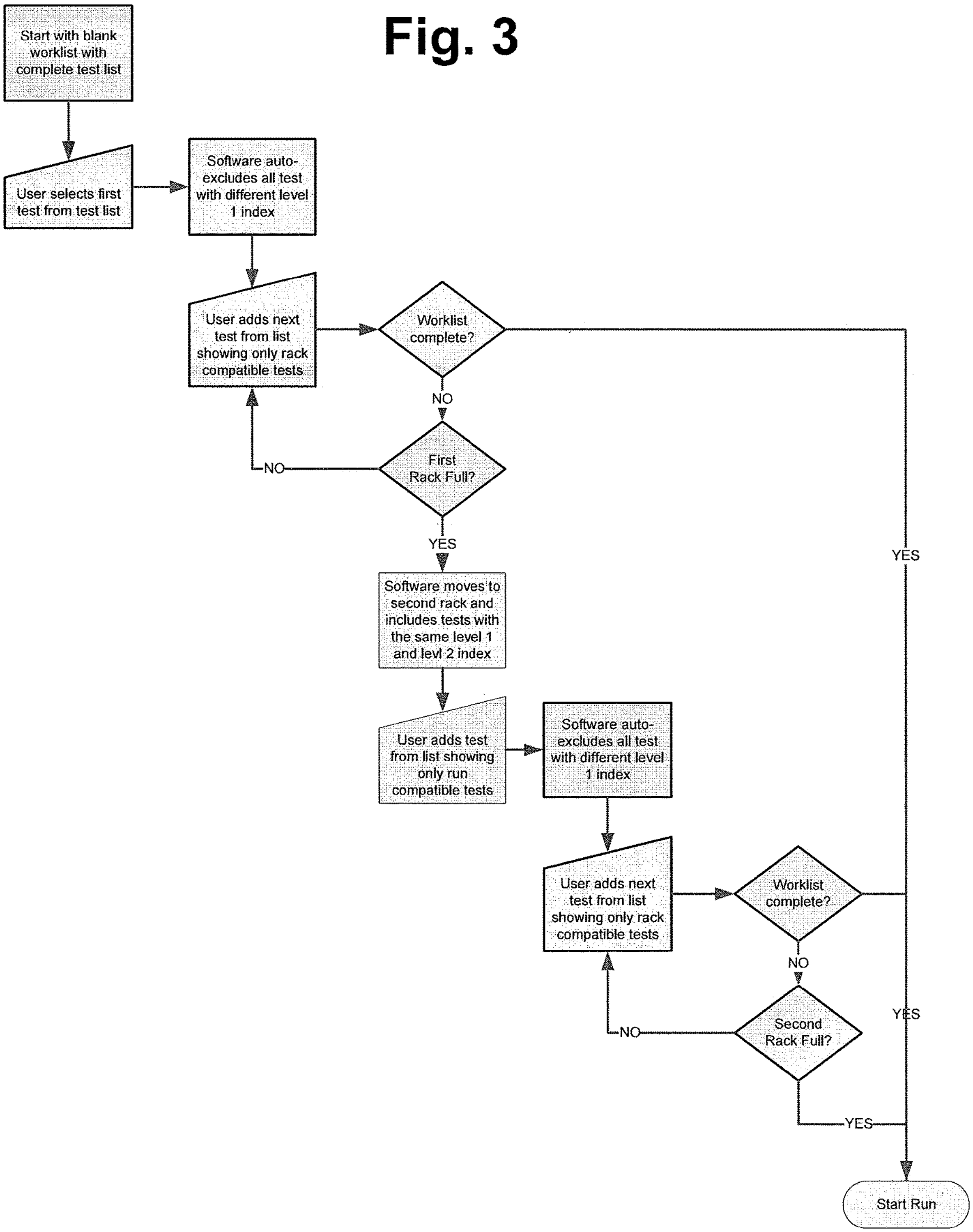
FIG. 3 is a schematic drawing demonstrating a method of selecting and performing concurrent assay protocols according to one embodiment.

As illustrated in FIG. 3, rack and run compatibility can be determined by any of a number of workflow parameters. For example, parameters which may determine rack or run compatibility include, but are not limited to, reagent strip design, number and type of consumable reagents and the specific processes performed during the workflow, such as nucleic acid extraction or full analysis of a nucleic acid sample after extraction.

Assay Definition Files

In embodiments of the methods and systems provided herein, each different automated assay workflow has an associated unique assay definition or user-defined protocol file. As used herein, the term assay definition file (ADF) refers to a file that provides at least some, and typically all of the assay specific parameters for that workflow. In addition, an ADF can provide compatibility index values for a particular workflow. In typical embodiments, the ADF can contain all of the information needed to run the assay on an automated instrument. One function of the ADF is to provide a layer of independence between the instrument and the assay. This independence provides the mechanism by which an instrument manufacturer or assay reagent manufacturer can release new assay protocols for an instrument without producing major revisions to the instrument software.

An ADF can comprise one or more of the components set forth in Table 1 below. In particular, the ADF can include the two-level index values for rack and run compatibility.

TABLE 1

| ADF parameters and settings |
| --- |
| Level-1 compatibility index value |
| Level-2 compatibility index value |
| Sample prep parameters |
| Scripts used for sample prep, load cartridge, and PCR. |
| Required consumable barcodes |
| Fill check thresholds |
| PCR Protocol |
| Script used to generate results |
| Thresholds used to generate results |
| Parameters used to drive the data analysis engine within the instrument |

Thus, in some embodiments of the methods and systems provided herein, if the assay protocols are compatible, the ADF can include instructions for performing one or more of the following: initiating an assay-specific sample preparation script on the instrument; comparing identifying indicia on a consumable package to a set of assay-specific identifying data stored on the instrument; initiating an assay-specific load cartridge script on the instrument; comparing levels of detectable signals in a loaded cartridge to a set of assay-specific detectable signal data stored on the instrument to determine whether the cartridge was successfully loaded; initiating an assay-specific reaction script on the instrument; initiating an assay-specific data analysis algorithm on the instrument; or deriving a final call for the assay, based on one or more assay-specific result algorithms or scripts. The detectable signals that are compared during a load cartridge script can be any suitable detectable signal that indicates proper loading. In typical embodiments, the detectable signal is fluorescence, and the ratio of fluorescence at various wavelengths in a sample or reagent can be compared to set of pre-determined fluorescence data in order to determine whether the cartridge was properly loaded.

In some embodiments, the ADF can also comprise a reaction including, but not limited to: Polymerase Chain Reaction (PCR), Transcription Mediated Amplification (TMA), Oligonucleotide Ligation Assay (OLA), Ligase Chain Reaction (LCR), Rolling Circle Amplification (RCA), Strand Displacement Amplification (SDA), and a hybridization reaction.

Example 5 below describes an exemplary use of an ADF file to run assay protocols on an instrument.

Typically, when a new assay is made available to a customer, the corresponding ADF is installed on the instrument. Once an ADF is installed on the instrument, that assay is then available for execution on the instrument. The instrument software can then use the index values to control addition of tests to a run worklist. If assay protocols share the same rack index value, then they are allowed to be in the worklist in contiguous positions in a single rack. If two assay protocols have a different run index, then they can not be in the same run worklist. When a user selects the first assay to be included in a run, the software checks the compatibility index values of all other assay protocols available on the instrument and modifies the list of assay protocols that the user can select according to the rules listed above, thereby ensuring that the customer does not choose incompatible assay protocols.

An ADF may be provided in any suitable format. For example, the ADF could be provided by a manufacturer on a storage medium such as CD-ROM or USB key, or downloaded from the manufacturer and then transferred to the terminal that controls the instrument. Multiple ADFs, each defining a distinct assay protocol, can thus be installed on the same instrument. Advantageously, the methods and systems provided herein make it possible for the system to identify assay protocols with the same compatibility index values, rather than force a user to consult a chart or table.

User Defined Protocols

In certain embodiments, assay parameters are determined by the user, rather than the manufacturer. These user defined protocols (UDP) can also be assigned first-level and second-level compatibility index values to ensure compatibility with other commercially-developed assay protocols. One of the benefits of the indexes and assay definition files is that it provides a firewall between user defined assay protocols and commercially-developed assay protocols that also covers compatibility. The index values can be used to set up unique controls for user defined protocols which are different from the index values for commercially-developed assay protocols. In the embodiment illustrated in FIG. 1, User Defined Protocols are represented by the boxes labeled as UDP and Extraction Only.

Thus, as illustrated in FIG. 1, first-level and second-level compatibility index values for a UDP can be assigned according to similar factors that determine compatibility for ADFs. Such factors include, for example, the extraction kit and PCR type selected by the user, reagent strip design, the number of MM (master mixes), and the specific process (extraction versus full process). The UDP can thus include compatibility index values as part of the full code, since there is no ADF provided by a manufacturer. An illustration of this process is set forth in Example 6 below.

It will be appreciated that new extraction kits, PCR assay types, and other reagents can be provided by a manufacturer with a file similar to an ADF. Thus, when such files are installed on an instrument, and a new UDP is created, the index values for one or more UDPs may be updated accordingly.

First Level Compatibility Index Value

In some embodiments, the assay definition or user defined protocol file can comprise a first level compatibility index value. Typically, the first level compatibility index value refers to rack compatibility. However, in certain other embodiments, the first level compatibility index value refers to run compatibility and the second level index value refers to rack compatibility. Thus, the method can comprise (a) selecting a first assay protocol from among a first list of available assay protocols; and (b) evaluating which of a plurality of other available assay protocols have an assay definition file comprising the same first level compatibility index value as the first assay. In typical embodiments, two assay protocols having the same first level compatibility index value is indicative of first-level compatibility. It will be appreciated, however, that any suitable mechanism that can assign and identify compatibility values to individual assays can serve in the methods and systems provided herein. Thus, in some embodiments, two assay protocols that are rack compatible may have different first level index values. However, for convenience in this disclosure, two assay protocols with first level compatibility are considered as having the same first level compatibility index value.

The list of available assay protocols can change as the user selects one or more assay protocols to perform, and first level compatibility is evaluated. As such, the evaluating step (b) can comprise the steps of (b1) identifying any assay protocols which have first level compatibility index values different from the first compatibility index value of the first assay; and (b2) providing a second list of second assay protocols, wherein the second list excludes any assay having a first level compatibility index value different from the first compatibility index value of the first assay.

In some embodiments, the first level compatibility can take into consideration any parameter that could prevent performance of two assay protocols concurrently at a single workstation. Such parameters are known to those of skill in the art, and can include, for example, physical parameters such as incubation time, lysis time, reagent volume, reagent type, incubation temperature, lysis temperature, workstation time demands, and the like. Further, other parameters can include considerations such as regulatory classification, business considerations, and the like.

Second Level Compatibility Index Value

In some embodiments, the assay definition or user defined protocol file can comprise a second level compatibility index value. Typically, the second level compatibility index value refers to run compatibility. However, in certain other embodiments, the second level compatibility index value refers to rack compatibility and the second level index value refers to run compatibility. Thus, the method can comprise (c) evaluating which of a plurality of other available assay protocols have an assay definition file comprising the same second level compatibility index value as the first assay, wherein the same second level compatibility index value is indicative of second-level compatibility. In typical embodiments, two assay protocols having the same second level compatibility index value is indicative of second level compatibility. It will be appreciated, however, that any suitable mechanism that can assign and identify compatibility values to individual assays can serve in the methods and systems provided herein. Thus, in some embodiments, two assay protocols that are run compatible may have different second level index values. However, for convenience in this disclosure, two assay protocols with second level compatibility are considered as having the same second level compatibility index value.

The list of available assay protocols can change as the user selects one or more assay protocols to perform, and second level compatibility is evaluated. As such, the evaluating step (c) can comprise the steps of (c1) identifying any assay protocols which have second level compatibility index values different from the second compatibility index value of the first assay; and (c2) providing a second list of second assay protocols, wherein the second list excludes any assay having a second level compatibility index value different from the second compatibility index value of the first assay.

In some embodiments, the second level compatibility can take into consideration any parameter that could prevent performance of two assay protocols concurrently at a single workstation. Such parameters are known to those of skill in the art, and can include, for example, physical parameters such as incubation time, lysis time, reagent volume, reagent type, incubation temperature, lysis temperature, workstation time demands, and the like. Further, other parameters can include considerations such as regulatory classification, business considerations, and the like.

In some embodiments, the instrument prevents the concurrent performance of incompatible assay protocols within the same workstation when the first compatibility indexes are different. In some embodiments, the two discrete assay workflows are performed in the same workstation. In some embodiments, the instrument is prevented from concurrently performing assay protocols with different second compatibility index values. In some embodiments, two assay protocols have the same first level compatibility index value and have different second level compatibility index values. In some embodiments, the difference in the second level compatibility index values can comprise a business reason. In some embodiments, the difference in the second level compatibility index values can comprise a regulatory classification.

It will be appreciated that the two-level index described above is expandable from a two workflow system to larger numbers of workflows that are desired to run concurrently on an instrument, but may have constraints to run concurrently based on physical or business constraints. Thus, as illustrated in FIG. 3, additional workflows may be added to a rack or multiple racks as needed, and the methods described herein will ensure that compatibility among all assays is maintained.

Instruments and Systems

Also presented herein is a system for performing an automated assay, the system comprising an automated instrument comprising a first workstation and a second workstation, each of the first and second workstations configured to receive and processes a plurality of samples according to a plurality of different automated assay workflows, and supported by a single service resource. Each different automated assay workflow typically comprises an associated unique assay definition file or user-defined protocol file. The system also comprises a processor; a storage capacity; and a program for performing an automated assay, the program comprising instructions for determining whether two discrete assay workflows are compatible or incompatible with each other for concurrent processing on the automated instrument; and performing the discrete assay workflows concurrently on the instrument when the assays are compatible.

Automated instruments which can perform multiple assay protocols concurrently are known to those of skill in the art. Exemplary discussions of typical automated instruments for use with the methods provided herein can be found, for example, in U.S. patent application Ser. No. 12/173,023, filed Jul. 14, 2008, which is incorporated herein by reference in its entirety.

It will be appreciated that the methods and systems described herein can apply to instruments that comprise 2, 3, 4 or more workstations wherein at least 2 of the workstations are supported by a common service resource. For example, an instrument with 4 workstations and a single pipette head could still be compatibility controlled by the 2 index concept described herein.

As used herein, the terms storage capacity, storage device, storage and the like can refer to any medium, device or means of storage of information. Storage can include, but is not limited to, a disk drive device such as a hard drive, floppy disk, optical or magneto-optical disk, memory such as RAM or ROM chips, and any other medium used to record or store data. In some embodiments, a storage capacity is connected to a processor which sends information to be recorded on the storage capacity after it is acquired. In specific embodiments, data is acquired by a system and is recorded on a storage capacity. In other embodiments, data is acquired by a system and information is first processed and the processed information is recorded on a storage capacity.

The files and programs provided herein can be in any suitable programming language. In certain embodiments, the ADF utilizes XML as a mechanism for formatting files. Further, in certain embodiments, ADF utilizes Python as a scripting language to provide a mechanism for executing result logic using common technologies available on the instrument. It will be appreciated that any suitable file format and programming language can be utilized in the methods and systems provided herein. In certain embodiments, files can be encrypted to protect against the use of counterfeit reagents and to control specific parameter details on assay runs.

As used herein, an "input" can be, for example, data received from a keyboard, rollerball, mouse, voice recognition system or other device capable of transmitting information from a user to a computer. The input device can also be a touch screen associated with the display, in which case the user responds to prompts on the display by touching the screen. The user may enter textual information through the input device such as the keyboard or the touch-screen.

The invention is operational with numerous other general purpose or special purpose computing system environments or configurations. Examples of well-known computing systems, environments, and/or configurations that may be suitable for use with the invention include, but are not limited to, microcontrollers, personal computers, server computers, hand-held or laptop devices, multiprocessor systems, microprocessor-based systems, programmable consumer electronics, network PCs, minicomputers, mainframe computers, distributed computing environments that include any of the above systems or devices.

As used herein, "instructions" refer to computer-implemented steps for processing information in the system. Instructions can be implemented in software, firmware or hardware and include any type of programmed step undertaken by components of the system.

A "microprocessor" or "processor" may be any conventional general purpose single- or multi-core microprocessor such as a Pentium® processor, Intel® Core™, a 8051 processor, a MIPS® processor, or an ALPHA® processor. In addition, the microprocessor may be any conventional special purpose microprocessor such as a digital signal processor or a graphics processor. A "processor" may also refer to, but is not limited to, microcontrollers, field programmable gate arrays (FPGAs), application-specific integrated circuits (ASICs), complex programmable logic devices (CPLDs), programmable logic arrays (PLAs), microprocessors, or other similar processing devices.

The system is comprised of various modules as discussed in detail herein. As can be appreciated by one of ordinary skill in the art, each of the modules comprises various sub-routines, procedures, definitional statements and macros. Each of the modules are typically separately compiled and linked into a single executable program. Therefore, the following description of each of the modules is used for convenience to describe the functionality of the preferred system. Thus, the processes that are undergone by each of the modules may be arbitrarily redistributed to one of the other modules, combined together in a single module, or made available in, for example, a shareable dynamic link library.

Certain embodiments of the system may be used in connection with various operating systems such as SNOW LEOPARD®, iOS®, LINUX, UNIX or MICROSOFT WINDOWS®.

Certain embodiments of the system may be written in any conventional programming language such as assembly, C, C++, C#, BASIC, Pascal, or Java, and run under a conventional operating system.

In addition, the modules or instructions may be stored onto one or more programmable storage devices, such as FLASH drives, CD-ROMs, hard disks, and DVDs. One embodiment includes a programmable storage device having instructions stored thereon.

In some embodiments of the above system, the system further can comprise a device for reading identifying indicia on reagent packaging. It will be appreciated that any suitable device for reading identifying indicia can be used in the systems provided herein. Likewise, any suitable identifying indicia may be used that is compatible with the device on the instrument. Examples include bar codes, QR codes, RFID tags, color codes and the like. In typical embodiments, the device can be a bar code reader, and the identifying indicia can comprise a bar code. Example 4 below describes use of barcode labels to properly identify consumable reagents.

ADVANTAGES AND IMPROVEMENTS

The methods and systems presented herein provide numerous advantages over existing approaches. For example, the use of an ADF by a manufacturer for the distribution of an assay protocols provides a mechanism for release of new or modified assay protocols on the instrument platform without requiring a coordinated instrument software update. By eliminating the need for instrument software revisions, this approach provides a more direct path towards release for the assay. Additionally, as needed, the manufacturer can modify compatibility between assay protocols to meet business or other needs without having to revise the instrument software.

Compatibility has traditionally been controlled using a table or other means that is maintained within the system and requires an update to expand menu. Using a two-level index does not require updating a table or any other means in the software to expand menu. Further, users do not need to have any specific knowledge about assay compatibility since the instrument software controls which assay protocols are available to mix in a single run.

An additional advantage of using an ADF is that barcode information in the ADF can be used to confirm that reagents are appropriately loaded onto the instrument, thereby preventing user error and the resulting loss of time and resources.

Having generally described this invention, a further understanding can be obtained by reference to certain specific examples which are provided herein for purposes of illustration only, and are not intended to be limiting.

Example 1

Assigning First-Level and Second-Level Compatibility Index Values for User Defined Protocols and Commercially-Supplied Assay Protocols This example demonstrates the process of assigning first- and second-level compatibility index values to a particular assay workflow or user defined protocol (UDP).

An automated sample processor and analysis instrument has the ability to run two discrete sample processing workflows, or racks, concurrently (run compatible). However, there are certain actions within a sample processing workflow that modified and still maintain compatibility (rack-compatible) as well as certain actions that render workflows incompatible on the instrument in the same run (incompatible). In addition to physical limitations, there may be business requirements to keep assay protocols from running together on an instrument.

To manage this range of performance demands, a two-level index was generated that identifies rack-compatible and run-compatible assay protocols. The index is assigned and maintained by the instrument manufacturer. The first level index implicates rack-compatibility, that is, assay protocols with the same index value can run in the same rack. The second level index implicates run-compatibility, that is, assay protocols which can be practiced in the second rack on an instrument relative to the assay in the first rack; by definition, rack-compatible assay protocols are also run-compatible. If assay protocols do not share a rack or run compatible index level, then the instrument is prevented from performing assay protocols on the instrument concurrently.

FIG. 1 illustrates an exemplary embodiment of this process. In the process shown in FIG. 1, run compatibility (second level compatibility) is indicated by protocols on the same vertical level. Rack compatibility (first level compatibility) is indicated by protocols on the same horizontal level. Thus, for example, two samples must be in the same box in the diagram to be in the same rack in a worklist. Boxes on the same horizontal level share the same Level 2 compatibility index, that is, assay protocols from different boxes can be on separate racks inside the same run, but not in the same rack.

As shown in FIG. 1, factors that determine compatibility are reagent strip design, the number of MM (master mixes), the use of a UDP or ADF (user defined protocol versus assay definition file), and the specific process (extraction versus full process).

Table 2 below illustrates several parameters that can influence compatibility. For example, in Table 2, cells with text in double-brackets highlight the parameters in Assays 4 and 5 that break compatibility with Guardrail Family A. Specifically, for Assay 4, aspiration height, lysis temperature, number of washes and magnet speed are outside of the limits for each parameter defined for Assays 1-3. Similarly, for Assay 5, aspiration height and lysis time are outside the limits for those parameters.

TABLE 2

| Guardrail Family A | | | | | | |
|---|---|---|---|---|---|---|
| | Compatible Assays | | | | Incompatible Assays | |
| Assay Step | Limits | Assay 1 | Assay 2 | Assay 3 | Assay 4 | Assay 5 |
| Aspiration Height | 1200-1600 | 1600 | 1550 | 1200 | [[1150]] | [[1700]] |
| Lysis Time | 0 to 30 min | 10 min | 5 min | 0 min | 10 min | [[35 min]] |
| Lysis Temperature | 30 to 50° C. | 42° C. | 30° C. | 50° C. | [[27° C.]] | 42° C. |
| Number of washes | 1 | 1 | 1 | 1 | [[2]] | 1 |
| Magnet Speed | Slow | Slow | Slow | Slow | [[Fast]] | Slow |

Table 2 thus illustrates that physical, temporal or other parameters need not be identical between assays in order to indicate compatibility. Rather, parameters can fall within a range which confers compatibility of, for example, a shared resource.

Table 3 below is an example of a table that assigns rack and run compatibility values for a set of assay protocols.

TABLE 3

| Assay Protocol | Workflow Type | Level 1 Index | Level 2 Index |
|---|---|---|---|
| 1 | Extract DNA | 1 | 1 |
| 2 | UDP DNA | 2 | 2 |
| 3 | Family A | 3 | 2 |
| 4 | Family A | 3 | 2 |
| 5 | Family A | 4 | 3 |
| 6 | Extract RNA | 5 | 1 |
| 7 | Extract RNA | 5 | 1 |
| 8 | UDP RNA | 6 | 2 |
| 9 | Family B | 7 | 2 |
| 10 | Family C | 8 | 4 |

In Table 3, Families A, B, and C represent workflows that are not directly compatible with each other due to physical differences, such as incubation time, lysis time, reagent volume, reagent type, incubation temperature, lysis temperature or workstation time demands. In the diagram and the table, families A and B are run compatible, meaning that a first workstation could practice tests in Family A (not B), and that a second workstation could practice test in Family B (not A, if a B is selected for that workstation first). As shown in FIG. 1, Family C is neither rack-nor run-compatible with the other workflows.

In Table 3, three different Family A tests have a different compatibility index. While the workflows would indicate that they should be physically compatible, there could be other reasons that the manufacture chooses not to practice them on in the instrument at the same time. For example, when the manufacturer partners with a third party company, it may be desirable to prevent the user to run both manufacturer-supplied and third party-supplied tests on the instrument at the same time, even if the workflow of the test would allow it.

Example 2

Identification of Assay Compatibility

Figure 2:
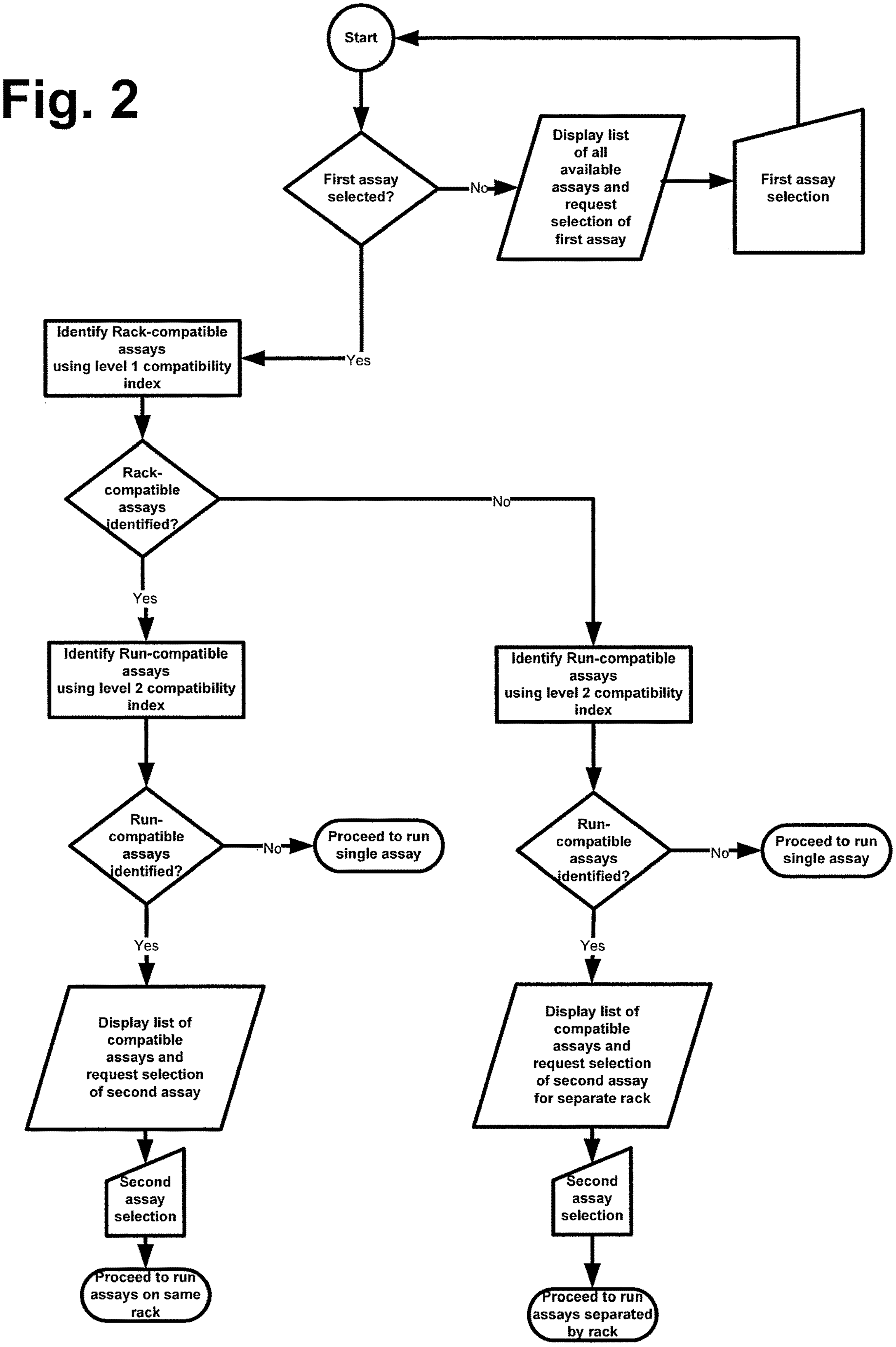
FIG. 2 is a schematic drawing demonstrating a method of identifying first-level and second level compatibility between two assay protocols according to one embodiment.

This example demonstrates identification of first-level and second-level compatibility between two assay protocols according to one embodiment. In the exemplary methods shown in FIG. 2, the compatibility between a first and second assay is determined by comparing two levels of compatibility index values. In order to avoid running incompatible assays concurrently, users had to manually compare assay protocols on a chart or table to determine whether they can be performed concurrently on the same rack, or even on different racks of the same instrument. An example of such a look up table is shown in FIG. 5. Such manual approaches can be error prone, as well as inefficient and labor intensive. This example provides an example of an automated method to identify compatible assay protocols and prevent incompatible assay protocols from being performed concurrently.

Assay protocols on the same rack. As described in the schematic shown in FIG. 2, a first assay is selected by the user from a list of all available assay protocols. Based on user input, the first-level (rack) compatibility index value for the selected first assay is obtained from the assay definition file (ADF) for the first assay, or from the UDP if the selected assay is user-defined. That compatibility index value is then compared to the first-level compatibility index value (obtained from the ADF or UDP for each respective assay) of each of the other available assay protocols. All assay protocols are identified which share a first-level compatibility index value with the selected assay, and any non-compatible assay protocols are excluded from further consideration.

Next, the system obtains the second-level (run) compatibility index value for the selected first assay and compares the value to the second-level compatibility index value of all other remaining assay protocols. All assay protocols are identified which share a second-level compatibility index value with the selected assay, and any non-compatible assay protocols are excluded from further consideration. A list is then displayed which contains only first- and second-level compatible assay protocols. The user selects a second assay from that list, and when selection is complete, the system begins to perform the two assay protocols concurrently on the same rack, or on separate racks if desired.

Assay protocols on separate racks. Alternatively, the system can identify and run assay protocols on separate racks when they are not compatible to run together on the same rack. As described in the schematic shown in FIG. 2, a first assay is selected by the user from a list of all available assay protocols. Based on user input, the first-level (rack) compatibility index value for the selected first assay is obtained from the assay definition file (ADF) for the first assay, or from the UDP if the selected assay is user-defined. That compatibility index value is then compared to the first-level compatibility index value (obtained from the ADF or UDP for each respective assay) of each of the other available assay protocols. If no assay protocols are identified which share a first-level compatibility index value with the selected assay, the system then obtains the second-level (run) compatibility index value for the selected first assay and compares the value to the second-level compatibility index value of all other available assay protocols. All assay protocols are identified which share a second-level compatibility index value with the selected assay, and any non-compatible assay protocols are excluded from further consideration. A list is then displayed which contains only assay protocols which are compatible to run concurrently on separate racks. The user selects a second assay from that list, and when selection is complete, the system begins to perform the two assay protocols concurrently on separate racks.

No other compatible assay protocols. In the event that the system does not identify other assay protocols which are either rack-compatible or run-compatible, the user can choose to perform a single assay protocol, using one or multiple samples, on the same or separate racks.

Example 3

Addition of Tests to a Run Worklist

This example demonstrates the process of preparing a run worklist, including identification of assay protocols which can run concurrently in the same worklist, either on the same or on separate racks.

A user has a predetermined number of samples, each of which must be assigned an assay protocol. As shown in FIG. 3, a blank worklist is provided, setting forth a complete list of available assay protocols. The user selects a first test from the test list. Upon entry of the user selection, the system auto-excludes all protocols with a different first-level compatibility index value, and displays a list of only those assay protocols that are not excluded. From the list of remaining protocols, the user selects another protocol from the list. This process repeats until all samples have been assigned an assay protocol, or until the first rack is full.

If the first rack is full, the system allows the user to begin selecting assay protocols for the second rack. The system displays all protocols with the same level 2 (run compatible) index values as those in the first rack. The user then selects a protocol from that list of run compatible protocols. Once a first selection has been made for the second rack, the system auto-excludes all protocols with a different first-level compatibility index value, and displays a list of only those assay protocols that are not excluded. From the list of remaining protocols, the user selects another protocol from the list. This process repeats until all samples have been assigned an assay protocol, or until the second rack is full.

Example 4

Use of Barcodes

This example demonstrates the use of barcodes as identifying indicia for consumable packaging.

Consumable reagents provided by a supplier include a barcode label that the instrument can read. When an assay is created, the expected barcodes are identified in the ADF. When an instrument run commences, the instrument executes a catalog process, which confirms that the user loaded the proper consumables on the instrument deck. The barcode data stored in the ADF is used to provide this verification. If the barcode is not read, the instrument alerts the user and waits for assistance in acquiring the barcode. If the barcode is read, but does not match that expected for the assay test that was requested by the user, then the instrument alerts the user and waits for assistance in correcting the difference by, for example, swapping reagents. The use of barcodes on the reagents and barcode information in the ADF provides process assurance that the user has run the assay appropriately.

Example 5

Use of ADF to Run Assay Protocol on Instrument

This example demonstrates the use of an ADF to accurately run assay protocols on an instrument.

The instrument first checks the ADF to determine the sample prep script needed to complete the run. The script data is then combined with the sample prep parameters defined in the ADF and the sample preparation process is initiated.

Upon completion of sample prep, the instrument again checks the ADF and executes the load cartridge script identified in the ADF.

When load cartridge completes, the instrument looks in the ADF to find out the fluorescence ratios needed to determine if the cartridge successfully loaded and compares those ratios with readings taken. If the instrument determines that the cartridge was successfully loaded, it then looks in the ADF to determine the PCR scripts to be used and PCR protocol necessary. Once these values are retrieved, the instrument begins the PCR process.

Upon completion of PCR, the instrument retrieves the parameters needed to run the data analysis algorithms from the ADF and executes the data analysis.

When data analysis completes the instrument combines the values returned from the data analysis engine with the result logic and result script identified in the ADF to derive a final call for that particular test.

Example 6

Generation of UDP and Assignment of First-Level and Second-Level Compatibility Index Values This example demonstrates the creation of a UDP and assignment of compatibility index values to the UDP to accurately run assay protocols on an instrument.

A user generates a new UDP by responding to prompts on a touch-screen display, selecting the assay type, assay parameters and reagents for the protocol. Factors that are selected include, for example, type of extraction kit and PCR parameters. Specifically, selecting from several available options, the user selects a particular reagent strip design, a particular of MM, and the specific process (extraction versus full process). The user elects to program a full process, and as such, the user can further define cycle times, temperatures and other parameters for PCR.

Following a process set forth in FIG. 1, the system assigns first-level and second-level compatibility index values for the UDP according to similar factors that determine compatibility for ADFs. Based upon parameters including aspiration height, lysis temperature, lysis time, number of washes and magnet speed, the new UDP is assigned a first-level index value of '2' and a second-level index value of '2.'

Thus, going forward, when the user adds protocols to a run worklist, the user will be able to perform the new UDP concurrently with other ADFs or UDPs that have first and second level index values of 2 and 2, respectively.

It is to be understood that this invention is not limited to particular embodiments described, as such may, of course, vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which the embodiments belong. Although any methods and materials similar or equivalent to those described herein may also be used in the practice or testing of the embodiments, the preferred methods and materials are now described.

The term "comprising" as used herein is synonymous with "including," "containing," or "characterized by," and is inclusive or open-ended and does not exclude additional, unrecited elements or method steps.

It must be noted that as used herein and in the appended claims, the singular forms "a," "and," and "the" include plural referents unless the context clearly dictates otherwise. Thus, for example, reference to "a method" includes a plurality of such methods and equivalents thereof known to those skilled in the art, and so forth.

All references cited herein including, but not limited to, published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium may be coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

What is claimed is:

1. A method of performing an automated assay on a plurality of samples, the method comprising:

providing an automated instrument comprising a first workstation and a second workstation at a location physically separated from the first workstation, each of the first and second workstations configured to receive and process a plurality of samples according to a plurality of different automated assay workflows utilizing at least one shared resource, wherein each different automated assay workflow has an associated unique assay definition file or user-defined protocol file, wherein each assay definition file or user-defined protocol file comprises a first level compatibility index value, a second level compatibility index value, and provides one or more parameters for performing the automated assay workflow;

determining whether two discrete assay workflows are compatible or incompatible with each other for concurrent processing on the automated instrument, wherein the determining step comprises:

selecting a first assay workflow from among a first list of available assay workflows, and evaluating which of a plurality of other available assay workflows have an assay definition file or user-defined protocol file comprising the same second level compatibility index value as the first assay workflow, wherein assay workflows having an assay definition file or user-defined protocol file comprising the same second level compatibility index value are second-level compatible; and performing the two discrete assay workflows, each according to its own one or more parameters, concurrently at different workstations of the automated instrument when the two discrete assay workflows are second-level compatible and are first-level incompatible.

2. The method of claim 1, wherein assay workflows with the same second level compatibility index value can be processed concurrently only on different workstations of the automated instrument.

3. The method of claim 1, wherein the two discrete assay workflows are second-level compatible when no parameter associated with the two discrete assay workflows falls outside a range that confers second-level compatibility of the at least one shared resource.

4. The method of claim 1, wherein evaluating which of a plurality of other available assay workflows have an assay definition file or user-defined protocol file comprising the same second level compatibility index value as the first assay workflow comprises:

identifying any assay workflows which have second level compatibility index values different from the second level compatibility index value of the first assay workflow; and providing a second list of second assay workflows, wherein the second list excludes any assay workflow having a second level compatibility index value different from the second level compatibility index value of the first assay workflow.

5. The method of claim 1, wherein the second level compatibility value is determined based on parameters selected from the group consisting of: regulatory classification, workflow incompatibility, business considerations, and a combination thereof.

6. The method of claim 1, wherein the determining step further comprises, prior to evaluating which of a plurality of other available assay workflows have an assay definition file or user-defined protocol file comprising the same second level compatibility index value as the first assay workflow:

evaluating which of a plurality of other available assay workflows have an assay definition file or user-defined protocol file comprising the same first level compatibility index value as the first assay workflow; and determining that none of the plurality of other available assay workflows has an assay definition file or user-defined protocol file comprising the same first level compatibility index value as the first assay workflow.

7. The method of claim 1, wherein assay workflows with the same first level compatibility index value can be processed concurrently in the same or different workstations of the automated instrument.

8. The method of claim 7, wherein the first level compatibility index value is determined based on parameters selected from the group consisting of: incubation time, lysis time, reagent volume, reagent type, incubation temperature, lysis temperature, workstation time demands, regulatory classification, business considerations, and a combination thereof.

9. The method of claim 1, wherein the automated instrument prevents the concurrent performance of incompatible assay workflows within the same workstation when the first level compatibility index values are different.

10. The method of claim 1, wherein, if the two discrete assay workflows are compatible, the method further comprises one or more of the following:

initiating an assay-specific sample preparation script on the automated instrument;

comparing identifying indicia on a consumable package to a set of assay-specific identifying data stored on the automated instrument;

initiating an assay-specific load cartridge script on the automated instrument;

comparing fluorescence ratios in a loaded cartridge to a set of assay-specific fluorescence ratio data stored on the automated instrument to determine whether the cartridge was successfully loaded;

initiating an assay-specific reaction script on the automated instrument;

initiating an assay-specific data analysis algorithm on the automated instrument;

deriving a final call for an assay workflow, based on one or more assay-specific result algorithms or scripts.

11. The method of claim 1, wherein at least one of the assay workflows comprises a reaction selected from the group consisting of: Polymerase Chain Reaction (PCR), Transcription Mediated Amplification (TMA), Oligonucleotide Ligation Assay (OLA), Ligase Chain Reaction (LCR), Rolling Circle Amplification (RCA), Strand Displacement Amplification (SDA), and a hybridization reaction.

12. A system for performing an automated assay comprising:

an automated instrument comprising a first workstation and a second workstation at a location physically separated from the first workstation, each of the first and second workstations configured to receive and process a plurality of samples according to a plurality of different automated assay workflows utilizing at least one shared resource, wherein each different automated assay workflow has an associated unique assay definition file or user-defined protocol file, wherein each assay definition file or user-defined protocol file comprises a first level compatibility index value, a second level compatibility index value, and provides one or more parameters for performing the automated assay workflow;

a processor;

a storage capacity storing instructions executable by the processor to cause the automated instrument to:

determine whether two discrete assay workflows are compatible or incompatible with each other for concurrent processing on the automated instrument, wherein determining comprises:

selecting a first assay workflow from among a first list of available assay workflows, and evaluating which of a plurality of other available assay workflows have an assay definition file or user-defined protocol file comprising the same second level compatibility index value as the first assay workflow, wherein assay workflows having an assay definition file or user-defined protocol file comprising the same second level compatibility index value are second-level compatible; and perform the two discrete assay workflows, each according to its own one or more parameters, concurrently at different workstations of the automated instrument when the two discrete assay workflows are second-level compatible and are first-level incompatible.

13. The system of claim 12, wherein the two discrete assay workflows with the same second level compatibility index value can be processed concurrently only on different workstations of the automated instrument.

14. The system of claim 13, wherein the two discrete assay workflows are second-level compatible when no parameter associated with the two discrete assay workflows falls outside a range that confers second-level compatibility of the at least one shared resource.

15. The system of claim 12, wherein evaluating which of a plurality of other available assay workflows have an assay definition file or user-defined protocol file comprising the same second level compatibility index value as the first assay workflow comprises:

identifying any assay workflows which have second level compatibility index values different from the second level compatibility index value of the first assay workflow; and providing a second list of second assay workflows, wherein the second list excludes any assay workflow having a second level compatibility index value different from the second level compatibility index value of the first assay workflow.

16. The system of claim 12, wherein the second level compatibility value is determined based on parameters selected from the group consisting of: regulatory classification, workflow incompatibility, business considerations, and a combination thereof.

17. The system of claim 12, wherein determining further comprises, prior to evaluating which of a plurality of other available assay workflows have an assay definition file or user-defined protocol file comprising the same second level compatibility index value as the first assay workflow:

evaluating which of a plurality of other available assay workflows have an assay definition file or user-defined protocol file comprising the same first level compatibility index value as the first assay workflow; and determining that none of the plurality of other available assay workflows has an assay definition file or user-defined protocol file comprising the same first level compatibility index value as the first assay workflow.

18. The system of claim 12, wherein assay workflows with the same first level compatibility index value can be processed concurrently in the same or different workstations of the automated instrument.

19. The system of claim 12, wherein the first level compatibility index value is determined based on parameters selected from the group consisting of: incubation time, lysis time, reagent volume, reagent type, incubation temperature, lysis temperature, workstation time demands, regulatory classification, business considerations, and a combination thereof.

20. The system of claim 12, wherein the automated instrument prevents the concurrent performance of incompatible assay workflows within the same workstation when the first level compatibility index values are different.

21. The system of claim 12, wherein, if the two discrete assay workflows are compatible, the instructions executable by the processor include instructions to cause the automated instrument to:

initiate an assay-specific sample preparation script on the automated instrument;

compare identifying indicia on a consumable package to a set of assay-specific identifying data stored on the automated instrument;

initiate an assay-specific load cartridge script on the automated instrument;

compare fluorescence ratios in a loaded cartridge to a set of assay-specific fluorescence ratio data stored on the automated instrument to determine whether the cartridge was successfully loaded;

initiate an assay-specific reaction script on the automated instrument;

initiate an assay-specific data analysis algorithm on the automated instrument; or derive a final call for the assay, based on one or more assay-specific result algorithms or scripts.

22. The system of claim 21, wherein the instructions include instructions to cause the automated instrument to compare identifying indicia on a consumable package to a set of assay-specific identifying data stored on the automated instrument, and wherein the identifying indicia comprises a bar code.

23. The system of claim 22, wherein the system further comprises a bar code reader.

24. The system of claim 12, wherein at least one of the assay workflows comprises a reaction selected from the group consisting of: Polymerase Chain Reaction (PCR), Transcription Mediated Amplification (TMA), Oligonucleotide Ligation Assay (OLA), Ligase Chain Reaction (LCR), Rolling Circle Amplification (RCA), Strand Displacement Amplification (SDA), and a hybridization reaction.

* * * * *